United States Patent
Qian et al.

(10) Patent No.: US 10,214,724 B2
(45) Date of Patent: Feb. 26, 2019

(54) METHODS FOR DIFFERENTIATION OF HUMAN PLURIPOTENT STEM CELLS TO BRAIN MICROVASCULAR ENDOTHELIAL CELLS

(71) Applicant: Wisconsin Alumni Research Foundation, Madison, WI (US)

(72) Inventors: Tongcheng Qian, Madison, WI (US); Eric V. Shusta, Madison, WI (US); Sean P. Palecek, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/478,463

(22) Filed: Apr. 4, 2017

(65) Prior Publication Data

US 2017/0283772 A1    Oct. 5, 2017

Related U.S. Application Data

(60) Provisional application No. 62/318,405, filed on Apr. 5, 2016.

(51) Int. Cl.
*C12N 5/00* (2006.01)
*C12N 5/079* (2010.01)

(52) U.S. Cl.
CPC ........ *C12N 5/0618* (2013.01); *C12N 2500/38* (2013.01); *C12N 2500/90* (2013.01); *C12N 2501/115* (2013.01); *C12N 2501/415* (2013.01); *C12N 2506/45* (2013.01)

(58) Field of Classification Search
CPC ............................ C12N 5/0618; C12N 5/0696
See application file for complete search history.

(56) References Cited

U.S. PATENT DOCUMENTS

2012/0015395 A1    1/2012 Shusta

OTHER PUBLICATIONS

Weksler, et al., The hCMEC/D3 cell line as a model of the human blood brain barrier. Fluids Barriers CNS 2013, 10:16.
Wilson, et al., Exploring the effects of cell seeding density on the differentiation of human pluripotent stem cells to brain microvascular endothelial cells. Fluids and Barriers of the CNS 2015, 12:13.
Wong, et al., Upregulation of intercellular adhesion molecule-1 (ICAM-1) expression in primary cultures of human brain microvessel endothelial cells by cytokines and lipopolysaccharide. Journal of Neuroimmunology 1992, 39:11-21.
Abbott, et al., Astrocyte-endothelial interactions at the blood-brain barrier. Nature Reviews Neuroscience 2006, 7:41-53.
Asahi, et al., Effects of matrix metalloproteinase-9 gene knock-out on the proteolysis of blood-brain barrier and white matter components after cerebral ischemia. The Journal of Neuroscience 2001, 21:7724-7732.
Bauer, et al., "You Shall Not Pass"—tight junctions of the blood brain barrier. Frontiers in Neuroscience 2014, 8:392.
Belayev, et al., Quantitative evaluation of blood-brain barrier permeability following middle cerebral artery occlusion in rats. Brain Research 1996, 739:88-96.
Boyer-Di Ponio, et al., Instruction of circulating endothelial progenitors in vitro towards specialized blood-brain barrier and arterial phenotypes. PloS one 2014, 9:e84179.
Brines, et al., Erythropoietin crosses the blood-brain barrier to protect against experimental brain injury. Proceedings of the National Academy of Sciences 2000, 97:10526-10531.
Butt, et al., Electrical resistance across the blood-brain barrier in anaesthetized rats: a developmental study (1990) J. Physiol. 429:47-62.
Canfield, et al., An Isogenic Blood-Brain Barrier Model Comprising Brain Endothelial Cells, Astrocytes and Neurons Derived from Human Induced Pluripotent Stem Cells. Journal of Neurochemistry 2016.
Cecchelli, et al., A stable and reproducible human blood-brain barrier model derived from hematopoietic stem cells. PloS one 2014, 9:e99733.
Chambers, et al., Highly efficient neural conversion of human ES and iPS cells by dual inhibition of SMAD signaling. Nature Biotechnology 2009, 27:275-280.
Deli, Blood-brain barrier models. Handbook of Neurochemistry and Molecular Neurobiology: Neural Membranes and Transport 2007:29-55.
Ebert, et al., EZ spheres: a stable and expandable culture system for the generation of pre-rosette multipotent stem cells from human ESCs and iPSCs. Stem Cell Research 2013, 10:417-427.
Forster, et al., Differential effects of hydrocortisone and TNFalpha on tight junction proteins in an in vitro model of the human blood-brain barrier (2008) J. Physiol. (Lond.) 586:1937-49.
Frey, et al., Pericytes of the brain microvasculature express γ-glutamyl transpeptidase. European Journal of Biochemistry 1991, 202:421-429.
Gage, et al., Initial cell seeding density influences pancreatic endocrine development during in vitro differentiation of human embryonic stem cells. PloS one 2013, 8:e82076.
Geier, et al., Profiling solute carrier transporters in the human blood-brain barrier. Clinical Pharmacology & Therapeutics 2013, 94:636-639.
Huntley, et al., Dissecting gene expression at the blood-brain barrier. Frontiers in Neuroscience 2014, 8:355.
Kurz, Cell lineages and early patterns of embryonic CNS vascularization. Cell Adhesion & Migration 2009, 3:205-210.
Lai, et al., The critical component to establish in vitro BBB model: Pericyte. Brain Research Reviews 2005, 50:258-265.

(Continued)

*Primary Examiner* — Marcia S Noble
(74) *Attorney, Agent, or Firm* — Quarles & Brady LLP

(57) ABSTRACT

Methods for generating functional brain microvascular endothelial cells (BMECs) under chemically defined, serum-free conditions are provided. In particular, efficient and cost-effective methods for generating functional BMECs under chemically defined culture conditions are provided. BMECs obtained according to the methods provided herein are suitable for in vitro blood brain barrier (BBB) formation.

9 Claims, 20 Drawing Sheets
(16 of 20 Drawing Sheet(s) Filed in Color)
Specification includes a Sequence Listing.

(56) References Cited

OTHER PUBLICATIONS

Lam, et al., Rapid and efficient differentiation of human pluripotent stem cells into intermediate mesoderm that forms tubules expressing kidney proximal tubular markers. Journal of the American Society of Nephrology 2013:ASN. 2013080831.

Lian, et al., Chemically defined, albumin-free human cardiomyocyte generation. Nature Methods 2015, 12:595-596.

Lian, et al., Efficient differentiation of human pluripotent stem cells to endothelial progenitors via small-molecule activation of WNT signaling. Stem Cell Reports 2014, 3:804-816.

Lian, et al., Robust cardiomyocyte differentiation from human pluripotent stem cells via temporal modulation of canonical Wnt signaling. Proceedings of the National Academy of Sciences 2012, 109:E1848-E1857.

Liebner, et al., Current concepts of blood-brain barrier development. International Journal of Developmental Biology 2011, 55:467-476.

Liebner, et al., Wnt/β-catenin signaling controls development of the blood-brain barrier. The Journal of Cell Biology 2008, 183:409-417.

Lindsley, et al., Canonical Wnt signaling is required for development of embryonic stem cell-derived mesoderm. Development 2006, 133:3787-3796.

Lippmann, et al., A retinoic acid-enhanced, multicellular human blood-brain barrier model derived from stem cell sources. Scientific Reports 2014, 4:4160.

Lippmann, et al., Blood-brain barrier modeling with co-cultured neural progenitor cell-derived astrocytes and neurons. Journal of neurochemistry 2011, 119:507-520.

Lippmann, et al., Defined human pluripotent stem cell culture enables highly efficient neuroepithelium derivation without small molecule inhibitors. Stem Cells 2014, 32:1032-1042.

Lippmann, et al., Derivation of blood-brain barrier endothelial cells from human pluripotent stem cells. Nature Biotechnology 2012, 30:783-791.

Lippmann, et al., Modeling the blood-brain barrier using stem cell sources, Fluids and barriers of the CNS 2013, 10:2, pp. 1-14.

Lu et al., Effect of cell density on adipogenic differentiation of mesenchymal stem cells. Biochemical and Biophysical Research Communications 2009, 381:322-327.

Man, et al., Human brain microvascular endothelial cells and umbilical vein endothelial cells differentially facilitate eukocyte recruitment and utilize chemokines for T cell migration (2008) Clin. Dev. Immunol. 384982.

Minami, et al., Generation of Brain Microvascular Endothelial-Like Cells from Human Induced Pluripotent Stem Cells by Co-Culture with C6 Glioma Cells. PloS one 2015, 10:e0128890.

Mizee, et al., Astrocyte-derived retinoic acid: a novel regulator of blood-brain barrier function in multiple sclerosis. Acta Neuropathologica 2014, 128:691-703.

Mizee, et al., Retinoic acid induces blood-brain barrier development. The Journal of Neuroscience 2013, 33:1660-1671.

Naik, et al., In vitro blood-brain barrier models: current and perspective technologies. Journal of Pharmaceutical Sciences 2012, 101:1337-1354.

Nakagawa, et al., Pericytes from brain microvessels strengthen the barrier integrity in primary cultures of rat brain endothelial cells. Cellular and molecular neurobiology 2007, 27:687-694.

Obermeier, et al., Development, maintenance and disruption of the blood-brain barrier. Nature Medicine 2013, 19:1584-1596.

Otero, et al., β-Catenin signaling is required for neural differentiation of embryonic stem cells. Development 2004, 131:3545-3557.

Paolinelli, et al., Wnt activation of immortalized brain endothelial cells as a tool for generating a standardized model of the blood brain barrier in vitro. PLoS One 2013, 8:e70233.

Sano, et al., Establishment of a new conditionally immortalized human brain microvascular endothelial cell line retaining an in vivo blood-brain barrier function. Journal of Cellular Physiology 2010, 225:519-528.

Selekman, et al., Efficient generation of functional epithelial and epidermal cells from human pluripotent stem cells under defined conditions. Tissue Engineering Part C: Methods 2013, 19:949-960.

Stenman, et al., Canonical Wnt signaling regulates organ-specific assembly and differentiation of CNS vasculature. Science 2008, 322:1247-1250.

Stins, et al., Selective expression of adhesion molecules on human brain microvascular endothelial cells. Journal of Neuroimmunology 1997, 76:81-90.

Syvänen, et al., Species differences in blood-brain barrier transport of three positron emission tomography radioligands with emphasis on P-glycoprotein transport. Drug Metabolism and Disposition 2009, 37:635-643.

Weidenfeller, et al., Differentiating embryonic neural progenitor cells induce blood-brain barrier properties. Journal of neurochemistry 2007, 101:555-565.

Weksler, et al., Blood-brain barrier-specific properties of a human adult brain endothelial cell line. The FASEB Journal 2005, 19:1872-1874.

FIGS. 2A-2K, CONTINUED
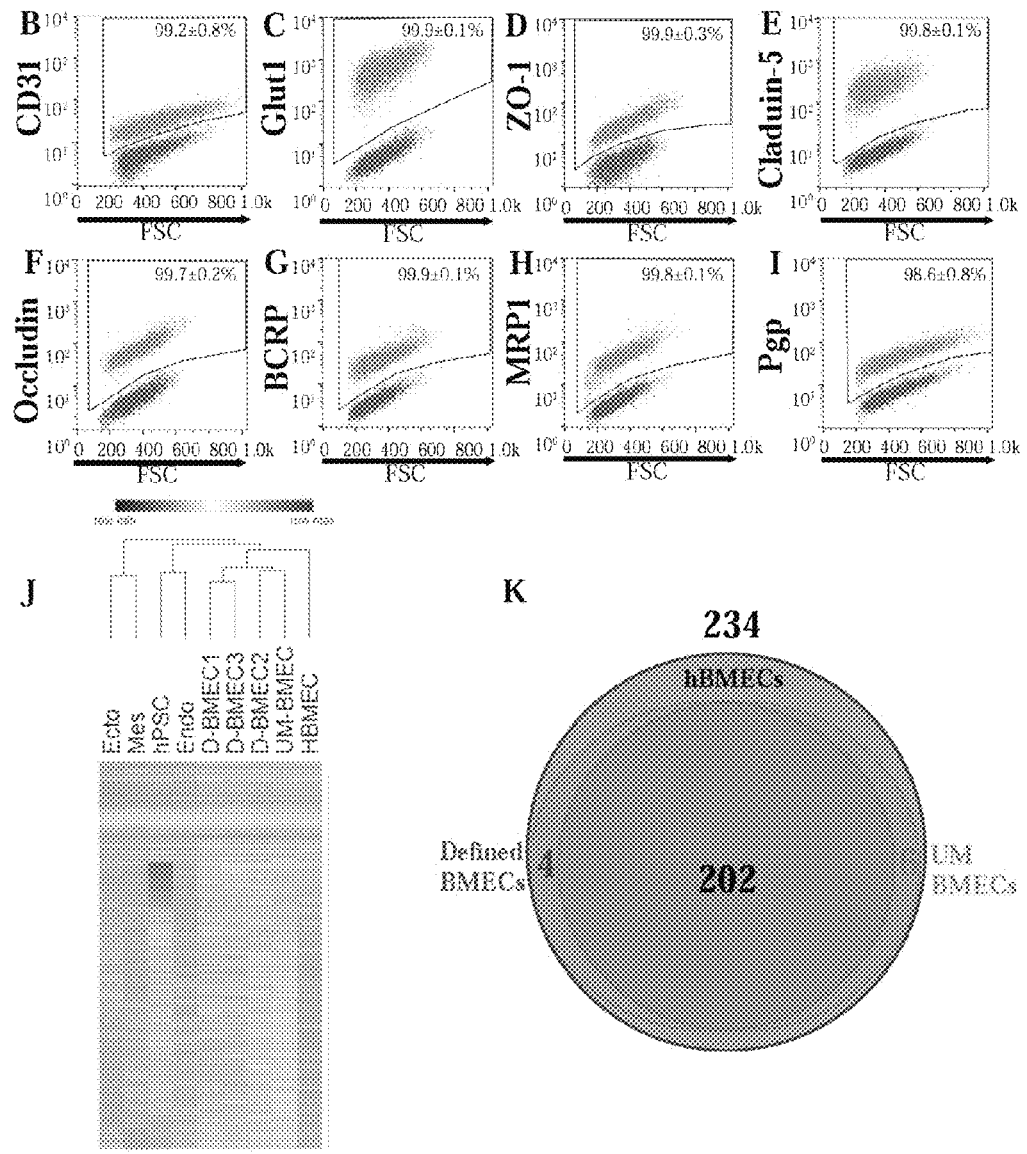

FIGS. 3A-3K, CONTINUED
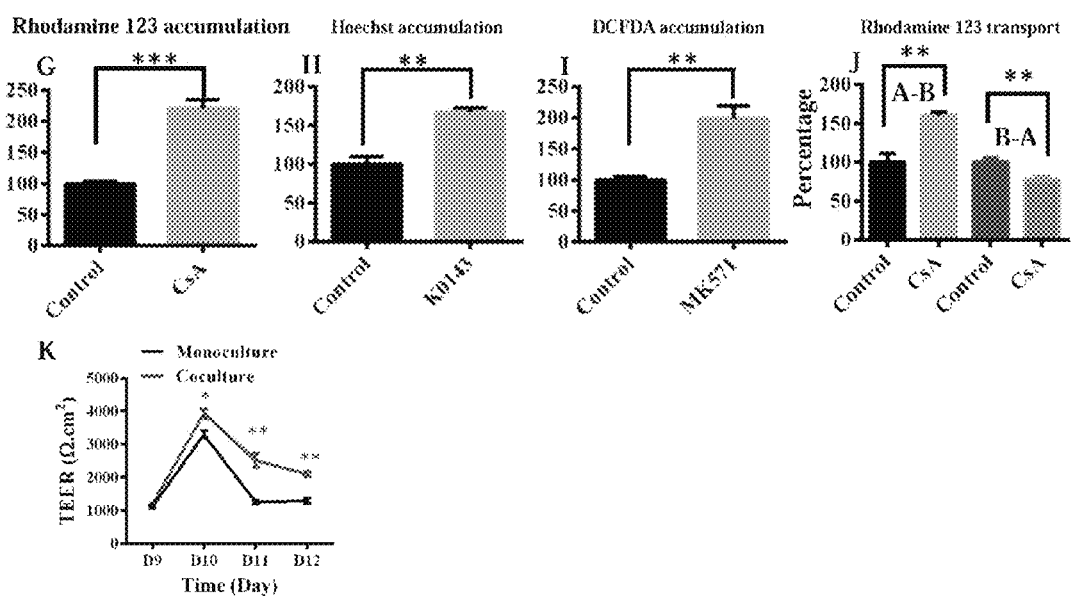

FIGS. 4A-4J, CONTINUED
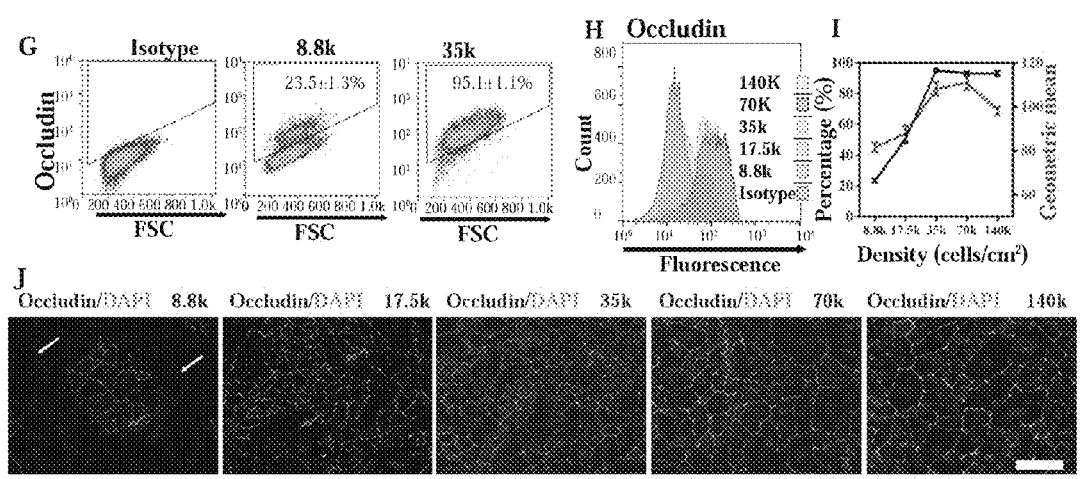

(A) H9-BMECs (B) 19-9-11-BMECs

FIGS. 12A-12B, CONTINUED
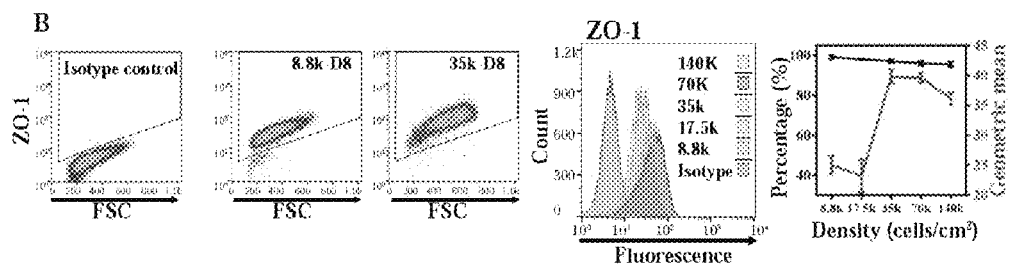

METHODS FOR DIFFERENTIATION OF HUMAN PLURIPOTENT STEM CELLS TO BRAIN MICROVASCULAR ENDOTHELIAL CELLS

CROSS-REFERENCE TO RELATED APPLICATIONS

This application claims the benefit of U.S. Application Ser. No. 62/318,405, filed Apr. 5, 2016, which is incorporated herein as if set forth in its entirety.

STATEMENT REGARDING FEDERALLY SPONSORED RESEARCH OR DEVELOPMENT

This invention was made with government support under NS085351 awarded by the National Institutes of Health. The government has certain rights in the invention.

BACKGROUND

The blood-brain barrier (BBB) is a dynamic interface between the blood and the central nervous system (CNS) that controls the influx and efflux of biological substances needed for the brain's metabolic processes, as well as for neuronal function. The BBB comprises specific endothelial cells, brain microvascular endothelial cells (BMECs), which are critical for maintaining homeostasis of the brain microenvironment and neurological health.

In vitro BBB models have been developed to study the molecular mechanisms underlying development of the BBB and to screen for drugs and other chemical compounds that affect BBB integrity. Naik & Cucullo, *J Pharm Sci.* 2012, 101(4):1337-54; Lippmann et al., *Nature Biotechnology* 2012, 30:783-791. In order to understand development of the BBB and mechanisms underlying neurological diseases, it is critical to have a renewable source of human BMECs. However, existing methods for differentiating human pluripotent stem cells to BMECs use undefined culture systems that exhibit line-to-line variability, making the methods poorly suited for clinical applications and large scale production. Accordingly, there remains a need in the art for efficient and cost-effective protocols for generating functional brain microvascular endothelial cells under chemically defined culture conditions.

BRIEF SUMMARY

In a first aspect, provided herein is a method for generating a population of human brain microvascular endothelial cells (BMECs) from human pluripotent stem cells, where the method comprises, in order, (a) culturing human pluripotent stem cells for about 24 hours in a chemically defined, serum-free culture medium that comprises an activator of Wnt/β-catenin signaling, whereby cells that express mesodermal markers are obtained; (b) culturing the cells expressing mesodermal markers for about 5 days in the presence of a chemically defined, serum-free culture medium comprising B27 supplement, whereby cells that express endothelial progenitor marker Flk-1 are obtained; and (c) culturing the Flk-1+ cells of (b) for about two days in the presence of a chemically defined, serum-free endothelial medium comprising B27 supplement, bFGF/FGF2, and retinoic acid (RA), whereby a cell population comprising human BMECs is obtained.

In some cases, at least 95% of cells of the cell population of (c) are BMECs cells positive for expression of $CD31^+$, p-glycoprotein$^+$ ($Pgp^+$), and claudin-$5^+$. The method can further comprise growing the human BMECs of step (c) as a monolayer to confluence. In some cases, the method comprises taking an initial transendothelial electrical resistance (TEER) measurement of the confluent monolayer, where the TEER measurement is greater than 2000 Ohm $(\Omega) \times cm^2$.

The activator of Wnt/β-catenin signaling can be a Gsk3 inhibitor. The Gsk3 inhibitor can be a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide. The Gsk3 inhibitor can be CHIR99021 and present in a concentration of about 3 μM to about 12 μM. Preferably, no cell separation or selection step is used to obtain the cell population comprising BMECs.

In another aspect, provided herein is a human BMEC cell population according to the methods described herein.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

Figures 1A, 1B, 1C, 1D, 1E, 1F, 1G, 1H, 1I, 1J:
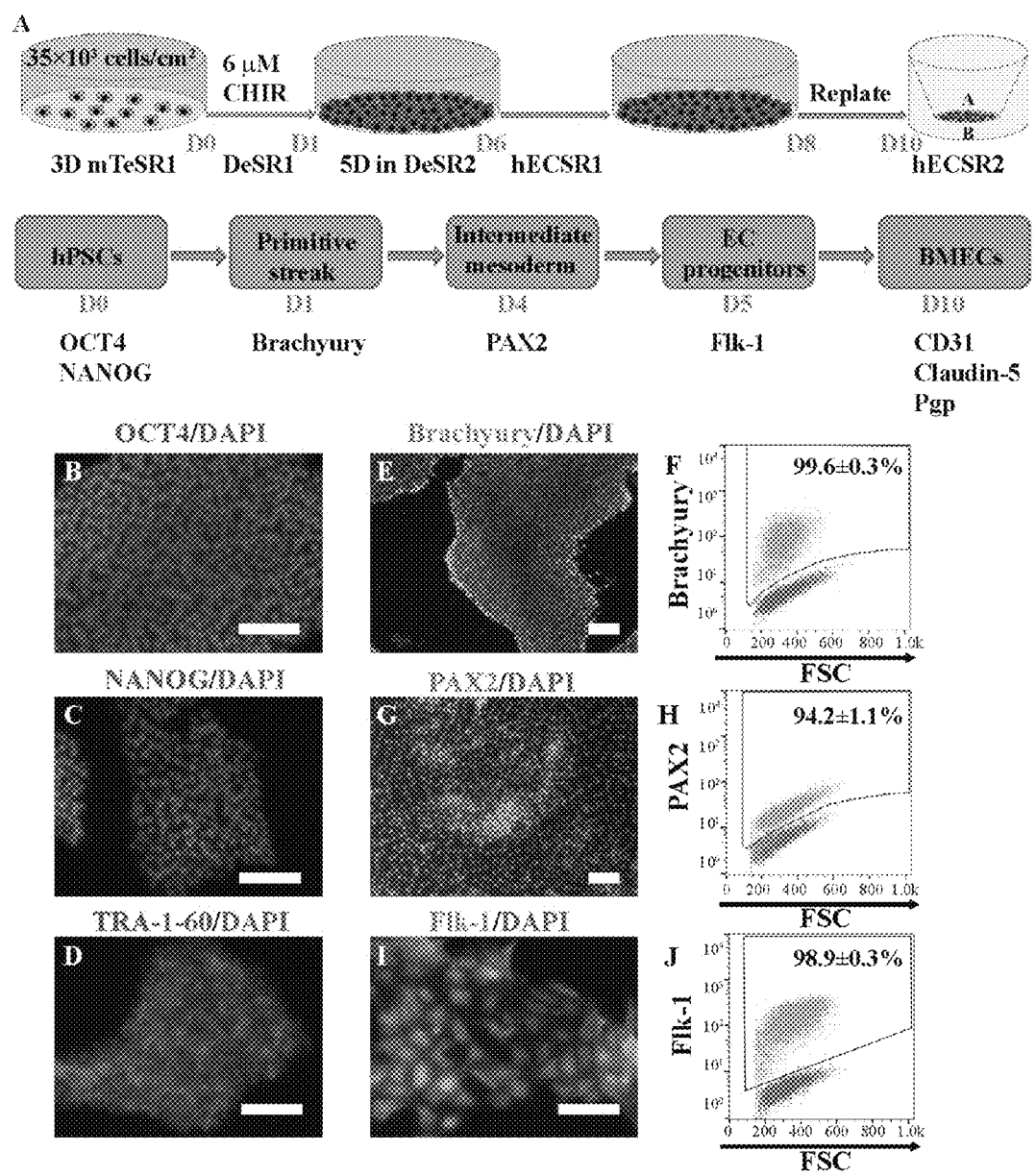
FIGS. 1A-1J present a schematic of BMEC differentiation protocol and progression of differentiation. (A) Singularized hPSCs are seeded on six-well plates coated with Matrigel®, vitronectin or SyntheMAX™ substrate and expanded for 3 days in mTeSR1™. Differentiation to primitive streak is initiated by 24 hour treatment with 6 μM CHIR99201 in DeSR1. Cells progress to intermediate mesoderm and endothelial progenitors during culture in serum-free defined DeSR2 medium. At day 6, BMEC specification is induced by culture in hESFM ("Human Endothelial-SFM," a basal serum-free growth medium that supports endothelial cells) supplemented with 2% B27 (50×), 10 μM RA and 20 ng/ml b-FGF/FGF2 (known as "hECSR1") for two days. After replating on Matrigel® or fibronectin/collagen IV substrates, BMECs are obtained. (B) The pluripotent state of expanded hPSCs was verified prior to differentiation by immunostaining for OCT4 (B), NANOG (C) and TRA1-60 (D). Expression of the primitive streak marker Brachyury was assessed by immunostaining (E) and flow cytometry (F) 24 hours after CHIR99021 treatment. On day 4 of differentiation, expression of the intermediate mesoderm marker PAX2 was quantified (G, H) and on day 5 the endothelial progenitor marker Flk-1 analyzed (I, J). Scale bar 100 μm.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Existing methods for differentiating human pluripotent stem cells into brain microvascular endothelial cells (BMECs) use undefined culture systems that tend to exhibit line-to-line variability, including variability in cell density at the start of each differentiation protocol. See, e.g., U.S. patent application Ser. No. 13/155,435 (incorporated by reference herein). The methods and compositions provided herein are based at least in part on the Inventors' discovery of a robust, chemically defined, and serum-free method for directing differentiation of human pluripotent stem cells (hPSCs) to BMECs. The current invention uses a defined system comprised of an activator of Wnt/β-catenin signaling and retinoic acid in a chemically defined, serum free medium. As described in this section and in the Examples that follow, pluripotent stem cell-derived BMECs exhibit endothelial properties, including tube formation and LDL uptake, as well as BMEC-specific efflux transporter activities. Notably, hPSC-derived BMECs cells exhibit physiologic transendothelial electrical resistance (TEER) (around 3000 Ω·cm²). In this manner, the methods described herein provide an unlimited supply of BMECs having properties comparable to those of primary BMECs.

Accordingly, in a first aspect, provided herein is a method for generating BMEC cells, where the method comprises differentiating hPSCs under conditions that promote differentiation of the hPSCs into BMECs cells. A preferred embodiment of the method is described in FIG. 1A. In general, the method of the present invention has the following steps:

Human pluripotent stem cells (hPSCs) are cultured for about 24 hours in a chemically defined, serum-free culture medium comprising an activator of Wnt/β-catenin signaling. As described elsewhere in this document, hPSCs include both hESCs and iPSCs. Any chemically defined, unconditioned (meaning, free of conditioning by mouse fibroblast feeders or other feeder cells) culture medium can be used provided that it comprises an activator of Wnt/β-catenin signaling. In preferred embodiments, the chemically defined, serum-free medium comprises DMEM/F12, 0.5% GlutaMax, 1% MEM-NEAA, 100 μm β-mercaptoethanol. Various activators of Wnt/β-catenin signaling that can be used are described elsewhere in this document. This process directs hPSCs through mesodermal lineages as evidenced by expression of mesoderm-specific genes and proteins such as brachyury/T and PAX2.

In a second step, the cells expressing mesoderm-specific markers obtained in the first step are cultured for about 5 days in the presence of a chemically defined, serum-free culture medium comprising a defined, serum-free B27 supplement, whereby cells that express endothelial progenitor marker Flk-1 are obtained. In preferred embodiments, the chemically defined, serum-free medium is DMEM/F12 supplemented with B27 ("DMEM/F12/B27"). B27 is commercially available from suppliers such as Invitrogen.

Next, the Flk-1$^+$ cells are cultured for about two days in the presence of a chemically defined, serum-free endothelial medium comprising B27 supplement and retinoic acid (RA), whereby a cell population comprising human BMECs is obtained. In preferred embodiments, the chemically defined, serum-free endothelial medium is human Endothelial Serum-Free Medium (hESFM) (Invitrogen) supplemented with B27 and about 10 μM retinoic acid (RA). RA enhances the functional properties and maturation of BMECs. In some cases, the endothelial medium further comprises bFGF/FGF2. For example, in exemplary methods, cells are cultured on day 6, day 7, day 8, and day 9 in chemically defined, serum-free endothelial medium comprising 2% B27 supplement, 10 μM RA, and 20 ng/ml bFGF/FGF2.

Preferably, hPSCs are seeded as singularized cells to attain greater uniformity of hPSC density at the initiation of BMEC differentiation. For example, hPSCs can be seeded as singularized cells at day minus 3 ("day −3"; 3 days before BMEC differentiation in the presence of a chemically defined, serum-free culture medium comprising a defined, serum-free B27 supplement) at a cell density between about 8K cells/cm$^2$ and about 200K cells/cm$^2$ (e.g., about 8 cells/cm$^2$, 10K cells/cm$^2$, 12.5K cells/cm$^2$, 20K cells/cm$^2$, 25K cells/cm$^2$, 30K cells/cm$^2$, 35K cells/cm$^2$, 50K cells/cm$^2$, 100K cells/cm$^2$, 140K cells/cm$^2$, 200K cells/cm$^2$). Preferably, hPSCs are seeded as singularized cells at a density between about 30K cells/cm$^2$ and about 70K cells/cm$^2$. More preferably, hPSCs are seeded as singularized cells at a density of about 35K cells/cm$^2$. As demonstrated in the Example that follows, cell seeding density affects BMEC differentiation and structural organization of BMEC tight junction proteins. Without being bound by any particular theory or mechanism of action, it is believed that cell seeding density affects the capability for the endothelial progenitors to gain BMEC properties.

Useful gene expression or protein markers for identifying BMECs include, but are not limited to, CD31, Pgp, claudin-5, and occludin, BCRP1, MRP1, and combinations thereof. CD31 is an endothelial cell marker. Claudin-5 and Occludin are integral plasma-membrane proteins located at tight junctions including tight junctions between brain endothelial cells. P-glycoprotein (Pgp), Breast Cancer Resistance Protein (BCRP), and Multidrug Resistance-Associated Protein (MRP) are efflux transporters. Preferably, the method yields a cell population, at least 95% (e.g., at least 95%, 96%, 97%, 98%, 99% or more) of which are BMECs positive for expression of one or more of Pgp, occludin, and claudin-5. Molecular markers of BMECs can be detected at the mRNA expression level or protein level by standard methods in the art. In some embodiments, no cell separation step or method is used to obtain a cell population comprising at least 90% Pgp$^+$ cells or at least 95% Pgp$^+$ cells. In other embodiments, the proportion of BMECs in a population of cells obtained in the described methods is enriched using a cell separation, cell sorting, or enrichment method, e.g., fluorescence activated cell sorting (FACS), enzyme-linked immunosorbent assay (ELISA), magnetic beads, magnetic activated cell sorting (MACS), and combinations thereof. Preferably, FACS is used to identify and separate cells based on expression of endothelial markers appropriate for sorting other endothelial cell populations.

In some embodiments, certain BMEC functional criteria are also assessed. Such functional BMEC criteria include, without limitation, tube formation, LDL uptake, and BMEC-specific efflux transporter activities. In vitro tube formation can be assayed using an endothelial cell tube formation assay. See, for example, Jerkic et al. (2006) *Cardiovasc Res* 69:845-854. Efflux transporter activity can be assessed by detecting intracellular accumulation of a fluorescent transporter substrate or movement of a fluorescent transporter substrate across a confluent monolayer BMECs.

In some cases, it will be advantageous to obtain a transendothelial electrical resistance (TEER) measurement of BMECs obtained according to the methods provided herein. TEER measurements yield information regarding the integrity of a BMEC monolayer by monitoring the paracellular flux of small electrolytes. BMECs cells obtained according to the methods provided herein exhibit transendothelial electrical resistance of greater than about 300Ω×cm$^2$. In some cases, the BMECs exhibit physiologic TEER measurements (about 1000Ω×cm$^2$ to about 5000Ω×cm$^2$). By comparison, immortalized BMECs have poor barrier properties, including low baseline transendothelial electrical resistance (TEER) and discontinuous tight junction protein expression (Weksler et al. (2005) *FASEB J.* 19:1872-1874; Forster et al. (2008) *J. Physiol.* (*Lond.*) 586:1937-49; Man et al. (2008) *Clin. Dev. Immunol.* 384982). The in vivo BBB has been measured in rats to be between 1000-3000Ω×cm$^2$ (see Butt et al. (1990) *J. Physiol.* 429:47-62). TEER measurements can be carried out using a voltammeter according to any appropriate protocol.

The methods provided herein produce isolated populations of pluripotent stem cell-derived BMECs, where the isolated population is a substantially pure population of BMECs. As used herein, "isolating" and "isolated" refer to separating, selecting, or enriching for a cell type of interest or subpopulation of cells from surrounding, neighboring, or contaminating cells or from cells of another type. As used herein, the term "substantially pure" refers to a population of cells that is at least about 75% (e.g., at least about 75%, 80%, 85%, 90%, 95%, 98%, 99% or more) pure, with respect to BMECs making up a total cell population. In other words, the term "substantially pure" refers to a population of BMECs of the present invention that contains fewer than about 25%, fewer than about 20%, fewer than about 10%, or fewer than about 5% of non-BMECs when directing differentiation to obtain cells of the BMEC lineage. The term "substantially pure" also refers to a population of BMECs of the present invention that contains fewer than about 20%, about 10%, or about 5% of non-BMECs in an isolated population prior to any enrichment, expansion step, or differentiation step. Typically, a population comprising BMECs obtained by the disclosed methods comprises a very high proportion of BMECs. In some embodiments, the cell population comprises about 50% to about 99% BMECs, e.g., about 52%, 55%, 67%, 70%, 72%, 75%, 80%, 85%, 90%, 95%, 98%, or another percent of BMECs from about 50% to about 99% BMECs.

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibiting Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase the level of β-catenin and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al. (2002), *J. Biol. Chem.*, 277(26):23330-23335, which describes a Gsk3 comprising a R96A mutation.

In some embodiments, Gsk3 is inhibited by contacting a cell with a small molecule that inhibits Gsk3 phosphotransferase activity or Gsk3 binding interactions. Suitable small molecule Gsk3 inhibitors include, but are not limited to, CHIR99021, CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 µM to about 12 µM, e.g., about 3 µM, 4 µM, 5 µM, 6 µM, 7 µM, 8 µM, 9 µM, 10 µM, 11 µM, 12 µM or another concentration of CHIR99021 from about 3 µM to about 12 µM. In another embodiment, the small molecule Gsk3 inhibitor to be used is CHIR98014 at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of CHIR98014 from about 0.1 µM to about 1 µM. In another embodiment, the small molecule Gsk3 inhibitor to be used is BIO-acetoxime at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of BIO-acetoxime from about 0.1 µM to about 1 µM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNA interference (RNAi) system from Clontech (Mountain View, Calif., Catalog No. 630926), or a cumate-inducible system from Systems Biosciences, Inc. (Mountain View, Calif.), e.g., the SparQ® system, catalog no. QM200PA-2.

In other embodiments, the Wnt/β-catenin signaling pathway is activated by overexpressing β-catenin itself, e.g., human β-catenin (exemplary nucleotide and amino acid sequences are found at GenBank Accession Nos: X87838 and CAA61107.1, respectively). In one embodiment, β-catenin overexpression is achieved using an inducible expression system, e.g., any of the just-mentioned inducible expression systems. Alternatively, a constitutively active, stabilized isoform of β-catenin is used, which contains point mutations S33A, S37A, T41A, and S45A as described, e.g., in Baba et al. (2005), *Immunity* 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of the Axin/β-catenin interaction allows β-catenin to escape degradation by the destruction complex thereby increasing the net level of β-catenin to drive β-catenin signaling. For example, the Axin/β-catenin interaction can be disrupted in pluripotent cells by contacting the cells with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD Millipore. An effective concentration of SKL2001 to activate Wnt/β-catenin signaling ranges from about 10 µM to about 100 µM, about 20 µM, 30 µM, 40 µM, 50 µM, 60 µM, 70 µM, 80 µM, 90 µM or another concentration of SKL2001 from about 10 µM to about 100 µM.

As used herein, "pluripotent stem cells" appropriate for use according to a method of the invention are cells having the capacity to differentiate into cells of all three germ layers. Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs). As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60, and TRA-1-81, and appear as compact colonies having a high nucleus to cytoplasm ratio and prominent nucleolus. ESCs are commercially available from sources such as WiCell Research Institute (Madison, Wis.).

As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007). Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60, or Tra-1-81, but not SSEA-1). Induced pluripotent stem cells, however, are not immediately derived from embryos. As used herein, "not immediately derived from embryos" means that the starting cell type for producing iPS cells is a non-embryonic, non-pluripotent cell, such as a multipotent cell or terminally differentiated cell, such as somatic cells obtained from a post-natal individual.

Human iPS cells can be used according to a method described herein to obtain BMECs having the genetic complement of a particular human subject. For example, it may be advantageous to obtain BMECs that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009); Howden et al., *Proc. Natl. Acad. Sci. U.S.A* 108(16):6537-42 (2011). Induced pluripotent stem cell-derived BMECs allow modeling of blood brain barrier formation or integrity using BMECs and other BBB cell types obtained from an individual having, for example, a particular disease.

Subject-specific somatic cells for reprogramming into iPS cells can be obtained or isolated from a target tissue of interest by biopsy or other tissue sampling methods. In some cases, subject-specific cells are manipulated in vitro prior to use. For example, subject-specific cells can be expanded, differentiated, genetically modified, contacted to polypeptides, nucleic acids, or other factors, cryo-preserved, or otherwise modified.

Chemically defined culture medium and substrate conditions for culturing pluripotent stem cells, as used in the methods described herein, are well known in the art. Preferably, a serum-free, chemically defined culture medium is used. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein, "serum-free" means that a medium does not contain serum or serum replacement, or that it contains essentially no serum or serum replacement. For example, an essentially serum-free medium can contain less than about 0.5%, 0.4%, 0.3%, 0.2% or 0.1% serum.

In some embodiments, pluripotent stem cells to be differentiated according to the methods disclosed herein are cultured in the presence of a serum-free, chemically-defined culture medium such as mTESR1™ medium (StemCell Technologies, Inc., Vancouver, Calif.), or Essential 8® medium (Life Technologies, Inc.) on a Matrigel® substrate (BD Biosciences, NJ), a Synthemax® synthetic cell culture surface (Corning) according to the manufacturer's protocol, or a vitronectin-coated surface. A number of known basal culture media are suitable for use throughout the differentiation methods described herein. Such basal cell culture media include, but are not limited to, RPMI, DMEM/F12 (1:3), DMEM/F12 (1:1), DMEM/F12 (3:1), F12, DMEM, and MEM. In exemplary embodiments, these basal cell culture media are supplemented with 50 to 200 µg/ml L-Ascorbic acid 2-phosphate sesquimagnesium salt hydrate (e.g., Sigma, catalog no. A8960).

In exemplary embodiments, human pluripotent stem cells (e.g., human ESCs or iPS cells) are cultured in the absence of a feeder layer (e.g., a fibroblast layer) and in the presence of a chemically defined substrate. For example, human pluripotent cells can be cultured in the presence of a substrate comprising vitronectin, a vitronectin fragment or variant, a vitronectin peptide, a self-coating substrate such as Synthemax® (Corning), or combinations thereof. In exemplary embodiments, the chemically-defined substrate is a plate coated in vitronectin peptides or polypeptides (e.g., recombinant human vitronectin).

In another aspect, provided herein are methods for obtaining functional human BMECs, where the method comprises differentiating cells having mesoderm identity under conditions that promote differentiation of the mesoderm cells into BMECs cells. In general, such methods can use cells that express mesoderm-specific genes and proteins such as brachyury/T and PAX2, and have the following steps:

Cells expressing mesoderm-specific markers are cultured for about 5 days in the presence of a chemically defined, serum-free culture medium comprising a defined, serum-free B27 supplement, whereby cells that express endothelial progenitor marker Flk-1 are obtained. In preferred embodiments, the chemically defined, serum-free medium is DMEM/F12 supplemented with B27 ("DMEM/F12/B27"). B27 is commercially available from suppliers such as Invitrogen.

Next, the Flk-1$^+$ cells are cultured for about two days in the presence of a chemically defined, serum-free endothelial medium comprising B27 supplement and retinoic acid (RA), whereby a cell population comprising human BMECs is obtained. In preferred embodiments, the chemically defined, serum-free endothelial medium is human Endothelial Serum-Free Medium (hESFM) (Invitrogen) supplemented with B27 and about 10 µM retinoic acid (RA). RA enhances the functional properties and maturation of BMECs.

It will be understood by those practitioners in the art that BMECs obtained according to the methods provided herein are suitable for in vitro blood brain barrier (BBB) formation. Importantly, BMECs obtained according to the chemically defined, serum-free methods provided herein are better suited for in vitro BBB models than BMECs obtained using undefined culture systems that exhibit line-to-line variability. In some cases, an in vitro BBB is obtained by co-culturing BMECs obtained according to the methods provided herein with other cell types associated with the blood brain barrier including, without limitation, astrocytes, neurons, and pericytes. Astrocytes, neurons, and pericytes suitable for preparation of an in vitro BBB can be obtained according to chemically defined, serum-free differentiation protocols, or can be primary cells or obtained from primary cell cultures. As described in the Examples that follow, hPSC-derived BMECs can be co-cultured in vitro with human pericytes, astrocytes, and/or neurons in a medium that supports growth of endothelial cells (e.g., hECSR medium).

In a further aspect, provided herein is a method of in vitro screening of an agent. For example, provided herein are methods of using in vitro-derived BMECs for high throughput screening of candidate agents. For example, BMECs obtained as described herein can be screened to identify agents that modulate development of BBB tissue. Screening methods can comprise or consist essentially of (a) contacting a test agent to a BMEC or population of BMECs obtained as described herein; and (b) detecting an effect of the agent on the cell or cells (e.g., disrupt or otherwise alter the integrity of a BMEC monolayer). In some cases, screening methods include screening candidate compounds to identify test agents that promote the development of blood brain barrier tissue. In other cases, candidate compounds can be screened for toxicity to human BMECs or blood brain barrier tissue. In some cases, detecting comprises detecting at least one positive or negative effect of the agent on morphology or life span of cells, whereby an agent that increases or reduces the life span of the cells or has a positive or negative impact on the morphology of the cells is identified as having an effect on human BMECs or blood brain barrier tissues. In some cases, detecting comprises performing a method selected from the group consisting of TEER assays, adhesion assays, RNA sequencing, gene expression profiling, transcriptome analysis, metabolome analysis, detecting reporter or sensor, protein expression profiling, Förster resonance energy transfer (FRET), metabolic profiling, and microdialysis. The agent can be screened for an effect on gene expression, and detecting can comprise assaying for differential gene expression relative to an uncontacted cell or cell population.

In exemplary embodiments, detecting and/or measuring a positive or negative change in a level of expression of at least one gene following exposure (e.g., contacting) of a test compound to BMECs comprises whole transcriptome analysis using, for example, RNA sequencing. In such cases, gene expression is calculated using, for example, data processing software programs such as Light Cycle, RSEM (RNA-seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at $P<0.05$. Any appropriate method can be used to isolate RNA or protein from neural constructs. For example, total RNA can be isolated and reverse transcribed to obtain cDNA for sequencing.

Test compounds can be dissolved in a solvent such as, for example, dimethyl sulfoxide (DMSO) prior to contacting to BMECs provided herein. In some cases, identifying agents comprises analyzing the contacted BMECs for positive or negative changes in biological activities including, without limitation, gene expression, protein expression, cell viability, and cell proliferation. For example, microarray methods can be used to analyze gene expression profiles prior to, during, or following contacting the plurality of test compounds to the BMECs. In some cases, a method of the present invention further comprises additional analyses such as metabolic assays and protein expression profiling.

Compositions

In another aspect, provided herein are preparations of BMECs. For example, provided herein are BMECs, substantially purified populations of BMECs, pharmaceutical preparations comprising BMECs, and cryopreserved preparations of the BMECs. The BMECs described herein may be substantially free of at least one protein, molecule, or other impurity that is found in its natural environment (e.g., "isolated"). The BMECs may be mammalian, including, human BMECs. The invention also provides human BMECs, a substantially purified population of human BMECs, pharmaceutical preparations comprising human BMECs, and cryopreserved preparations of the human BMECs. The preparation may be a preparation comprising human embryonic stem cell-derived BMECs, human iPS cell-derived BMECs, and substantially purified (with respect to non-BMECs) preparations comprising differentiated pluripotent stem cell-derived BMECs.

Cell preparations provided herein are useful for various in vitro and in vivo applications such as screening for drugs affecting homeostasis of the brain microenvironment, neural development, and/or the integrity of a BMEC monolayer. The disclosed methods facilitate scalable and reproducible production and use of functional BMEC populations.

Preparations comprising BMECs useful for clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of a cell therapy product, such as in vitro populations of human arterial endothelial cells, GTPs govern donor consent, traceability, and infectious disease screening, whereas the GMP is relevant to the facility, processes, testing, and practices to produce a consistently safe and effective product for human use. See Lu et al., *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

Articles of Manufacture

The invention also provides a kit for obtaining functional brain microvascular endothelial cells by differentiating human pluripotent stem cells under chemically defined culture conditions. In some cases, the kit comprises (i) a first chemically defined, serum-free culture medium suitable for differentiation of human pluripotent stem cells into cells expressing mesodermal markers; (ii) a second culture medium suitable for differentiation of pluripotent stem cell-derived mesodermal cells into cells that express endothelial progenitor marker Flk-1; (iii) a third chemically defined, serum-free endothelial medium comprising B27 supplement, bFGF/FGF2, and retinoic acid (RA); and (iv) instructions describing a method for differentiating human pluripotent stem cells into functional brain microvascular endothelial cells, the method employing the first, second, and third culture media. In some cases, the first chemically defined culture medium comprises an activator of Wnt/β-catenin signaling. In some cases, the second chemically defined culture medium comprises B27 supplement.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

In the specification and in the claims, the terms "including" and "comprising" are open-ended terms and should be interpreted to mean "including, but not limited to . . . ." These terms encompass the more restrictive terms "consisting essentially of" and "consisting of" As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising," "including," "characterized by," and "having" can be used interchangeably.

As used herein, "about" means within 5% of a stated concentration range or within 5% of a stated time frame.

As used herein, "a medium consisting essentially of" means a medium that contains the specified ingredients and those that do not materially affect its basic characteristics.

The terms "defined culture medium," "defined medium," and the like, as used herein, indicate that the identity and quantity of each medium ingredient is known. The term "defined," when used in relation to a culture medium or a culture condition, refers to a culture medium or a culture condition in which the nature and amounts of approximately all the components are known.

As used herein, "effective amount" means an amount of an agent sufficient to evoke a specified cellular effect according to the present invention.

Cells are "substantially free" of exogenous genetic elements or vector elements, as used herein, when they have less than 10% of the element(s), and are "essentially free" of exogenous genetic elements or vector elements when they have less than 1% of the element(s). However, even more desirable are cell populations wherein less than 0.5% or less than 0.1% of the total cell population comprise exogenous genetic elements or vector elements. A culture, composition, or culture medium is "essentially free" of certain reagents, such as signaling inhibitors, animal components or feeder cells, when the culture, composition, and medium, respectively, have a level of these reagents lower than a detectable level using conventional detection methods known to a person of ordinary skill in the art or these agents have not been extrinsically added to the culture, composition, or medium.

The invention will be more fully understood upon consideration of the following non-limiting Examples. It is specifically contemplated that the methods disclosed are suited for pluripotent stem cells generally. All publications, patents, and patent applications disclosed herein are hereby incorporated by reference as if set forth in their entirety.

EXAMPLES

Obtaining Brain Microvascular Endothelial Cells from Human Pluripotent Stem Cells Via Wnt Signaling Modulation An intact blood-brain barrier (BBB) serves as a key interface between the blood circulation and central nervous system (CNS). The primary anatomical component of the BBB is provided by brain microvascular endothelial cells (BMECs) [1,2] that work in concert with supporting cells such as astrocytes, pericytes, and neurons to form the neurovascular unit [1,3,4]. BMECs are connected by tight junctions and display low levels of vesicular traffic, leading to extremely low vascular permeability. BMECs also express molecular influx and efflux transporters, which regulate the delivery of nutrients from blood to brain and removal of compounds from the brain, respectively. A functional BBB prevents the majority of small molecule drugs and nearly all large molecule biologics from entering the brain [5]. Thus, the BBB is a highly efficient barrier that protects the brain and limits CNS drug delivery [6]. Moreover, BBB dysfunction has been associated with many CNS disorders, including stroke [7-9], Alzheimer's disease [10, 11], multiple sclerosis [12], Parkinson's disease [13], traumatic brain injury [14,15] and HIV [16-18].

Although the BBB has been extensively studied in animal models [19-21], and using in vitro models based on primary human BMECs [22,23] and immortalized human brain endothelial cell lines [2,24,25], these models lack key attributes of the human BBB. Animal models cannot fully represent the human BBB due to species differences, particularly in transporter expression and function [26]. Human primary BMECs are difficult to obtain in sufficient quantities for drug screening and disease models and cannot be readily expanded in culture. Immortalized cell lines exhibit a loss of BMEC-specific properties, including loss of tight junctions yielding sub-physiologic TEER [27]. These limitations have prevented our full understanding of human BBB development, function and disease [28].

hPSCs have the potential to generate large quantities of specialized human cells for studying development and modeling disease [29-31]. Previously, we reported generation of pure populations of hPSC-derived BMECs via co-differentiation of hPSCs to neural and endothelial progenitors followed by selective purification of the BMECs [32]. In addition, we demonstrated that retinoic acid (RA) addition during BMEC differentiation enhanced barrier properties to physiologic levels [33]. Presumably, the neural progenitors in this co-differentiation platform induce the endothelial progenitors to acquire BMEC-specific traits, which are then enhanced by RA treatment. However, the undefined nature of this co-differentiation platform complicates investigation of mechanisms that specify BMEC fates in the hPSC-derived endothelial cells. In addition, this undefined protocol can result in line-to-line and batch-to-batch variability in BMEC yield and phenotypes [32,34,35]. Other studies have also shown human BMEC-like cells can be generated from alternative stem and progenitor cell sources, including hematopoietic stem cells [36], endothelial progenitors [37], and hPSC-derived endothelial cells (ECs) co-cultured with C6 glioma cells [38]. Unfortunately, none of these prior studies report a chemically-defined, robust process for generating human BMECs exhibiting physiologic BBB phenotypes.

During embryonic development, mesoderm-derived endothelial cells form a vascular plexus covering the developing neural tube [39,40]. As nascent blood vessels enter the developing CNS, canonical Wnt signaling is necessary to induce BMEC barrier properties [41-43]. RA has also been shown to regulate BMEC specification. During BBB development, radial glial cells supply the CNS with RA [44], and this RA signaling induces barrier formation and BBB-specific gene expression [33,44,45]. In addition to Wnt regulation of BBB induction in vivo, prior studies have demonstrated that activation of canonical Wnt signaling can also direct hPSCs to mesodermal lineages in vitro [31,46-48]. Thus, we hypothesized that appropriate differentiation stage-specific modulation of canonical Wnt would induce mesodermal and endothelial commitment in hPSCs, and combine with subsequent RA signaling to drive acquisition of BMEC markers and phenotypes.

Here we report a chemically-defined method to differentiate hPSCs to BMECs via sequential Wnt and RA pathway activation. During this differentiation process, hPSCs progress through primitive streak, intermediate mesoderm, and Flk1$^+$ endothelial progenitors to generate virtually pure populations of CD31$^+$ endothelial cells that display key BMEC phenotypes including tight junctions, low passive permeability and polarized efflux transporters. The resultant, developmentally-relevant BMEC differentiation strategy is defined, robust, and facile.

Results

Progression of hPSC Differentiation to BMECs

Given the roles of canonical Wnt signaling in both mesoderm specification and BBB development, we first treated hPSCs with CHIR99021, a GSK-3β inhibitor and Wnt agonist, to direct hPSCs to mesoderm-derived endothelial progenitors. Prior to treatment, IMR90-4 induced pluripotent stem cells (iPSCs) were seeded on a Matrigel-coated six-well plate at a density of $35 \times 10^3$ cells/cm$^2$ and expanded in an undifferentiated state for three days in mTeSR1™ (FIG. 1A). Previously, we showed that 6 µM CHIR99201 treatment induced hPSC differentiation to primitive streak in a serum-free and albumin-free medium [49]. Hence at day 0, 6 µM of CHIR was added into DeSR1 (Unconditioned medium lacking KnockOut Serum Replacement: DMEM/F12, 1% MEM-NEAA, 0.5% GlutaMAX and 0.1 mM β-mercaptoenthanol [32]) to initiate differentiation. After 24 hours, the medium was removed and cells were transitioned to DeSR2 (DeSR1 plus B27 supplement) for another five days with daily medium changes. At day 0, pluripotency was verified by OCT4, NANOG and TRA-1-60 immunostaining (FIGS. 1B-D). After 24 hr of CHIR99021 treatment, almost 100% of the cells expressed brachyury, assessed by immunostaining (FIG. 1E) and flow cytometry (FIG. 1F), indicating progression to primitive streak. In concert with brachyury expression, primitive streak genes T and MIXL1 [50] peaked at day 2 and then dramatically decreased (FIG. 5). At day 4, more than 90% of the cells expressed the intermediate mesoderm marker PAX2 (FIGS. 1G, 1H) and PAX2 expression peaked at day 6 (FIG. 5). Nearly 100% of the cells expressed the endothelial progenitor marker Flk-1 at day 5 (FIGS. 1I, 1J), while the expression level of the endothelial progenitor marker CD31 gradually increased and then diminished after day 6 (FIG. 5).

Figures 5A, 5B, 5C, 5D, 5E, 5F, 5G, 5H, 5I, 5J:
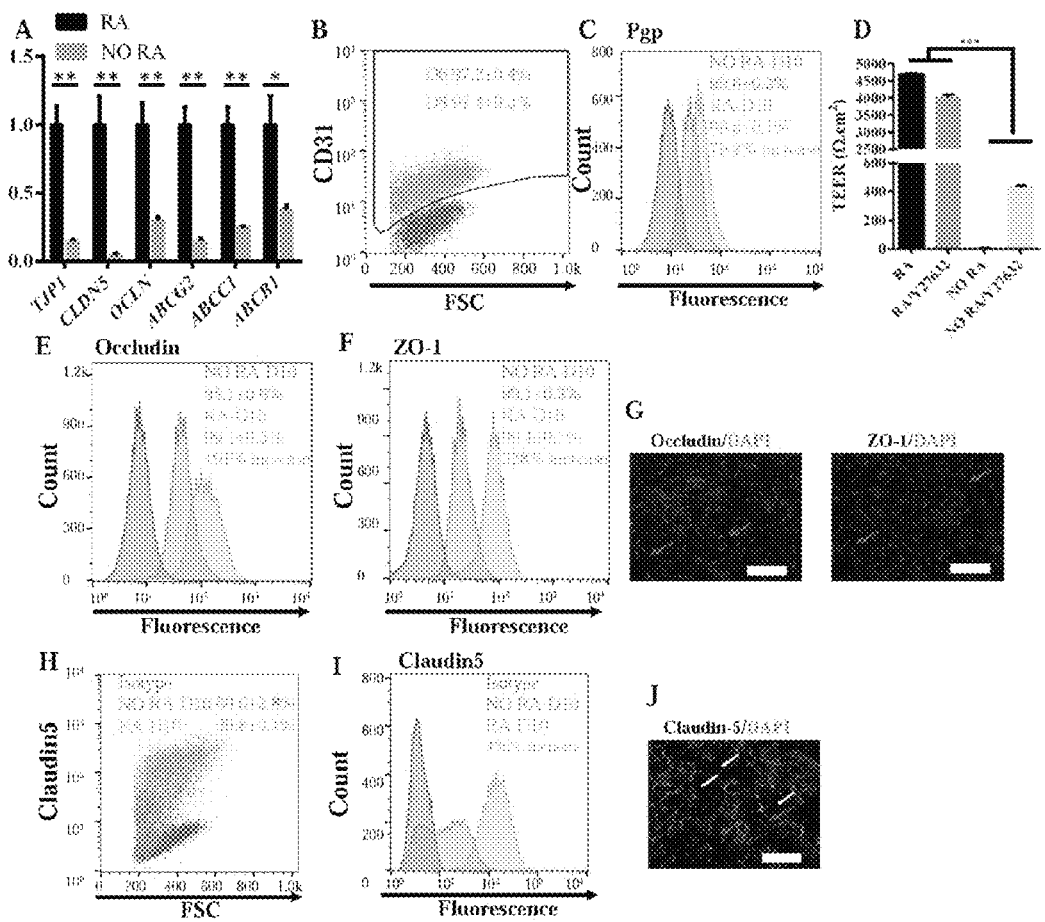
FIGS. 5A-5J demonstrate that retinoic acid (RA) induces acquisition of key BMEC phenotypes in EC progenitors. BMECs were differentiated as shown in FIG. 1A in the presence or absence of RA, as indicated. (A) At day 8 expression of tight junction and transporter genes was assessed by qPCR. (B) Flow cytometry for CD31 expression was performed at days 6 and 8. (C) Pgp expression was quantified by flow cytometry at day 10. At day 6, medium was switched to hESFM containing or lacking RA, as indicated. (D) At day 8, cells were replated onto Matrigel®-coated Transwell® membranes at $10^6$ cells/cm$^2$ in the presence or absence of 10 μM Y27632 (ROCK inhibitor). Y27632 was added to increase attachment (Pipparelli et al., *PloS one* 2013, 8:e62095) of cells differentiated in the absence of RA and permit confluent monolayer formation. TEER was measured at day 10, two days after replating (D). (E, G) Occludin and (F, G) ZO-1 expression and localization were assessed by flow cytometry and immunostaining at day 10. Red arrows indicate non-uniform occludin or ZO-1. Claudin-5 expression at day 10 was assessed by flow cytometry (H, I). (I) At day 10, expression level of claudin-5 in BMECs differentiated in the presence or absence of RA were assessed by flow cytometry. (J) Localization and expression of claudin-5 of cells differentiated in the absence of RA was determined via immunostaining (white arrows indicate non-positive claudin-5 and red arrows indicate discontinuous claudin-5). Images and flow cytometry plots are representative of at least 3 independent experiments. Data from at least three independent replicates are plotted as mean±SEM. *p<0.05, p<0.01, *p<0.001. Scale bar 100 μm.
Figure 6:
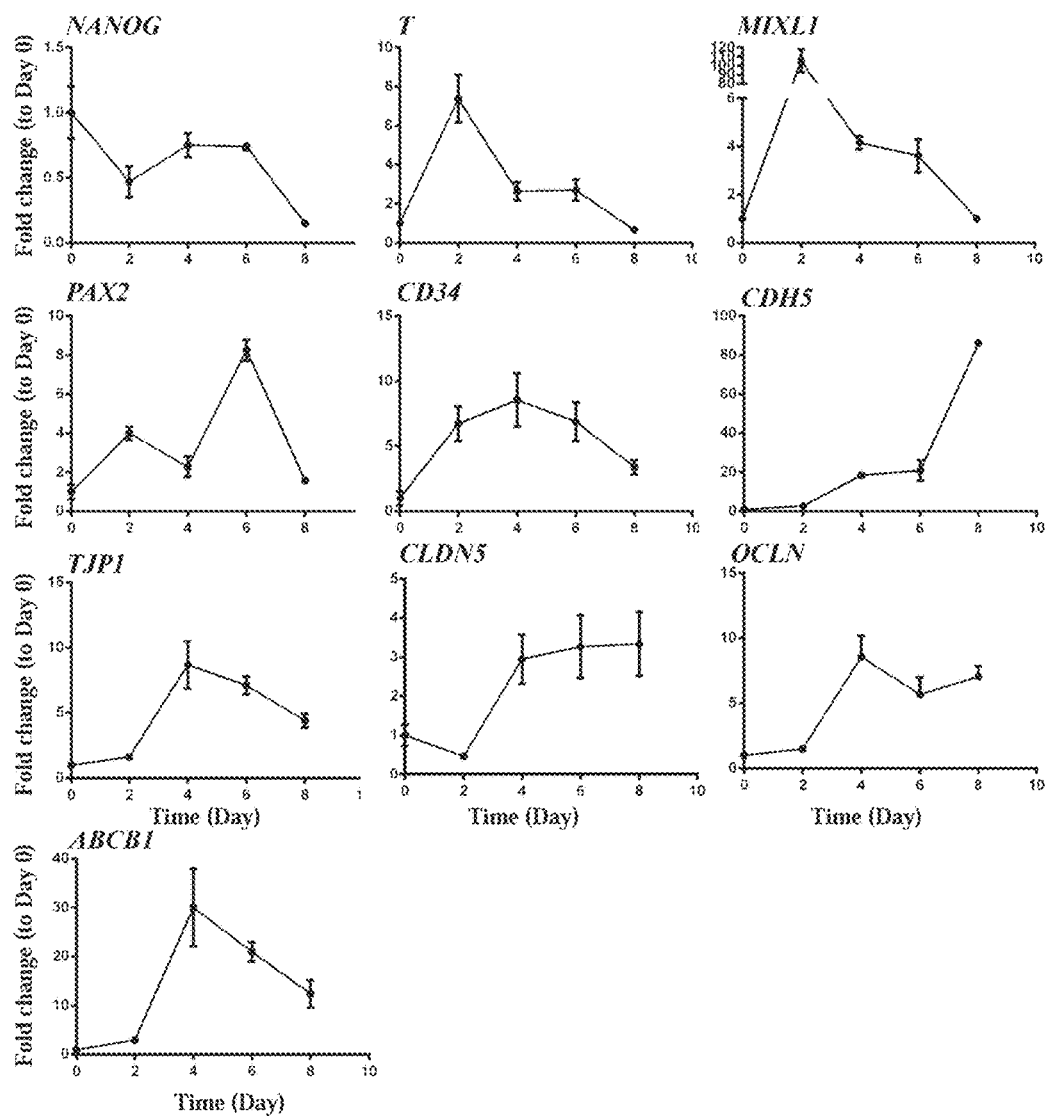
FIG. 6 presents graphs demonstrating gene expression during hPSC differentiation to BMECs. Quantitative RT- PCR was used to quantify the expression of the indicated genes expression during hPSC differentiation to BMECs using the process illustrated in FIG. 1A. Genes analyzed include the pluripotency transcription factor NANOG, primitive streak markers T and MIXL1, intermediate mesoderm marker PAX2, endothelial cell progenitor marker CD34, endothelial adhesion molecule CDH5, tight junction genes TJP1, CLDN5 and OCLN, and efflux transporter ABCB1. GAPDH was used as an endogenous housekeeping gene control. Data are represented as mean±SEM of at least three biological replicates.

At day 6, cells were switched to hECSR1 medium (hESFM supplemented with 20 ng/ml bFGF, 10 µM RA and B27) to induce RA signaling in the hPSC-derived endothelial progenitors in an attempt to drive specification to BMECs. Cells were maintained in this medium for two days. At day 8, cells were replated onto a Matrigel-coated substrate in hECSR1 and at day 9, the medium was switched to hECSR2 (hECSR1 lacking RA and bFGF). Expression of CDH5 (VE-cadherin) was substantially induced after RA treatment (FIG. 5). Expression of tight junction-related genes TJP1, CLDN5 and OCLN and efflux transporter ABCB1 also increased during differentiation (FIG. 5). The resultant day 10 BMEC-like cells were a pure population expressing endothelial markers (CD31, VE-Cadherin), BBB glucose transporter (GLUT-1), tight junction proteins (ZO-1, claudin-5, occludin) and efflux transporters (BCRP, MRP1, Pgp) (FIGS. 2A-2I). Thus, treatment of hPSCs with CHIR99021 and RA directed hPSCs through endothelial progenitors to endothelial cells that expressed BMEC markers. We next tested whether the differentiation protocol illustrated in FIG. 1A generated cells expressing BMEC markers in additional hPSC lines, including H9 human embryonic stem cells (hESCs) and 19-9-11 iPSCs. These lines also produced cells expressing endothelial and BMEC markers, including CD31, Glut1, ZO-1, claudin-5, occludin, MRP1, BCRP1 and Pgp, at day 10 (FIG. 6).

Figures 2A, 2B, 2C, 2D, 2E, 2F, 2G, 2H, 2I, 2J, 2K:
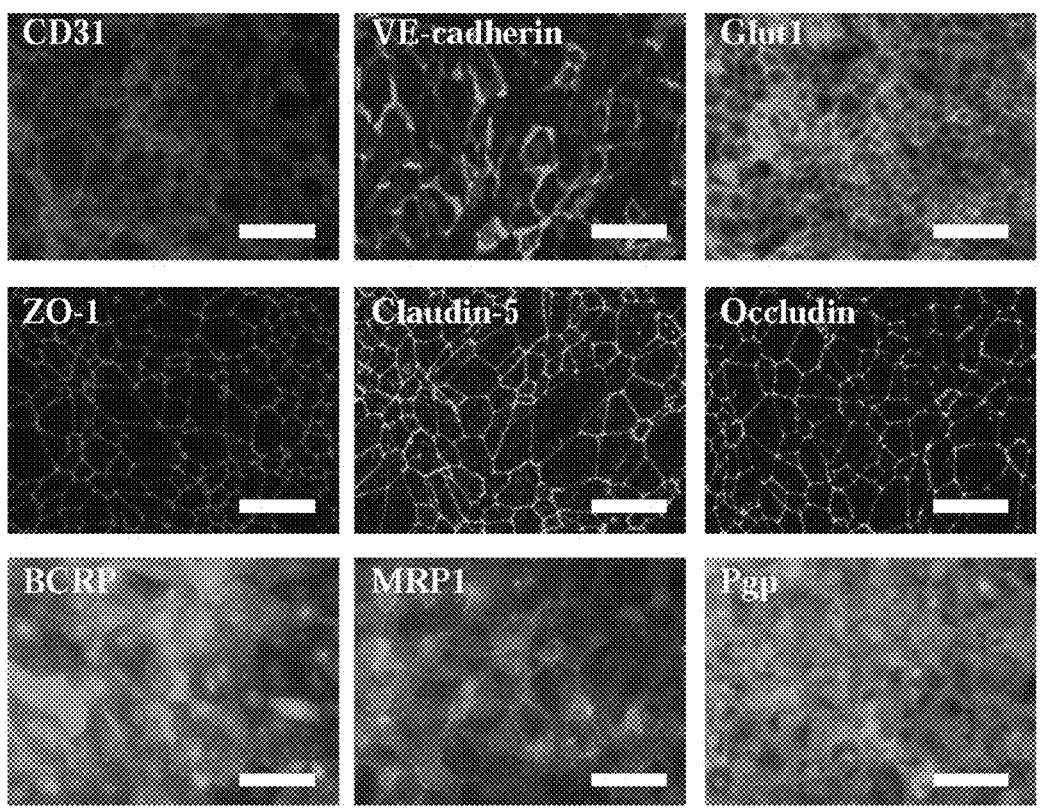
FIGS. 2A-2K present data demonstrating that hPSC-derived BMECs express key BMEC proteins and have similar gene profiles as primary human BMECs. At day 10, BMECs differentiated as shown in FIG. 1A were characterized by (A) immunostaining and (B-I) flow cytometry for key endothelial and BMEC markers. Scale bar, 100 μm. (J) Hierarchical clustering of whole transcripts was plotted using GENE-E. Fastq files of undifferentiated hPSCs and hPSC-derived ectoderm, endoderm, mesoderm were downloaded from GEO or ArrayExpress. Hierarchical clustering analysis of RNA-seq expression data of undifferentiated hPSCs, hPSC-derived endoderm (Endo), ectoderm (Ecto), and mesoderm (Mes), BMECs differentiated under defined conditions as illustrated in FIG. 1A ("D-BMEC1,2,3" refers to three batches of BMECs differentiated using same defined method); IMR90-4-derived BMECs at day 10), BMECs differentiated in unconditioned medium (UM-BMEC), and human primary BMECs (hBMEC). A hierarchical clustering was performed on the log 2 transformed gene counts. Distances were computed using one minus pearson correlation with average linkage. (K) A set of 506 tight junction and transporter genes (see Table 3 in the Examples section) was used to investigate the gene expression similarity between human BMECs, hPSC-derived BMECs differentiated under defined condition, and hPSC-derived BMECs differentiated in unconditioned-medium (UM) [32]. The gene set included: 20 tight junction related genes [1,51-54], all 25 CLDN genes, all 407 solute carrier (SLC) transporters, and all 53 ATP-binding cassette (ABC) transporters. CLDN, SLC and ABC genes were included without a prior knowledge of BBB association. A threshold of >1 FPKMs was used to define expressed vs. non-expressed transcripts.

Next, RNA sequencing was used to compare global gene expression profiles in the hPSC-derived BMECs differentiated as shown in FIG. 1A with BMECs generated from our previously reported co-differentiation system (UM, [32]) and primary human BMECs. As expected, hPSC-derived BMECs from three independent differentiations clustered closely and were similar to those generated from the undefined UM platform. Moreover, the hPSC-derived BMECs clustered with primary human BMECs and were distinct from undifferentiated hPSCs and hPSC-derived ectoderm, endoderm and mesoderm (FIG. 2J). The Pearson correlation analysis was used to evaluate the gene expression similarity between defined-BMECs and primary human BEMCs. The coefficient between defined-BMECs and primary human BMECs is 0.77 (P<0.001), which suggests a strong positive association between these two groups. We next analyzed the expression of a subset of genes that regulate key BBB attributes, including tight junctions and molecular transporters. The gene set comprises 20 tight junction related genes [1,51-54] and an unbiased list of all 25 CLDN genes, all 407 solute carrier (SLC) transporters, and all 53 ATP-binding cassette (ABC) transporters regardless of prior knowledge of BBB association (Table 2). Primary human BMECs expressed 234 of these genes. BMECs differentiated from hPSCs via the defined method expressed many of these same genes (206 of 234 (88%)) as did BMECs differentiated via the UM method (208 of 234 (89%), FIG. 2K), indicating a close similarity between human BMECs from the different sources with respect to transcripts having potential relevance to BBB function.

Figure 7A:
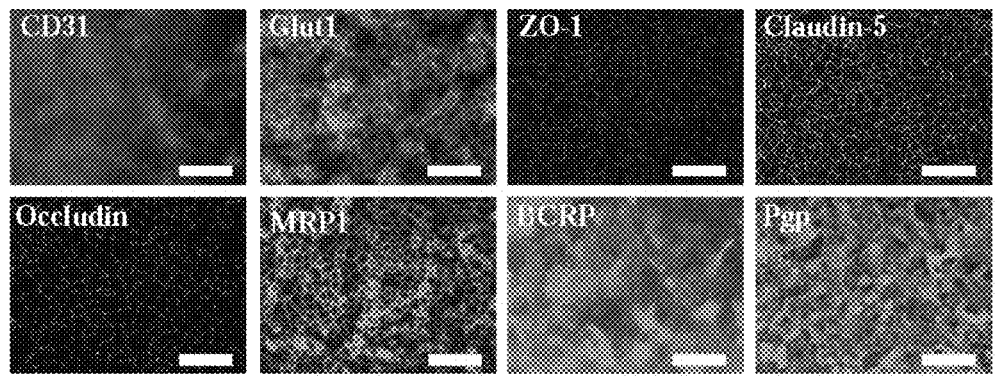
FIGS. 7A-7B are images showing BMECs differentiated from H9 hESCs and 19-9-11 iPSCs express EC and BMEC-related protein. Immunostaining of EC (CD31) and BMEC (Glut1, ZO-1, Claudin-5, occludin, MRP1, BCRP, Pgp) proteins in day 10 BMECs differentiated from (A) H9 hESCs and (B) 19-9-11 iPSCs as shown in FIG. 1A. Images are representative of at least three independent differentiation experiments in each cell line. Scale bar 100 μm.
Figure 7B:
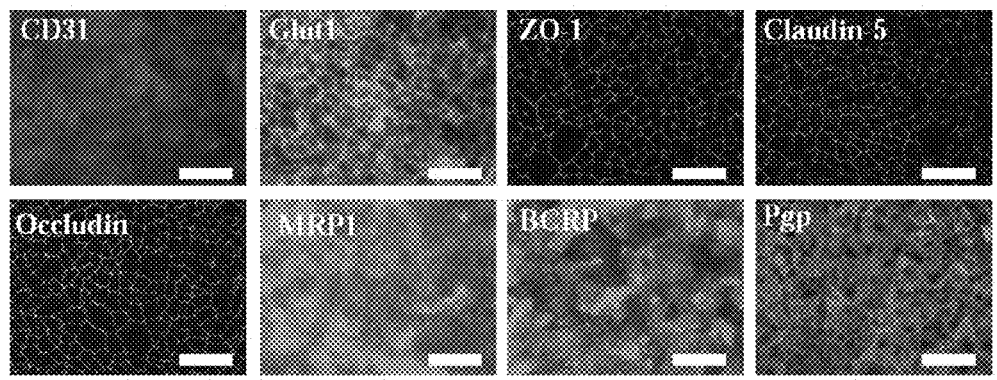

Initially, differentiation was performed on Matrigel®, which has been shown to support BMEC generation from hPSCs [32]. However, to remove the lot-to-lot variability inherent to Matrigel® and to fully define the differentiation platform, we explored differentiation on SyntheMax™ and recombinant human vitronectin coatings. Undifferentiated IMR90-4 iPSCs were expanded on either SyntheMax™ or vitronectin-coated surfaces for 3 days then subjected to the differentiation process shown in FIG. 1A. Cells were replated onto a human placenta-derived collagen IV/human plasma-derived fibronectin-coated surface at day 8. Immunostaining at day 10 demonstrated expression of key BMEC proteins in cells differentiated on defined matrices (FIGS. 7A-7B).

hPSC-Derived BMECs Exhibit BBB Phenotypes

Figures 3A, 3B, 3C, 3D, 3E, 3F, 3G, 3H, 3I, 3J, 3K:
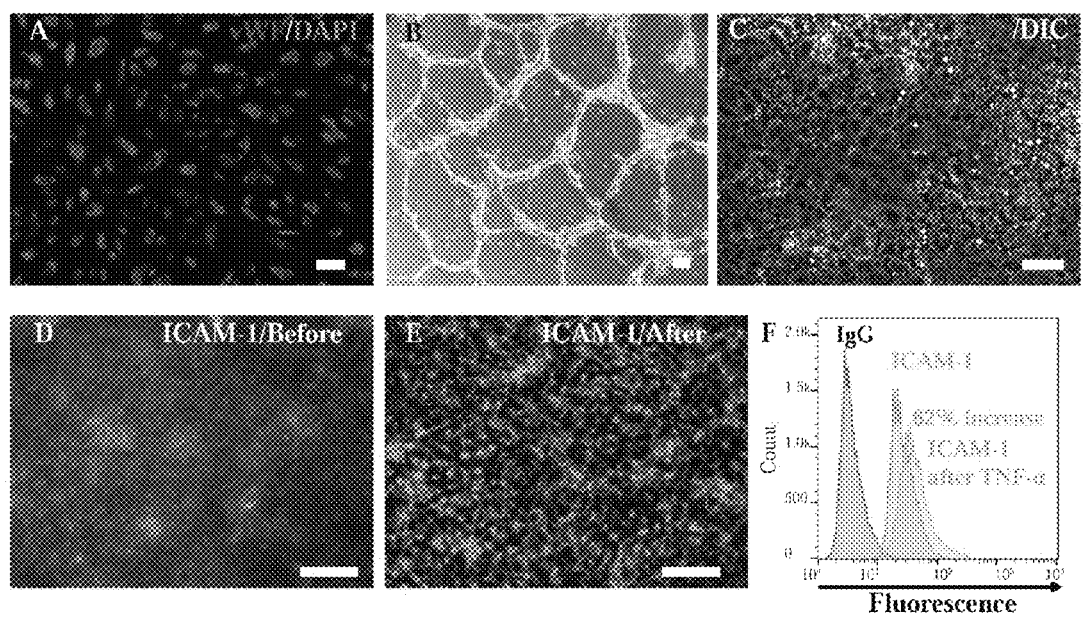
FIGS. 3A-3K demonstrate that hPSC-derived BMECs exhibit key BBB phenotypes. hPSC-derived BMECs were differentiated as illustrated in FIG. 1A. (A) Immunofluorescent images of von Willebrand factor (vWF, red) and DAPI nuclear staining (blue) in hPSC-derived BMECs at day 10. (B) hPSC-derived BMECs were dissociated with Accutase™ and replated $2\times10^5$ cells/well of a 24-well plate coated with 300 μL of 10 mg/L Matrigel®. After 24 hour of culture in hECSR2 supplemented with 50 ng/mL VEGF, brightfield images were taken. (C) hPSC-derived BMECs at day 10 were analyzed with a LDL Uptake Assay Kit. Culture medium was aspirated and replaced with LDL-Dylight™ 550 working solution and visualized by fluorescent microscopy. LDL is shown in red on a merged brightfield image. (D-F) ICAM-1 induction in hPSC-derived BMECs. hPSC-derived BMECs at day 10 were treated with 10 ng/mL of TNF-α for 16 hours. Cells were stained for ICAM-1 (D) before and (E) after TNF-α treatment. (F) Cells were dissociated or dissociated with Accutase™ and ICAM-1 expression quantified by flow cytometry before and after TNF-α treatment. Efflux transporter activities were measured by the intracellular accumulation of (G) rhodamine 123, (H) Hoechst and (I) 2',7'-dichlorofluorescein diacetate (DCFDA) substrates for Pgp, BCRP, and MRP, respectively. CsA, Ko143, and MK571 were used as specific inhibitors of Pgp, BCRP, and MRP, respectively. (J) The polarization of Pgp was measured by rhodamine 123 transport across the BMEC monolayer from the apical side to the basolateral side and a reversed Pgp-transport assay (from the basolateral side to the apical side) was carried out to assess the polarization of Pgp. Inhibitor-treated samples were independently normalized to each respective non-inhibitor-treated control sample. Data were collected at least from three independent samples and are represented as mean±SEM. p<0.01, *p<0.001. (K) TEER was measured in hPSC-derived BMECs co-cultured with astrocytes, neurons, and pericytes. hPSC-derived BMECs were co-cultured with primary human pericytes for 24 hours in hECSR1 medium. Following co-culture with pericytes, BMECs were co-cultured with EZ-sphere derived neurons and astrocytes (1:3) in hECSR2 for the remainder of the experiment. TEER was measured as a function of time following initiation of co-culture. Data were collected from at least three independent replicates and are plotted as mean±SEM. *p<0.05. **p<0.01. Scale bar 100 μm.

In addition to examination of BMEC gene and protein expression, we also evaluated endothelial and BMEC phenotypes. After 8 days of differentiation, cells were replated onto a Matrigel®-coated surface at 1 million cells/cm$^2$ and maintained in hECSR1 medium. At day 9, culture medium was switched to hECSR2. Day 10 hPSC-derived BMECs exhibited endothelial cell properties, including expression of von Willebrand factor (vWF) (FIG. 3A), formation of tube-like structures on Matrigel® in the presence of VEGF (FIG. 3B), uptake of acetylated low-density lipoprotein (LDL) (FIG. 3C), and upregulation of ICAM-1 expression after treatment with TNF-α (FIGS. 3D-3F). BMEC efflux transporter activities were also measured at day 10. Efflux transporter accumulation assays were performed by quantifying intracellular accumulation of fluorescent substrates, including the Pgp substrate rhodamine 123, the MRP-family substrate 2',7'-dichlorofluorescein diacetate (DCFDA) and the BCRP-family substrate Hoechst. In the presence of the transporter-specific inhibitors CsA (Pgp), MK571 (MRP), and Ko143 (BCRP), the intracellular accumulation of fluorescent substrates increased between 150% and 220%, indicating activity of each class of transporters in hPSC-derived BMECs (FIGS. 3G-3I). Next, polarization of Pgp activity was demonstrated by measuring rhodamine 123 flux across the BMEC monolayer in the presence and absence of the Pgp-specific inhibitor cyclosporine A (CsA) and in both the apical to basolateral (A-B) and basolateral to apical (B-A) directions. As shown in FIG. 3J, CsA treatment increased rhodamine 123 transport across the BMEC monolayer by 160% in the A-B direction. In contrast, CsA inhibition resulted in a 23% percent decrease in rhodamine 123 crossing the barrier in the B-A direction (indicated in FIG. 1A), indicating Pgp efflux function polarized in the B-A direction. Finally, BMECs differentiated via the defined protocol exhibited similar Pgp accumulation and transport as BMECs differentiated via our previously reported undefined co-differentiation protocol (FIGS. 7A-7B, UM protocol).

Finally, previous studies have shown that co-culturing BMECs, including those that are iPSC-derived, with neural progenitor cells, astrocytes and pericytes can enhance BBB properties such as TEER [55-59]. Day 8 iPSC-derived BMECs seeded on Transwells were maintained either as a monoculture or co-cultured with primary human pericytes for the first 24 hr followed by co-culture with hPSC EZ-sphere-derived astrocytes and neurons (1:3) [60] for 3 additional days. Maximum TEER was elevated 30% at day 2 and remained elevated throughout the duration of the experiment compared to the monoculture control (FIG. 3K).

Cell Density is Crucial for BMEC Differentiation

Figures 4A, 4B, 4C, 4D, 4E, 4F, 4G, 4H, 4I, 4J:
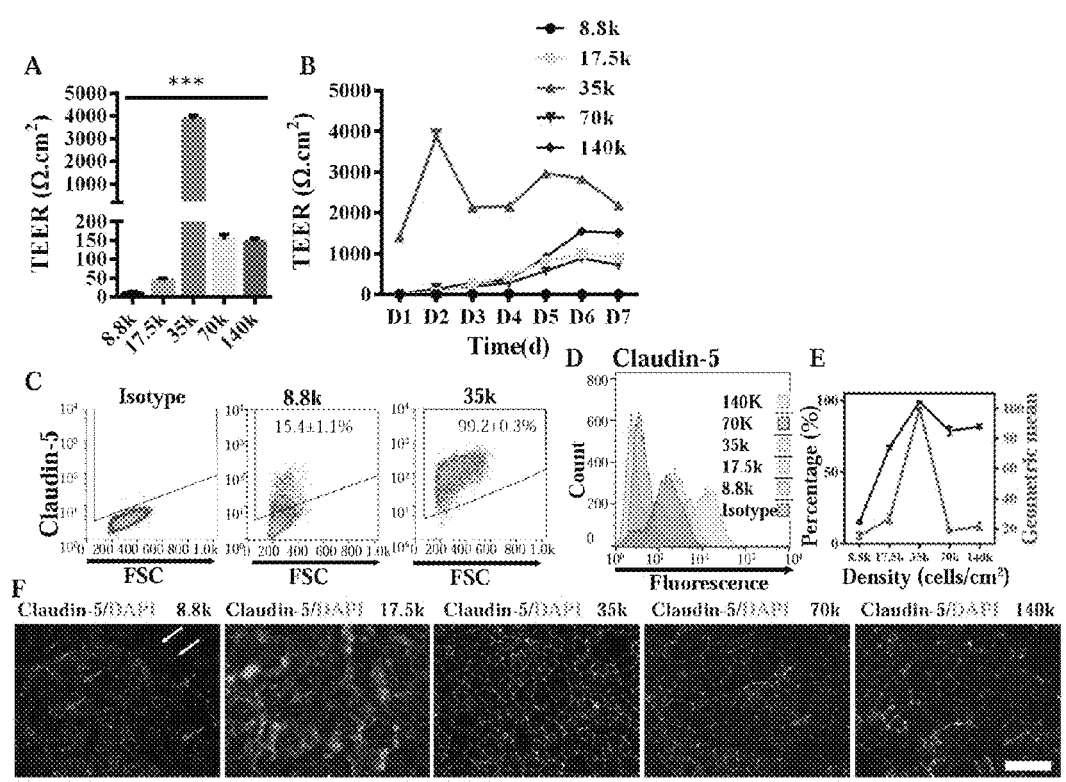
FIGS. 4A-4J demonstrate that initial seeding density is critical for BMEC differentiation. (A) hPSCs were seeded at the indicated densities (from 8.8 k/cm$^2$ to 140 k/cm$^2$) and differentiated to BMECs as illustrated in FIG. 1A. TEER was measured two days after replating on Transwell® membranes at $10^6$ cells/cm$^2$. (B) TEERs of hPSC-derived BMECs were measured daily for 7 days after replating on Transwell® membranes. Data were collected from at least three independent replicates and are plotted as mean±SEM. ***p<0.001. (C-E) The percentage of claudin-5-positive cells and expression levels of claudin-5 were quantified by flow cytometry at day 8 for cells differentiated at the indicated seeding density (cells/cm$^2$). (F) The localization of claudin-5 in cells differentiated at different seeding densities was investigated by immunostaining. White arrows indicate areas lacking claudin-5 expression, and red arrows indicate non-uniform or discontinuous claudin-5. (G-I) The percentage of occludin-positive cells and expression levels of occludin were quantified by flow cytometry at day 8 for cells differentiated at the indicated seeding density (cells/cm$^2$). (J) The localization of occludin in cells differentiated at different seeding densities was investigated by immunostaining. White arrows indicate areas lacking occludin expression and red arrows indicate areas with non-uniform occludin. Flow cytometry plots are representative of at least 3 independent experiments. Numbers indicate the mean fraction of cells in the gated region±SEM. Scale bar 100 μm.
Figure 8A:
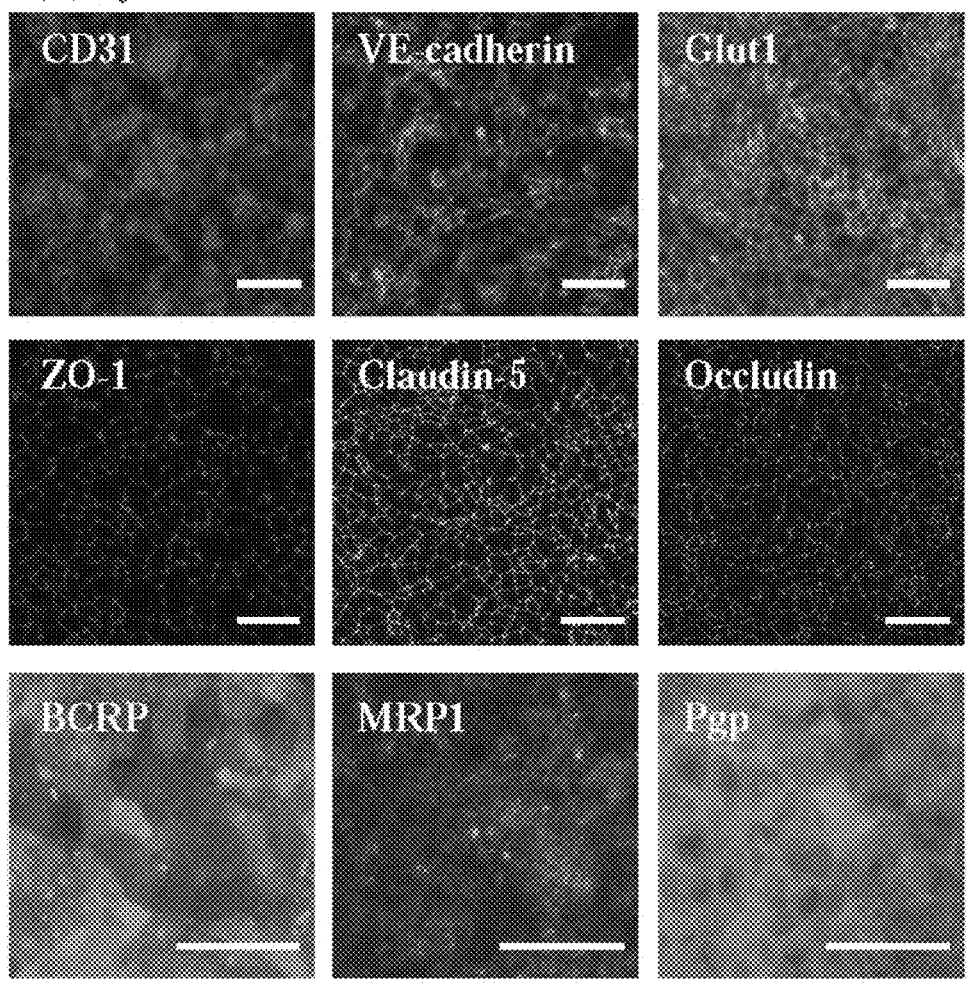
FIGS. 8A-8B are images demonstrating that BMECs differentiated on SyntheMAX™ and vitronectin express EC and BMEC-related proteins. Immunostaining of EC (C31, VE-cadherin) and BMEC (Glut1, ZO-1, Claudin-5, occludin, MRP1, BCRP, Pgp) proteins in day 10 BMECs differentiated as shown in FIG. 1A from IMR90-4 hiPSCs on (A) SyntheMAX™ and (B) vitronectin. Images are representative of at least three independent differentiation experiments on each matrix. Scale bar 100 μm.
Figure 8B:
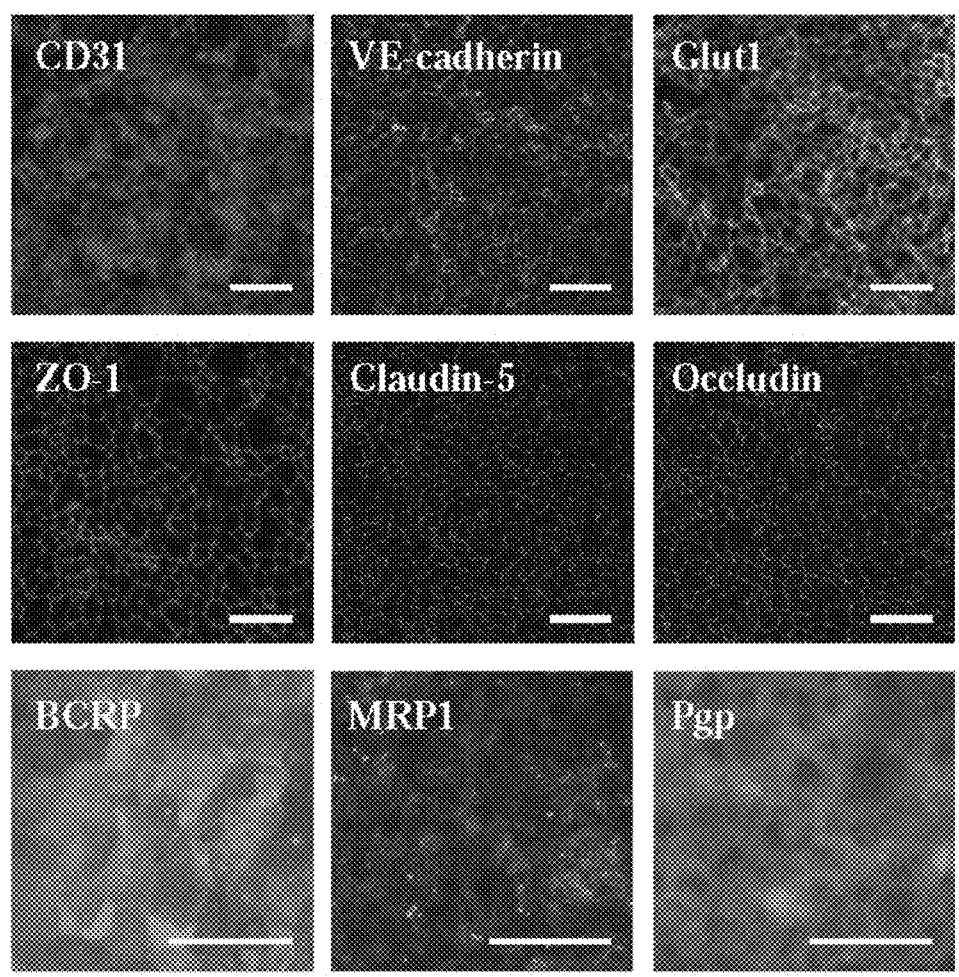
Figure 9:
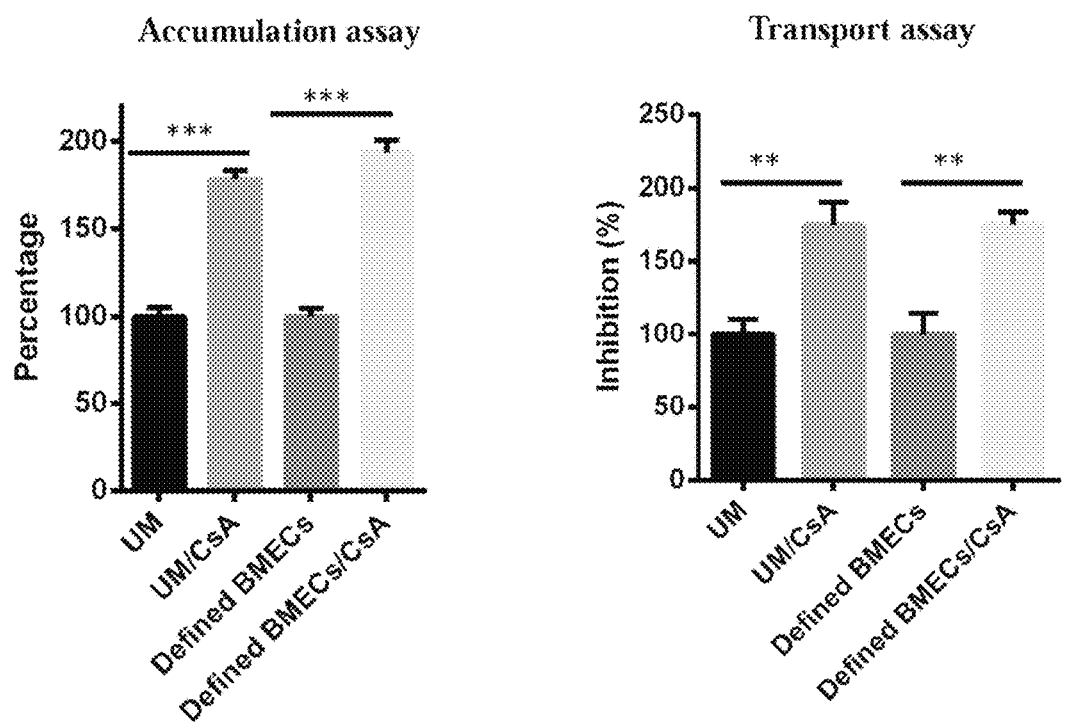
FIG. 9 demonstrates that BMECs differentiated from hPSCs in defined and undefined protocols exhibit similar Pgp activities. hPSC-derived BMECs were differentiated either as illustrated in FIG. 1A (defined BMECs) or as described previously (UM (Wilson et al., *Fluids and Barriers of the CNS* 2015, 12:13)). Pgp activities were evaluated by the intracellular accumulation of rhodamine 123 (left bar graph) or rhodamine 123 transport across the BMEC monolayer from the apical side to the basolateral side (right bar graph). Data were collected from at least three biological replicates for each group and are presented as mean±SEM. $p<0.01$; *$p<0.001$.
Figure 10:
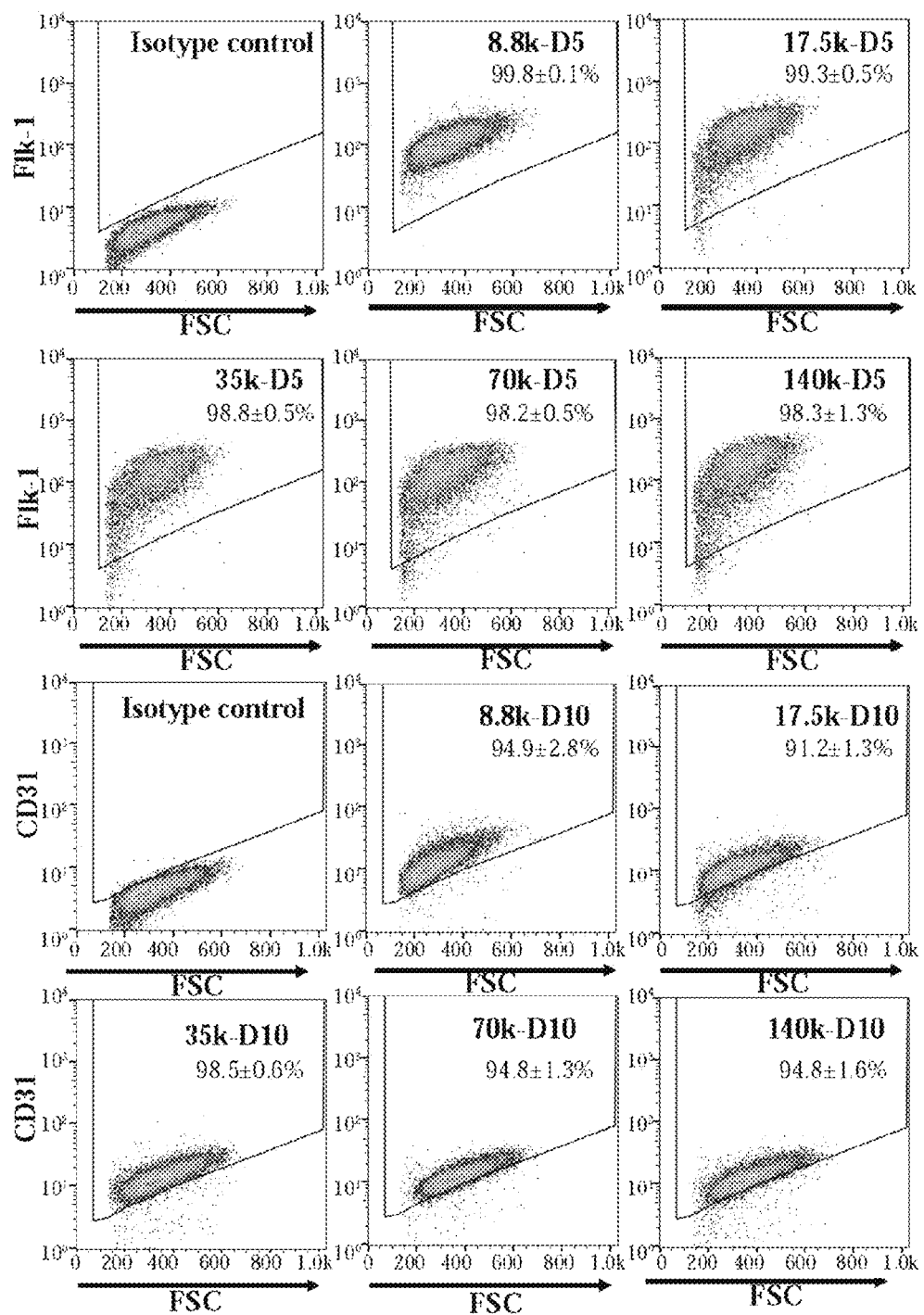
FIG. 10 demonstrates that BMECs differentiated at different seeding densities express Flk-1 and CD31. Flow cytometry was used to quantify the Flk1-positive (Flk1+) population at day 5 and the CD31-positive population at day 10 in hPSC-derived BMECs differentiated as shown in FIG. 1A. hPSCs were plated at the indicated density from 8.8 k cells/cm² to 140 k cells/cm² at day −3. Plots are representative of at least three replicates, for which mean±SEM are indicated in each plot.
Figure 11:
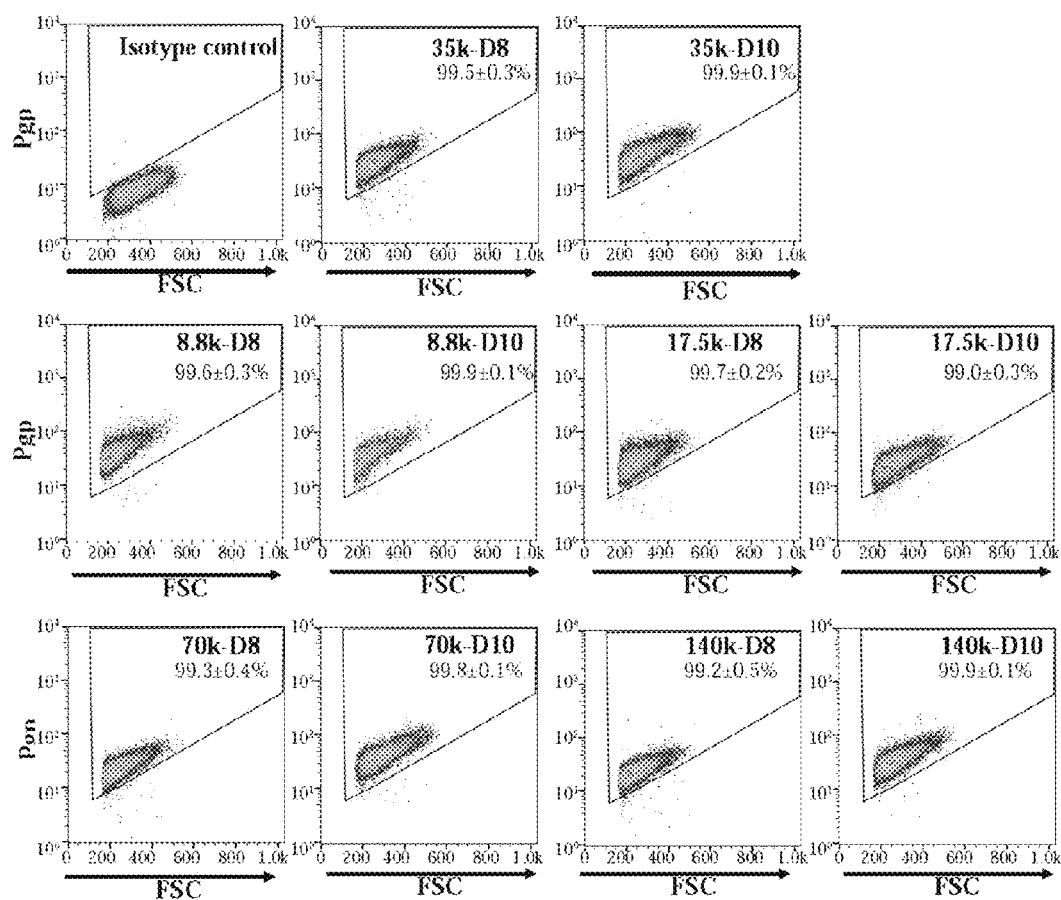
FIG. 11 demonstrate that BMECs differentiated at different seeding densities express Pgp. Flow cytometry was used to quantify the Pgp-positive population at days 8 and 10 in hPSC-derived BMECs differentiated as shown in FIG. 1A. hPSCs were plated at the indicated density from 8.8 k cells/cm² to 140 k cells/cm² at day −3. Plots are representative of at least three replicates, for which mean±SEM are indicated in each plot.
Figures 12A, 12B:
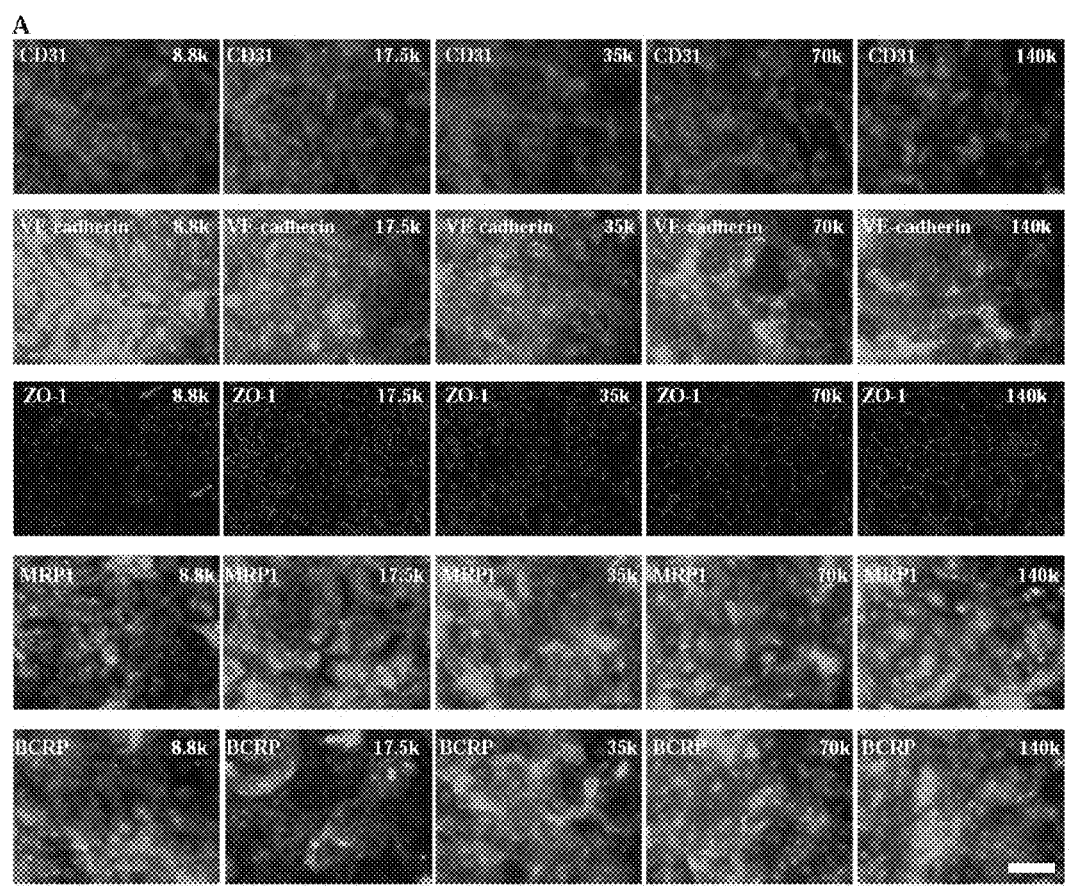
FIGS. 12A-12B demonstrate that BMECs differentiated at different seeding densities express related BMEC proteins, but the BMEC proteins are not nicely localized. IMR90-4 hiPSCs were differentiated to BMECs at the indicated day −3 seeding densities (cells/cm²) on Matrigel® using the protocol shown in FIG. 1A. (A) Immunofluorescent images for EC (CD31, VE-cadherin) and BMEC (ZO-1, MRP1, BCRP) markers were acquired at day 10. Scale bar, 100 μm. (B) The percentage of ZO-1-positive cells at days 8 and day 10 was quantified by flow cytometry. Images and flow cytometry plots are representative of at least three independent replicates. Data were collected at least from three replicates for each group and presented as mean±SEM.

Cell density has been shown to be crucial for efficient hPSC differentiation to a variety of lineages, including BMECs [61-64]. Thus, in addition to the optimal initial day −3 cell seeding density employed above ($35 \times 10^3$ cells/cm$^2$), we tested a range of seeding densities, from $8.8 \times 10^3$ cells/cm$^2$ to $140 \times 10^3$ cells/cm$^2$, to explore how density affects BMEC yield and phenotype. As shown in FIG. 4A, TEER was a strong function of seeding density, with only $35 \times 10^3$ cells/cm$^2$ yielding BMECs possessing substantial barrier function at day 2 after transfer onto Transwells. The BMEC TEER peaked at 2 days after replating and plateaued above 2000 $\Omega \cdot cm^2$ through day 7 (FIG. 4B). At non-optimum seeding densities, TEER gradually increased through 6 days after replating, peaking at approximately 1000 $\Omega \cdot cm^2$. We next assessed expression of endothelial markers to investigate the endothelial specification process. Cells differentiated at all densities tested yielded endothelial cell populations with nearly 100% Flk-1 positive cells at day 5 and over 90% CD31 positive cells at day 10 (FIG. 8). This suggested that deficits in barrier function may be a result of poor BMEC specification. Thus, we assessed BMEC markers in populations differentiated at different seeding densities. Nearly 100% of cells expressed Pgp after the differentiation process at either Day 8 or Day 10 (FIG. 9). However, only cells differentiated at the optimal seeding density of $35 \times 10^3$ cells/cm$^2$ yielded a pure claudin-5 expressing population with maximal claudin-5 expression (FIGS. 4C-4E). In addition to cells not expressing claudin-5, cells differentiated from non-optimal starting densities also displayed non-junctional claudin-5 (FIG. 4F, white arrows) or non-uniform claudin-5 distributions at cell junctions (FIG. 4F, red arrows). In addition, only cells differentiated from seeding densities of at least $35 \times 10^3$ cells/cm$^2$ yielded a nearly pure population of occludin-expressing cells (FIGS. 4G-4I). Immunostaining analysis of occludin also showed cells differentiated from cell densities less than $35 \times 10^3$ cells/cm$^2$ had large areas of cells lacking occludin expression (FIG. 4J, white arrows). Unlike Claudin-5 and occludin, seeding density did not have a significant effect on ZO-1 expression, but cells differentiated with $8.8 \times 10^3$ cells/cm$^2$ showed poor ZO-1 localization (FIG. 10, red arrows). Immunostaining for additional BMEC markers also indicated poor localization of CD31, ZO-1, MRP1 and BCRP in cells differentiated at non-optimum cell density (FIG. 10, compare 35 k to other densities). H9 hESCs and 19-9-11 iPSCs differentiated at an initial seeding density of $35 \times 10^3$ cells/cm$^2$ also generated BMECs TEER at or above 2000 $\Omega \cdot cm^2$ (FIG. 11). In addition, $35 \times 10^3$ cells/cm$^2$ was found to be the optimal seeding density for SyntheMax™ and vitronectin substrates, with vitronectin substrates performing more closely to Matrigel® than SyntheMax™ substrates in TEER assays (FIG. 12).

RA Enhances BMEC Phenotypes

Figure 13:
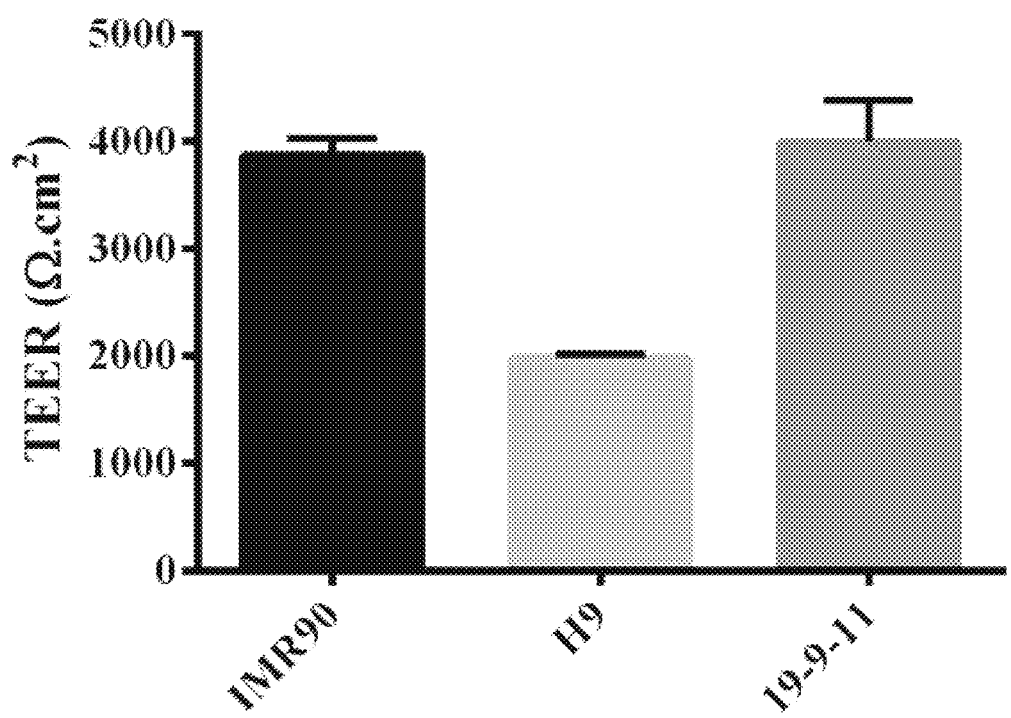
FIG. 13 presents TEER of BMECs differentiated from different hPSC lines. Different hPSC lines, including IMR90-4, H9, 19-9-11 hPSCs, were seeded at a density of 35 k cells/cm² and differentiated to BMECs as illustrated in FIG. 1A. TEER was measured two days after replating on Transwell® membranes at 10⁶ cells/cm². Data were collected at least from three biological replicates for each group and presented as mean±SEM.
Figure 14:
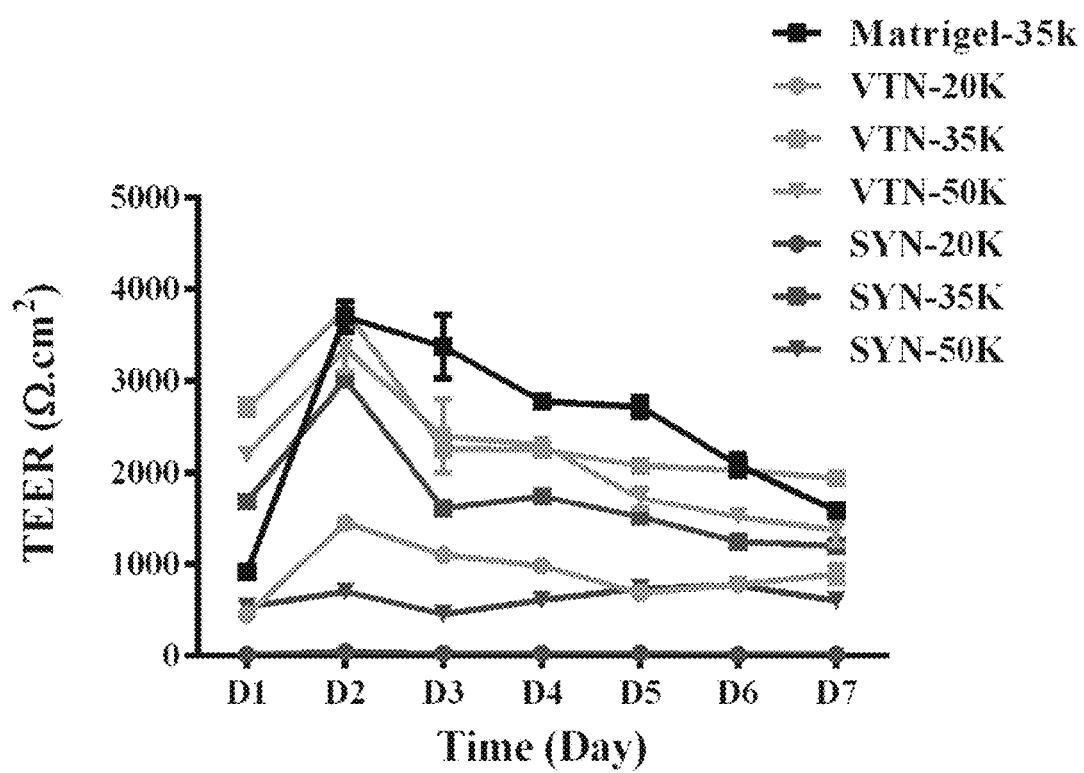
FIG. 14 presents TEER in BMECs differentiated from hPSCs at different seeding densities. IMR90 iPSCs were differentiated to BMECs via the protocol illustrated in FIG. 1A at the indicated day −3 seeding density (cells/cm2) on vitronectin ("VTN"), SyntheMAX™ ("SYN"), or Matrigel®. TEER was measured daily after seeding cells on Transwell® filters (Day 0). Data represent mean±SEM of at least three biological replicates.
Figure 15:
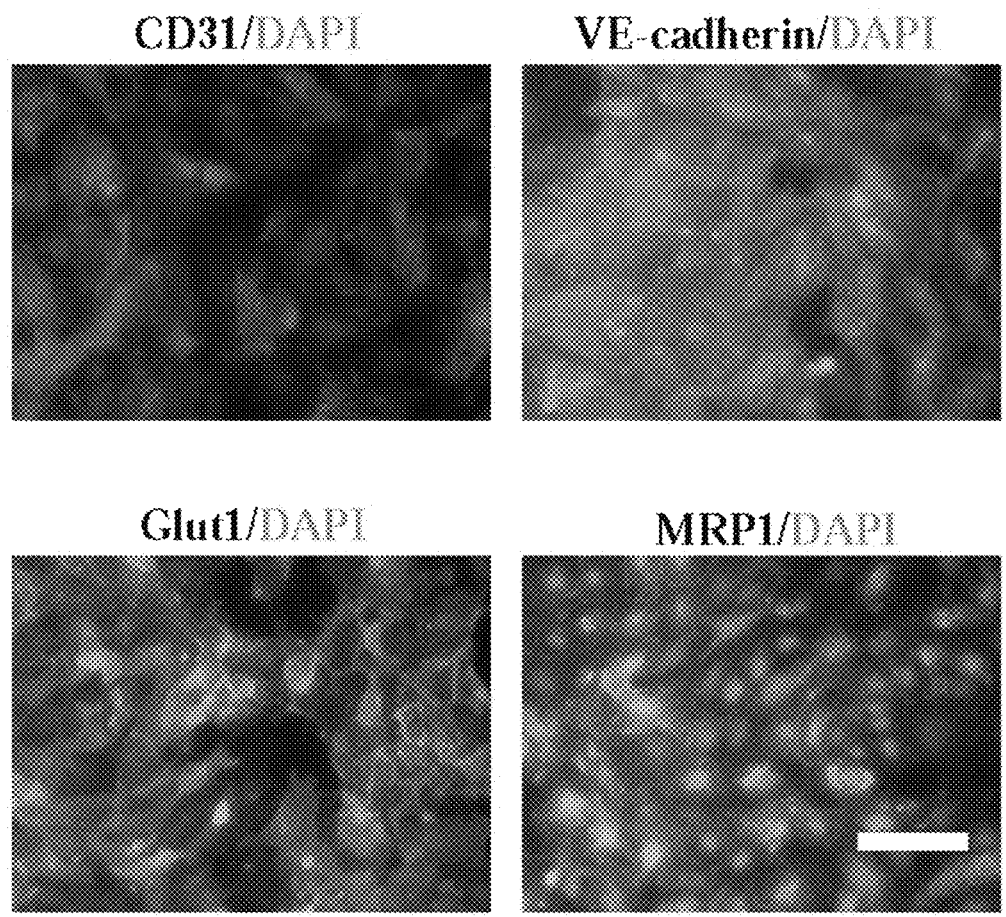
FIG. 15 demonstrates that BMECs differentiated in the absence of RA exhibit low expression and mislocalization of EC and BMEC proteins. The images demonstrate immunostaining of markers of EC (CD31, VE-cadherin) and BMEC (Glut1, MRP1) in BMECs differentiated as shown in FIG. 1A from IMR90-4 iPSCs, but differentiated in the absence of RA from day 6 to day 9. Images were taken at day 10 and are representative of at least three biological replicates. Scale bar 100 μm.

Previously, we have shown that RA induces BBB properties in hPSC-derived BMECs [33]. Other studies also have demonstrated that RA signaling regulates BBB formation and induces BBB phenotypes [44,45]. To determine the role of RA in specifying BMEC differentiation and enhancing the BMEC phenotypes described in FIGS. 2A-2K and FIGS. 3A-3K, we compared differentiation in the presence and absence of RA using the protocol illustrated in FIG. 1A. From day 6 to day 8, cells were maintained either in hECSR1 or hECSR1 lacking RA. qPCR showed that expression of tight junction related genes TJP1, CLDN5 and OCLN and efflux transporters ABCG2, ABCC1, and ABCB1 was greater (3-20-fold) in cells exposed to RA (FIG. 5A). Nearly 100% of cells expressed CD31 at day 6 and this expression was preserved in the presence of RA induction at day 8 (FIG. 5B). Immunofluorescence for CD31 and other BMEC markers for cells differentiated in the absence of RA, including VE-cadherin, Glut1 and MRP1 are shown in FIG. 13. Nearly 100% of cells differentiated in the absence and presence of RA expressed Pgp, but RA-treated cells expressed more Pgp than non-treated cells (FIG. 5C). To evaluate the barrier formation potential of the differentiated BMECs and to assess the effects of RA treatment, day 8 BMECs were replated onto Transwells and TEER measured at day 10. As shown in FIG. 5D, cells differentiated in the presence of RA exhibited physiologically relevant TEER (~4000 $\Omega \cdot cm^2$), while cells differentiated in the absence of RA exhibited significantly reduced barrier properties. We then investigated expression and localization of tight junction proteins. Both occludin and ZO-1 were expressed in nearly all cells at day 10 regardless of RA treatment; however, RA treatment significantly increased the expression levels of occludin and ZO-1 (FIGS. 5E, 5F). Although occludin and ZO-1 expression were lower in the absence of RA, immunostaining results indicate that nearly all the cells differentiated in the absence of RA still expressed occludin and ZO-1; however, the junctional distribution was non-uniform (FIG. 5G, indicated with red arrows and compare to FIG. 2A). In contrast to the results with occludin and ZO-1, in the absence of RA, only around 60% of the endothelial cells expressed claudin-5 compared to 100% of RA-treated cells expressing claudin-5 (FIGS. 5H, 5I). In addition, claudin-5 expression was also substantially greater in RA-treated cells (FIG. 5I). Immunostaining indicated that in the absence of RA, many of the cells did not express claudin-5 (FIG. 5J, white arrows) and those that did exhibited non-uniform junctional distribution of claudin-5 similar to that observed with occludin and ZO-1 (FIG. 5J, red arrows). Taken together, these results suggest that RA is not necessary for hPSC differentiation to endothelial cells but enhances key BMEC phenotypes in the hPSC-derived ECs, including the expression and localization of tight junction proteins that promote barrier function as measured by TEER.

Discussion

In this study, we demonstrate a robust and efficient process to differentiate hPSCs to BMECs in a defined manner. The cells progress as a homogeneous population from a pluripotent state through primitive streak, intermediate mesoderm, endothelial progenitors and eventually to endothelial cells that express many BMEC markers and exhibit BBB barrier and efflux transporter properties. More importantly, this differentiation method employs a completely defined platform, including culture medium and substrates. Defined reagents exhibit less lot-to-lot variability, leading to more robust and efficient differentiation and allowing differentiation results to be more reliable, repeatable and efficient. We have tested three different hPSC lines with this differentiation protocol and all these lines were able to differentiate into pure populations of BMEC with definitive BMEC properties at various cell densities.

In vivo, endothelial cells that form the BBB originate from mesoderm progenitors located outside the CNS [65]. In contrast to previous BMEC differentiation protocols [32,36] that rely on co-culture of endothelial progenitors with pericytes, astrocytes or differentiating neural cells, this differentiation strategy instead relies on sequential Wnt and RA signaling activation to first specify endothelial cells and then enhance BMEC properties, respectively. First, activation of canonical Wnt signaling by CHIR99201 addition directs hPSCs to Brachyury-positive primitive streak cells that then differentiate to PAX2-positive intermediate mesoderm and EC progenitors when cultured at the appropriate density in DeSR2 medium. Next, RA treatment for two days helps drive these endothelial progenitor cells to express key BMEC markers and exhibit BMEC-specific properties, including high TEER and efflux transporter activity. Our experiments showed that while RA was not necessary to obtain ECs, RA treatment significantly increased BBB properties such as TEER. The TEER enhancement correlated with increased expression and improved localization of tight junction proteins occludin and claudin-5. These findings are similar to those results observed after RA treatment of hPSC-derived BMECs generated by co-differentiation with neural cells using our previously reported protocol [33], in addition to those studies that have explored the barrier enhancing effects of astrocyte or neuron co-culture with hPSC-derived BMECs [58,59].

Previously, we have shown cell seeding density can affect BMEC differentiation from hPSCs using the neural co-differentiation protocol [64]. Other studies have also demonstrated a major role for cell seeding density in the hPSC differentiation [66-68]. An initial cell seeding density of about $35 \times 10^3$ cells/$cm^2$ at day −3 is necessary to yield homogeneous populations of BMECs with high expression and proper localization of key BBB proteins, in turn leading to optimal barrier properties. In addition, this optimum seeding density translated to multiple hPSC lines and to differentiation on defined matrices. Interestingly, cells differentiated at non-optimal seeding densities expressed BMEC markers but exhibited a reduced TEER, likely resulting from diminished claudin-5 and occludin expression and improper junctional localization. Thus, RA signaling and cell density similarly regulate the capability for the endothelial progenitors to gain BMEC properties and this interplay is a target for future study.

Co-culturing hPSC-derived BMECs with pericytes, astrocytes and neurons further elevated TEER, consistent with previous studies that showed co-culturing BMECs with these neural cells can enhance BBB properties [55,56,69-71]. These data suggest that it will be possible to integrate these defined hPSC-derived BMECs with other cells of the neurovascular unit to create an isogenic patient-derived model which can be used to study the role of neurovascular unit in human neurological diseases [59]. Additionally, this method has the potential to be a powerful and robust tool for pre-clinical studies of pharmaceutical transport through the BBB.

Methods and Materials hPSC Culture and Differentiation:

hiPSCs (iPS(IMR90)-4 and iPS-DF 19-9-11T (Yu et al., *Science* 2007, 318:1917-1920)), hESCs (H9) (Thomson et al., *Science* 1998, 282:1145-1147) were maintained on Matrigel® (Corning)-coated surfaces in mTeSR1™ (STEMCELL Technologies) as previously described (Ludwig et al., *Nature methods* 2006, 3:637-646). Before differentiation, hPSCs were singularized with Accutase™ (Innovative Cell Technologies) and plated onto Matrigel®-coated plates at the density between $4 \times 10^4$ cells/$cm^2$ and $7 \times 10^4$ cells/$cm^2$ supplemented with 10 µM ROCK inhibitor Y-27632 (Selleckchem) in mTeSR1™. hPSCs were maintained in mTeSR1™ for three days. To initiate differentiation at day 0, cells were treated with 6 µM CHIR 99021 (Selleckchem) in DMEM/F12 based serum free medium 1 (DeSR1): DMEM/Ham's F12 (ThermoFisher), 100×MEM nonessential amino acids (ThermoFisher), 100× GlutaMAX (ThermoFisher), and 0.1 mM β-mercaptoethanol (Sigma). After 24 hours, medium was changed to DMEM/F12 based serum free medium 2 ("DeSR2" which is DeSR1 plus B27 Supplement (50×) (ThermoFisher)) every day for another five days. At day 6, medium was switched to hECSR1: human Endothelial Serum-Free Medium (hESFM) (ThermoFisher) supplemented with 20 ng/ml bFGF, 10 µM retinoic acid (RA), and B27 Supplement (50×) (ThermoFisher). After 2 days of culture in hECSR1 medium, day 8 cells were dissociated with Accutase™ and plated at $1 \times 10^6$ cells/$cm^2$ in hECSR1 onto 48-well tissue culture plates or 1.12 $cm^2$ Transwell®-Clear permeable inserts (0.4 µm pore size) coated with 100 µg/ml Matrigel®. At day 10, medium was changed to hECSR2 (hECSR1 without RA or bFGF) for longer term maintenance.

Immunochemistry:

Cells were rinsed with ice-cold phosphate buffered saline (PBS) once and followed by fixation either with ice-cold methanol or 4% paraformaldehyde (PFA) for 15 minutes. Cells were then blocked with 10% goat serum presented with 0.3% Triton-X 100 in PBS for 30 min ("10% PBSGT"). Primary antibodies were incubated with 10% PBSGT either at 4° C. overnight or at room temperature for 2 hours. After three PBS washes, cells were incubated with secondary antibodies in 10% PBGST (goat anti-rabbit Alexa Fluor® 594 and goat anti-mouse Alexa Fluor® 488; 1:200) for 1 hour at room temperature. Cells were then washed with PBS three times followed by nuclei labelling with anti-photobleaching medium DAPI fluoromount-G (Southern Biotech) and visualized.

Flow Cytometry:

Cells were dissociated with Accutase™ and fixed in 1% PFA for 15 min at room temperature, then washed with 0.5% BSA (Bio-Rad) plus 0.1% Triton-X100 three times. Cells were stained with primary and secondary antibodies diluted in 0.5% BSA plus 0.1% Triton-X 100 as described (Lian et al., *Proceedings of the National Academy of Sciences* 2012, 109:E1848-E1857). Data were collected on a FACSCaliber flow cytometer (Beckton Dickinson) and analyzed using FlowJo. Corresponding isotype antibodies were used as FACS gating control. Antibodies used in this study are listed in Table 2.

Quantitative RT-PCR:

Total RNA was extracted with the RNeasy mini kit (QIAGEN) and treated with DNase (QIAGEN). 1 µg total RNA was reverse transcribed into cDNA via Oligo (dT) with Superscript III Reverse Transcriptase (Invitrogen). Real-time quantitative PCR was done in triplicate with iQSYBR Green™ SuperMix (Bio-Rad). GAPDH was used as an endogenous housekeeping control. All the primers were validated and primer sequences are provided in Table 1.

TABLE 1

Primer Sequences

| Gene name | | Primer length | Product length | SEQ ID NO: |
|---|---|---|---|---|
| GAPDH | | | 207 | |
| Forward | CTGATTTGGTCGTATTGGGC | 20 | | 1 |
| Reverse | TGGAAGATGGTGATGGGATT | 20 | | 2 |
| SLC2A1 | | | 140 | |
| Forward | AACTCTTCAGCCAGGGTCCAC | 21 | | 3 |
| Reverse | CACAGTGAAGATGATGAAGAC | 21 | | 4 |
| ABCB1 | | | 207 | |
| Forward | CTCATCGTTTGTCTACAGTTCG | 22 | | 5 |
| Reverse | AAGACATTTCCAAGGCATCA | 20 | | 6 |
| PECAM1 | | | 117 | |
| Forward | GAGTATTACTGCACAGCCTTCA | 22 | | 7 |
| Reverse | AACCACTGCAATAAGTCCTTTC | 22 | | 8 |
| OCLN | | | 132 | |
| Forward | GACTTCAGGCAGCCTCGTTAC | 21 | | 9 |
| Reverse | GCCAGTTGTGTAGTCTGTCTCA | 22 | | 10 |
| CLDN5 | | | 238 | |
| Forward | GTTCGCCAACATTGTCGTCC | 20 | | 11 |
| Reverse | GTAGTTCTTCTTGTCGTAGTCGC | 23 | | 12 |
| TJP1 | | | 128 | |
| Forward | ACCAGTAAGTCGTCCTGATCC | 21 | | 13 |
| Reverse | TCGGCCAAATCTTCTCACTCC | 21 | | 14 |
| CDH5 | | | 179 | |
| Forward | AAGCGTGAGTCGCAAGAATG | 20 | | 15 |
| Reverse | TCTCCAGGTTTTCGCCAGTG | 20 | | 16 |
| KDR | | | 124 | |
| Forward | GTGATCGGAAATGACACTGGAG | 22 | | 17 |
| Reverse | CATGTTGGTCACTAACAGAAGCA | 23 | | 18 |
| CD34 | | | 185 | |
| Forward | CTACAACACCTAGTACCCTTGGA | 23 | | 19 |
| Reverse | GGTGAACACTGTGCTGATTACA | 22 | | 20 |
| OCT4 | | | 120 | |
| Forward | GTGGAGGAAGCTGACAACAA | 20 | | 21 |
| Reverse | ATTCTCCAGGTTGCCTCTCA | 20 | | 22 |
| Nanog | | | 116 | |
| Forward | TTTGTGGGCCTGAAGAAAACT | 21 | | 23 |
| Reverse | AGGGCTGTCCTGAATAAGCAG | 21 | | 24 |
| Brachyury | | | 143 | |
| Forward | GGGAGCGAGGAGGAAGGGAA | 20 | | 25 |
| Reverse | TGGTGACGGTGCTGAAGTGC | 20 | | 26 |
| MIXL1 | | | 130 | |
| Forward | GGCGTCAGAGTGGGAAATCC | 20 | | 27 |
| Reverse | GGCAGGCAGTTCACATCTACC | 21 | | 28 |
| PAX2 | | | 92 | |
| Forward | TCAAGTCGAGTCTATCTGCATCC | 23 | | 29 |
| Reverse | CATGTCACGACCAGTCACAAC | 21 | | 30 |

TABLE 2

Antibodies Used in This Study

| Antibody | Vendor | Cat. NO. | Fixation | Dilution | Buffer |
| --- | --- | --- | --- | --- | --- |
| Brachyury | R&D | AF2085 | 4% PFA | 1:100 IF | 1% BSA |
| PAX2 | Santa Cruz | sc-377181 | 4% PFA | 1:200 IF | 10% PBSG |
| CD31 | ThermoFisher | RB-10333-P1 | MeOH | 1:25 IF | 10% PBSG |
| VE-cadherin | Santa Cruz | BV9 | MeOH | 1:50 IF | 10% PBSG |
| vWF | Dako | A008202-5 | 4% PFA | 1:500 IF | 10% PBSG |
| KDR | Santa Cruz | sc-6251 | 4% PFA | 1:200 IF | 10% PBSG |
| Claudin5 | Invitrogen | 4C3C2 | MeOH | 1:200 IF | 10% PBSG |
| Occludin | Invitrogen | OC-3F10 | MeOH | 1:50 IF | 10% PBSG |
| ZO-1 | Invitrogen | 402200 | MeOH | 1:200 IF | 10% PBSG |
| GLUT1 | Thermo | SPM498 | MeOH | 1:100 IF | 10% PBSG |
| PGP | ThermoFisher | p170 (F4) | MeOH | 1:25 IF | 10% PBSG |
| BCRP | Millipore | MAB4155 | 4% PFA | 1:25 IF | 10% PBSG |
| MRP1 | Millipore | MAB4100 | MeOH | 1:50 IF | 10% PBSG |
| OCT3/4 | Santa Cruz | sc-5279 | 4% PFA | 1:100 IF | 10% PBSG |
| TRA-1-60 | Santa Cruz | sc-21705 | 4% PFA | 1:100 IF | 10% PBSG |
| NANOG | Santa Cruz | sc-374001 | 4% PFA | 1:100 IF | 10% PBSG |
| ICAM-1 | R&D | BBA3 | 4% PFA | 1:100 IF | 10% PBSG |

LDL Uptake Assay:

Differentiated BMECs at day 10 were analyzed using a LDL Uptake Assay Kit™ (Abeam). Culture medium was aspirated and replaced with LDL-Dylight™ 550 working solution. Cells were then incubated for 3 hours at 37° C. followed by three washes with PBS and visualized under the microscope with the excitation and emission wavelength at 540 nm and 570 nm, respectively. After visualization, cells were fixed with cell-based Fixative Solution for 10 minutes. Cells were then washed with TBS plus 0.1% Triton-X 100 for five minutes, each followed by 30 min blocking with Cell Based Assay Blocking Solution. Cells were then stained with Rabbit Anti-LDL receptor Primary Antibody and DyLight-488™ Conjugated Secondary Antibody. Images were taken with a fluorescent microscope with excitation and emission wavelengths of 485 nm and 535 nm, respectively.

Efflux Accumulation and Transport Assay:

P-glycoprotein (Pgp), Breast Cancer Resistance Protein (BCRP), and Multidrug Resistance-Associated Protein (MRP) functionality were assessed by intracellular accumulation of fluorescent transporter substrates and transport of fluorescent substrate across BMEC monolayers. 10 µM Rhodamine 123 (Sigma), 20 µM Hoechst (ThermoFisher) and 10 µM 2',7'-dichlorofluorescein diacetate (DCFDA; Life Technologies) were used as the specific substrates for Pgp, BCRP1, and MRP1, respectively. BMECs at day 10 were pre-treated for 1 hour with or without specific transporter inhibitors (10 µM cyclosporin A (Pgp inhibitor), 10 µM Ko143 (BCRP inhibitor) (Sigma) and 1 µM MK571 (MRP inhibitor) (Sigma) in Hank's Balanced Salt Solution (HBSS). Cells were then treated with transporter substrates in HBSS and incubated for one hour at 37° C. on an orbital shaker. Cells were washed with PBS three times and then lysed with radioimmunoprecipitation assay buffer (RIPA buffer) (Pierce Biotechnology). Fluorescence intensity was measured on a plate reader (485 nm excitation and 530 nm emission for Rhodamine 123 and DCFDA, 360 nm excitation and 497 nm emission for Hoechst). Fluorescence intensity was subsequently normalized to cell number determined using a hemacytometer.

Endothelial Cell Tube Formation:

Each well of a 24-well tissue culture plate was coated with 300 µL of 10 mg/L Matrigel®. BMECs at day 10 were dissociated with Accutase™ and plated in hECSM1 plus 50 ng/mL VEGF without RA or bFGF at $2 \times 10^5$ cells/well. Phase contrast images were acquired after 24 hours.

RNA Sequencing and Data Analysis:

Total RNA of day 10 IMR90-4 iPSC-derived BMECs and primary human brain microvascular endothelial cells (Cell Systems, ACBRI 376) were prepared with the Direct-Zol™ RNA MiniPrep Plus kit (Zymo Research) according to the manufacturer's instructions. Samples were sequenced on an Illumina HiSeq2500 at the University of Wisconsin-Madison Biotechnology Center. The resulting sequence reads were mapped to the human genome (hg19) using HISAT49, and the RefSeq transcript levels (FPKMs) were quantified using the Python script rpkmforgenes.py50. A hierarchical clustering of whole transcripts was performed using GENE-E on the log 2 transformed gene counts. Distances were computed using one minus pearson correlation with average linkage. Fastq files of hPSCs (Dye et al., *Elife* 2015, 4:e05098; Tadeu et al., *PloS one* 2015, 10:e0122493; Prasain et al., *Nature biotechnology* 2014, 32:1151-1157), hPSC-derived ectoderm (Tadeu et al., *PloS one* 2015, 10:e0122493), endoderm (Dye et al., *Elife* 2015, 4:e05098), mesoderm (Prasain et al., *Nature biotechnology* 2014, 32:1151-1157) were downloaded from GEO or ArrayExpress (available at ebi.ac.uk/arrayexpress/ on the World Wide Web). The expression of a subset of genes that regulate key BBB attributes, including tight junctions and molecular transporters was analyzed. The gene set comprises 20 tight junction related genes (Bauer et al., *Frontiers in neuroscience* 2014, 8:392; Geier et al., *Clinical Pharmacology & Therapeutics* 2013, 94:636-639; Huntley et al., *Frontiers in neuroscience* 2014, 8:355; Liebner et al., *International Journal of Developmental Biology* 2011, 55:467-476; Obermeier et al., *Nature medicine* 2013, 19:1584-1596) and an unbiased list of all 25 CLDN genes, all 407 solute carrier (SLC) transporters, and all 53 ATP-binding cassette (ABC) transporters regardless of prior knowledge of BBB association (Table 3). Transcript levels (FPKMs) were set at a threshold >1 FPKMs, which indicates moderate expression (Schultz et al., *Bioinformatics* 2012, 28:1086-1092). Primary human BMECs were used to screen out the BBB-related genes from that gene list with the threshold >1FPKMs.

REFERENCES

All publications, including but not limited to patents and patent applications, cited below are herein incorporated by reference as though set forth in their entirety in the present application.

1. Obermeier B, Daneman R, Ransohoff R M: Development, maintenance and disruption of the blood-brain barrier. *Nature Medicine* 2013, 19:1584-1596.
2. Weksler B, Subileau E, Perriere N, Charneau P, Holloway K, Leveque M, Tricoire-Leignel H, Nicotra A, Bourdoulous S, Turowski P: Blood-brain barrier-specific properties of a human adult brain endothelial cell line. *The FASEB Journal* 2005, 19:1872-1874.
3. Abbott N J, Rönnbäck L, Hansson E: Astrocyte—endothelial interactions at the blood—brain barrier. *Nature Reviews Neuroscience* 2006, 7:41-53.
4. Ballabh P, Braun A, Nedergaard M: The blood-brain barrier: an overview: structure, regulation, and clinical implications. *Neurobiology of Disease* 2004, 16:1-13.
5. Pardridge W M: The blood-brain barrier: bottleneck in brain drug development. *NeuroRx* 2005, 2:3-14.
6. Chen Y, Liu L: Modern methods for delivery of drugs across the blood-brain barrier. *Advanced Drug Delivery Reviews* 2012, 64:640-665.
7. Sandoval K E, Witt K A: Blood-brain barrier tight junction permeability and ischemic stroke. *Neurobiology of Disease* 2008, 32:200-219.
8. Fernández-Lopez D, Faustino J, Daneman R, Zhou L, Lee S Y, Derugin N, Wendland M F, Vexler Z S: Blood-brain barrier permeability is increased after acute adult stroke but not neonatal stroke in the rat. *The Journal of Neuroscience* 2012, 32:9588-9600.
9. Yang Y, Rosenberg G A: Blood-brain barrier breakdown in acute and chronic cerebrovascular disease. *Stroke* 2011, 42:3323-3328.
10. Cirrito J R, Deane R, Fagan A M, Spinner M L, Parsadanian M, Finn M B, Jiang H, Prior J L, Sagare A, Bales K R: P-glycoprotein deficiency at the blood-brain barrier increases amyloid-β deposition in an Alzheimer disease mouse model. *The Journal of Clinical Investigation* 2005, 115:3285-3290.
11. Bowman G, Kaye J, Moore M, Waichunas D, Carlson N, Quinn J: Blood-brain barrier impairment in Alzheimer disease Stability and functional significance. *Neurology* 2007, 68:1809-1814.
12. Minagar A, Alexander J S: Blood-brain barrier disruption in multiple sclerosis. *Multiple Sclerosis* 2003, 9:540-549.
13. Kortekaas R, Leenders K L, van Oostrom J C, Vaalburg W, Bart J, Willemsen A, Hendrikse N H: Blood-brain barrier dysfunction in parkinsonian midbrain in vivo. *Annals of Neurology* 2005, 57:176-179.
14. Shlosberg D, Benifla M, Kaufer D, Friedman A: Blood-brain barrier breakdown as a therapeutic target in traumatic brain injury. *Nature Reviews Neurology* 2010, 6:393-403.
15. Beaumont A, Marmarou A, Hayasaki K, Barzo P, Fatouros P, Corwin F, Marmarou C, Dunbar J: The permissive nature of blood brain barrier (BBB) opening in edema formation following traumatic brain injury. In *Brain Edema XI*. Edited by: Springer; 2000:125-129.
16. Huber J D, Egleton R D, Davis T P: Molecular physiology and pathophysiology of tight junctions in the blood-brain barrier. *Trends in Neurosciences* 2001, 24:719-725.
17. Persidsky Y, Stins M, Way D, Witte M H, Weinand M, Kim K S, Bock P, Gendelman H E, Fiala M: A model for monocyte migration through the blood-brain barrier during HIV-1 encephalitis. *The Journal of Immunology* 1997, 158:3499-3510.
18. Annunziata P: Blood-brain barrier changes during invasion of the central nervous system by HIV-1. *Journal of Neurology* 2003, 250:901-906.
19. Brines M L, Ghezzi P, Keenan S, Agnello D, De Lanerolle N C, Cerami C, Itri L M, Cerami A: Erythropoietin crosses the blood-brain barrier to protect against experimental brain injury. *Proceedings of the National Academy of Sciences* 2000, 97:10526-10531.
20. Belayev L, Busto R, Zhao W, Ginsberg M D: Quantitative evaluation of blood-brain barrier permeability following middle cerebral artery occlusion in rats. *Brain Research* 1996, 739:88-96.
21. Asahi M, Wang X, Mori T, Sumii T, Jung J-C, Moskowitz M A, Fini M E, Lo E H: Effects of matrix metalloproteinase-9 gene knock-out on the proteolysis of blood-brain barrier and white matter components after cerebral ischemia. *The Journal of Neuroscience* 2001, 21:7724-7732.
22. Stins M F, Gilles F, Kim K S: Selective expression of adhesion molecules on human brain microvascular endothelial cells. *Journal of Neuroimmunology* 1997, 76:81-90.
23. Wong D, Dorovini-Zis K: Upregulation of intercellular adhesion molecule-1 (ICAM-1) expression in primary cultures of human brain microvessel endothelial cells by cytokines and lipopolysaccharide. *Journal of Neuroimmunology* 1992, 39:11-21.
24. Sano Y, Shimizu F, Abe M, Maeda T, Kashiwamura Y, Ohtsuki S, Terasaki T, Obinata M, Kajiwara K, Fujii M: Establishment of a new conditionally immortalized human brain microvascular endothelial cell line retaining an in vivo blood-brain barrier function. *Journal of Cellular Physiology* 2010, 225:519-528.
25. Weksler B, Romero I A, Couraud P-O: The hCMEC/D3 cell line as a model of the human blood brain barrier. *Fluids Barriers CNS* 2013, 10:16.
26. Syvänen S, Lindhe Ö, Palner M, Kornum B R, Rahman O, Långstrom B, Knudsen G M, Hammarlund-Udenaes M: Species differences in blood-brain barrier transport of three positron emission tomography radioligands with emphasis on P-glycoprotein transport. *Drug Metabolism and Disposition* 2009, 37:635-643.
27. Deli M: Blood-brain barrier models. *Handbook of Neurochemistry and Molecular Neurobiology: Neural Membranes and Transport* 2007:29-55.
28. Naik P, Cucullo L: In vitro blood-brain barrier models: current and perspective technologies. *Journal of Pharmaceutical Sciences* 2012, 101:1337-1354.
29. Thomson J A, Itskovitz-Eldor J, Shapiro S S, Waknitz M A, Swiergiel J J, Marshall V S, Jones J M: Embryonic stem cell lines derived from human blastocysts. *Science* 1998, 282:1145-1147.
30. Zhang S-C, Wernig M, Duncan I D, Brüstle O, Thomson J A: In vitro differentiation of transplantable neural precursors from human embryonic stem cells. *Nature Biotechnology* 2001, 19:1129-1133.
31. Lian X, Hsiao C, Wilson G, Zhu K, Hazeltine L B, Azarin S M, Raval K K, Zhang J, Kamp T J, Palecek S P: Robust cardiomyocyte differentiation from human pluripotent stem cells via temporal modulation of canonical Wnt signaling. *Proceedings of the National Academy of Sciences* 2012, 109:E1848-E1857.
32. Lippmann E S, Azarin S M, Kay J E, Nessler R A, Wilson H K, Al-Ahmad A, Palecek S P, Shusta E V: Derivation of blood-brain barrier endothelial cells from human pluripotent stem cells. *Nature Biotechnology* 2012, 30:783-791.
33. Lippmann E S, Al-Ahmad A, Azarin S M, Palecek S P, Shusta E V: A retinoic acid-enhanced, multicellular 34. Lippmann E S, Al-Ahmad A, Palecek S P, Shusta E V: Modeling the blood-brain barrier using stem cell sources. *Fluids and barriers of the CNS* 2013, 10:2.
35. Wilson H K, Canfield S G, Hjortness M K, Palecek S P, Shusta E V: Exploring the effects of cell seeding density on the differentiation of human pluripotent stem cells to brain microvascular endothelial cells. *Fluids and Barriers of the CNS* 2015, 12:13.
36. Cecchelli R, Aday S, Sevin E, Almeida C, Culot M, Dehouck L, Coisne C, Engelhardt B, Dehouck M-P, Ferreira L: A stable and reproducible human blood-brain barrier model derived from hematopoietic stem cells. *PloS one* 2014, 9:e99733.
37. Boyer-Di Ponio J, El-Ayoubi F, Glacial F, Ganeshamoorthy K, Driancourt C, Godet M, Perrière N, Guillevic O, Couraud P O, Uzan G: Instruction of circulating endothelial progenitors in vitro towards specialized blood-brain barrier and arterial phenotypes. *PloS one* 2014, 9:e84179.
38. Minami H, Tashiro K, Okada A, Hirata N, Yamaguchi T, Takayama K, Mizuguchi H, Kawabata K: Generation of Brain Microvascular Endothelial-Like Cells from Human Induced Pluripotent Stem Cells by Co-Culture with C6 Glioma Cells. *PloS one* 2015, 10:e0128890.
39. Risau W, Wolburg H: Development of the blood-brain barrier. *Trends in Neurosciences* 1990, 13:174-178.
40. Era T, Izumi N, Hayashi M, Tada S, Nishikawa S, Nishikawa S I: Multiple mesoderm subsets give rise to endothelial cells, whereas hematopoietic cells are differentiated only from a restricted subset in embryonic stem cell differentiation culture. *Stem Cells* 2008, 26:401-411.
41. Liebner S, Corada M, Bangsow T, Babbage J, Taddei A, Czupalla C J, Reis M, Felici A, Wolburg H, Fruttiger M: Wnt/β-catenin signaling controls development of the blood-brain barrier. *The Journal of Cell Biology* 2008, 183:409-417.
42. Paolinelli R, Corada M, Ferrarini L, Devraj K, Artus C, Czupalla C J, Rudini N, Maddaluno L, Papa E, Engelhardt B: Wnt activation of immortalized brain endothelial cells as a tool for generating a standardized model of the blood brain barrier in vitro. *PLoS One* 2013, 8:e70233.
43. Stenman J M, Rajagopal J, Carroll T J, Ishibashi M, McMahon J, McMahon A P: Canonical Wnt signaling regulates organ-specific assembly and differentiation of CNS vasculature. *Science* 2008, 322:1247-1250.
44. Mizee M R, Wooldrik D, Lakeman K A, van het Hof B, Drexhage J A, Geerts D, Bugiani M, Aronica E, Mebius R E, Prat A: Retinoic acid induces blood-brain barrier development. *The Journal of Neuroscience* 2013, 33:1660-1671.
45. Mizee M R, Nijland P G, van der Pol S M, Drexhage J A, van het Hof B, Mebius R, van der Valk P, van Horssen J, Reijerkerk A, de Vries H E: Astrocyte-derived retinoic acid: a novel regulator of blood-brain barrier function in multiple sclerosis. *Acta Neuropathologica* 2014, 128:691-703.
46. Lindsley R C, Gill J G, Kyba M, Murphy T L, Murphy K M: Canonical Wnt signaling is required for development of embryonic stem cell-derived mesoderm. *Development* 2006, 133:3787-3796.
47. Lian X, Bao X, Al-Ahmad A, Liu J, Wu Y, Dong W, Dunn K K, Shusta E V, Palecek S P: Efficient differentiation of human pluripotent stem cells to endothelial progenitors via small-molecule activation of WNT signaling. *Stem Cell Reports* 2014, 3:804-816.
48. Lam A Q, Freedman B S, Morizane R, Lerou P H, Valerius M T, Bonventre J V: Rapid and efficient differentiation of human pluripotent stem cells into intermediate mesoderm that forms tubules expressing kidney proximal tubular markers. *Journal of the American Society of Nephrology* 2013:ASN. 2013080831.
49. Lian X, Bao X, Zilberter M, Westman M, Fisahn A, Hsiao C, Hazeltine L B, Dunn K K, Kamp T J, Palecek S P: Chemically defined, albumin-free human cardiomyocyte generation. *Nature Methods* 2015, 12:595-596.
50. Ng E S, Azzola L, Sourris K, Robb L, Stanley E G, Elefanty A G: The primitive streak gene Mixl1 is required for efficient haematopoiesis and BMP4-induced ventral mesoderm patterning in differentiating ES cells. *Development* 2005, 132:873-884.
51. Bauer H-C, Krizbai I A, Bauer H, Traweger A: "You Shall Not Pass"—tight junctions of the blood brain barrier. *Frontiers in Neuroscience* 2014, 8:392.
52. Geier E G, Chen E C, Webb A, Papp A C, Yee S W, Sadee W, Giacomini K M: Profiling solute carrier transporters in the human blood-brain barrier. *Clinical Pharmacology & Therapeutics* 2013, 94:636-639.
53. Huntley M A, Bien-Ly N, Daneman R, Watts R J: Dissecting gene expression at the blood-brain barrier. *Frontiers in Neuroscience* 2014, 8:355.
54. Liebner S, Czupalla C J, Wolburg H: Current concepts of blood-brain barrier development. *International Journal of Developmental Biology* 2011, 55:467-476.
55. Weidenfeller C, Svendsen C N, Shusta E V: Differentiating embryonic neural progenitor cells induce blood-brain barrier properties. *Journal of neurochemistry* 2007, 101:555-565.
56. Lippmann E S, Weidenfeller C, Svendsen C N, Shusta E V: Blood-brain barrier modeling with co-cultured neural progenitor cell-derived astrocytes and neurons. *Journal of neurochemistry* 2011, 119:507-520.
57. Lai C-H, Kuo K-H: The critical component to establish in vitro BBB model: Pericyte. *Brain Research Reviews* 2005, 50:258-265.
58. Lippmann E S, Al-Ahmad A, Azarin S M, Palecek S P, Shusta E V: A retinoic acid-enhanced, multicellular human blood-brain barrier model derived from stem cell sources. *Scientific Reports* 2014, 4:4160.
59. Canfield S G, Stebbins M J, Morales B S, Asai S W, Vatine G D, Svendsen C N, Palecek S P, Shusta E V: An Isogenic Blood-Brain Barrier Model Comprising Brain Endothelial Cells, Astrocytes and Neurons Derived from Human Induced Pluripotent Stem Cells. *Journal of Neurochemistry* 2016.
60. Ebert A D, Shelley B C, Hurley A M, Onorati M, Castiglioni V, Patitucci T N, Svendsen S P, Mattis V B, McGivern J V, Schwab A J: E Z spheres: a stable and expandable culture system for the generation of pre-rosette multipotent stem cells from human ESCs and iPSCs. *Stem Cell Research* 2013, 10:417-427.
61. Gage B K, Webber T D, Kieffer T J: Initial cell seeding density influences pancreatic endocrine development during in vitro differentiation of human embryonic stem cells. *PloS one* 2013, 8:e82076.
62. Lu H, Guo L, Wozniak M J, Kawazoe N, Tateishi T, Zhang X, Chen G: Effect of cell density on adipogenic differentiation of mesenchymal stem cells. *Biochemical and Biophysical Research Communications* 2009, 381:322-327.

63. Otero J J, Fu W, Kan L, Cuadra A E, Kessler J A: β-Catenin signaling is required for neural differentiation of embryonic stem cells. *Development* 2004, 131:3545-3557.
64. Wilson H K, Canfield S G, Hjortness M K, Palecek S P, Shusta E V: Exploring the effects of cell seeding density on the differentiation of human pluripotent stem cells to brain microvascular endothelial cells. *Fluids and Barriers of the CNS* 2015, 12:1.
65. Kurz H: Cell lineages and early patterns of embryonic CNS vascularization. *Cell Adhesion & Migration* 2009, 3:205-210.
66. Chambers S M, Fasano C A, Papapetrou E P, Tomishima M, Sadelain M, Studer L: Highly efficient neural conversion of human E S and iPS cells by dual inhibition of SMAD signaling. *Nature Biotechnology* 2009, 27:275-280.
67. Selekman J A, Grundl N J, Kolz J M, Palecek S P: Efficient generation of functional epithelial and epidermal cells from human pluripotent stem cells under defined conditions. *Tissue Engineering Part C: Methods* 2013, 19:949-960.
68. Lippmann E S, Estevez-Silva M C, Ashton R S: Defined human pluripotent stem cell culture enables highly efficient neuroepithelium derivation without small molecule inhibitors. *Stem Cells* 2014, 32:1032-1042.
69. FREY A, MECKELEIN B, WEILER-GÜTTLER H, MÖCKEL B, FLACH R, GASSEN H G: Pericytes of the brain microvasculature express γ-glutamyl transpeptidase. *European Journal of Biochemistry* 1991, 202:421-429.
70. Nakagawa S, Deli M A, Kawaguchi H, Shimizudani T, Shimono T, Kittel A, Tanaka K, Niwa M: A new blood-brain barrier model using primary rat brain endothelial cells, pericytes and astrocytes. *Neurochemistry international* 2009, 54:253-263.
71. Nakagawa S, Deli M A, Nakao S, Honda M, Hayashi K, Nakaoke R, Kataoka Y, Niwa M: Pericytes from brain microvessels strengthen the barrier integrity in primary cultures of rat brain endothelial cells. *Cellular and molecular neurobiology* 2007, 27:687-694.
72. Pipparelli A, Arsenijevic Y, Thuret G, Gain P, Nicolas M, Majo F: ROCK inhibitor enhances adhesion and wound healing of human corneal endothelial cells. *PloS one* 2013, 8:e62095.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

TABLE 3

| Gene list | | | | | | |
|---|---|---|---|---|---|---|
| #506 BBB gene list | 234 gene list | hBMECs | 234 gene list | DF-BMECs | 234 gene list | UM-BMECs |
| ABCA11 | CAV1 | 923.7407 | SLC2A3 | 252.0928 | SLC2A3 | 610.8353 |
| ABCC7 | ICAM2 | 278.3834 | SLC25A6 | 213.1756 | HIF1A | 151.1465 |
| SLC25A9 | MCAM | 274.1456 | SLC25A5 | 186.9119 | SLC25A5 | 142.1456 |
| SLC42A3 | HIF1A | 249.6294 | SLC25A3 | 157.2549 | SLC25A3 | 138.6716 |
| SLC24A6 | CDH5 | 234.3097 | SLC16A1 | 143.3172 | SLC2A14 | 123.62 |
| SLC9A11 | PECAM1 | 203.7012 | HIF1A | 122.4893 | SLC38A1 | 105.316 |
| CAV1 | SLC25A3 | 183.5255 | SLC2A1 | 93.9611 | SLC38A2 | 100.156 |
| ICAM2 | SLC25A5 | 165.756 | SLC38A1 | 92.72981 | SLC16A1 | 90.03843 |
| MCAM | CLDN11 | 136.989 | SLC38A2 | 81.24737 | SLC25A6 | 87.75701 |
| HIF1A | SLC38A2 | 136.0453 | SLC44A2 | 67.27332 | F11R | 74.97036 |
| CDH5 | CAV2 | 106.9793 | SLC25A13 | 61.07322 | SLC3A2 | 71.89055 |
| PECAM1 | FLT1 | 105.9402 | TJP1 | 56.69343 | TJP1 | 71.70241 |
| SLC25A3 | SLC29A1 | 90.7043 | ABCE1 | 56.32067 | SLC2A1 | 70.75552 |
| SLC25A5 | ABCE1 | 86.04381 | SLC3A2 | 56.19216 | CLDN10 | 68.96303 |
| CLDN11 | SLC38A1 | 82.47343 | SLC2A14 | 56.11487 | SLC44A2 | 68.81839 |
| SLC38A2 | TJP1 | 76.45356 | F11R | 55.14908 | SLC7A5 | 63.41564 |
| CAV2 | SLC43A3 | 74.88526 | SLC1A5 | 53.58474 | SLC39A1 | 53.76249 |
| FLT1 | VWF | 73.26097 | SLC25A39 | 52.78089 | SLC25A13 | 52.07851 |
| SLC29A1 | SLC16A1 | 68.35225 | SLC39A1 | 51.60302 | SLC39A10 | 51.38782 |
| ABCE1 | TJP2 | 67.96791 | TJP2 | 49.49886 | TJP2 | 50.06371 |
| SLC38A1 | SLC20A1 | 62.491 | SLC39A10 | 48.06552 | ABCE1 | 45.28388 |
| TJP1 | SLC7A11 | 60.69881 | SLC30A9 | 46.72972 | SLC30A9 | 44.90368 |
| SLC43A3 | F11R | 57.99209 | CLDN7 | 44.32662 | SLC35F2 | 40.78186 |
| VWF | SLC25A6 | 57.5346 | SLC29A1 | 44.28459 | SLC39A6 | 40.62602 |
| SLC16A1 | JAM3 | 54.89288 | SLC9A3R1 | 41.81585 | CLDND1 | 38.92117 |
| TJP2 | SLC3A2 | 50.75996 | SLC39A6 | 37.77367 | SLC25A23 | 37.91454 |
| SLC20A1 | SLC35F2 | 46.47151 | SLC35F2 | 35.70086 | SLC25A39 | 35.84938 |
| SLC7A11 | SLC4A7 | 43.35404 | CLDND1 | 33.66144 | SLC9A3R1 | 33.92086 |
| F11R | SLC39A1 | 42.83734 | SLC25A1 | 33.53528 | CLDN7 | 33.84267 |
| SLC25A6 | SLC25A24 | 41.87745 | SLC7A5 | 33.22988 | SLC25A24 | 29.86583 |
| JAM3 | SLC35B1 | 34.06834 | SLC25A36 | 28.83266 | SLC1A5 | 28.91319 |
| SLC3A2 | SLC30A9 | 33.06038 | ABCD3 | 28.48802 | SLC35D2 | 28.25116 |
| SLC35F2 | CLDND1 | 32.75058 | CDH5 | 28.00627 | SLC29A1 | 25.86402 |
| SLC4A7 | SLC39A9 | 31.23809 | CLDN10 | 26.98014 | SLC9A7 | 25.72785 |
| SLC39A1 | SLC39A10 | 30.98473 | SLC25A24 | 26.75072 | SLC35B2 | 24.7002 |
| SLC25A24 | SLC4A1AP | 28.62383 | SLC5A6 | 26.0891 | SLC11A2 | 24.61003 |
| SLC35B1 | ABCF2 | 24.58603 | SLC39A8 | 24.77252 | SLC20A1 | 24.17319 |
| SLC30A9 | SLC25A51 | 24.22399 | SLC4A7 | 23.76598 | SLC5A6 | 23.3824 |
| CLDND1 | SLC25A46 | 24.21591 | SLC5A3 | 23.47273 | SLC25A36 | 23.11703 |
| SLC39A9 | SLC44A2 | 23.91665 | SLC37A4 | 22.58407 | SLC48A1 | 22.83945 |
| SLC39A10 | SLC25A32 | 23.63031 | SLC11A2 | 21.88627 | SLC50A1 | 22.61239 |
| SLC4A1AP | SLC25A39 | 22.65866 | SLC39A9 | 21.62626 | SLC25A1 | 22.59764 |

TABLE 3-continued

Gene list

| #506 BBB gene list | 234 gene list | hBMECs | 234 gene list | DF-BMECs | 234 gene list | UM-BMECs |
|---|---|---|---|---|---|---|
| ABCF2 | SLC1A1 | 20.44956 | SLC25A23 | 20.90531 | SLC39A9 | 22.25151 |
| SLC25A51 | SLC11A2 | 19.93301 | SLC35A4 | 20.18808 | SLC35B1 | 21.83007 |
| SLC25A46 | SLC1A5 | 19.51665 | SLC7A2 | 19.87333 | ABCD3 | 21.43351 |
| SLC44A2 | SLC39A14 | 18.42165 | SLC35D2 | 19.66506 | SLC38A9 | 20.73522 |
| SLC25A32 | SLC25A44 | 17.91983 | SLC25A11 | 19.64424 | SLC2A12 | 20.53667 |
| SLC25A39 | SLC35B2 | 17.85137 | SLC25A46 | 19.4795 | SLC35A4 | 20.20352 |
| SLC1A1 | SLC44A1 | 15.89151 | SLC35B2 | 18.90054 | SLC25A46 | 19.9377 |
| SLC11A2 | SLC50A1 | 15.65628 | CLDN12 | 18.12411 | SLC4A7 | 19.62326 |
| SLC1A5 | SLC33A1 | 15.40879 | SLC6A6 | 17.64542 | ABCF2 | 19.54797 |
| SLC39A14 | SLC35F5 | 15.4087 | SLC20A1 | 17.32783 | SLC44A1 | 18.02392 |
| SLC25A44 | SLC2A3 | 15.20934 | SLC44A1 | 17.26487 | SLC25A11 | 17.19072 |
| SLC35B2 | SLC35A5 | 15.09354 | SLC35E2B | 17.26174 | OCLN | 16.99925 |
| SLC44A1 | SLC35D2 | 14.85562 | SLC35B1 | 16.91038 | SLC4A1AP | 16.98139 |
| SLC50A1 | SLC30A5 | 14.43843 | SLC9A7 | 16.41598 | SLC25A14 | 16.88279 |
| SLC33A1 | SLC30A7 | 14.2732 | ABCF2 | 16.39811 | SLC35A2 | 16.35939 |
| SLC35F5 | SLC7A6 | 14.19045 | ABCB7 | 15.97855 | SLC35E2B | 16.35016 |
| SLC2A3 | SLC12A2 | 13.96953 | OCLN | 15.75396 | SLC6A6 | 16.11681 |
| SLC35A5 | ABCD3 | 13.81484 | SLC25A38 | 15.40118 | SLC37A3 | 15.21492 |
| SLC35D2 | SLC35A4 | 13.62119 | SLC50A1 | 15.23794 | ABCB7 | 15.0576 |
| SLC30A5 | SLC37A3 | 13.46261 | SLC35A1 | 15.04173 | SLC5A3 | 14.85095 |
| SLC30A7 | SLC25A23 | 13.33278 | SLC35A5 | 14.90034 | SLC39A8 | 14.82668 |
| SLC7A6 | SLC7A1 | 13.25892 | SLC16A3 | 14.71892 | SLC30A6 | 14.6869 |
| SLC12A2 | ABCB7 | 13.12365 | SLC35A2 | 14.65579 | CAV1 | 14.52592 |
| ABCD3 | SLC31A1 | 12.37542 | SLC25A17 | 14.35371 | MCAM | 14.49007 |
| SLC35A4 | SLC35F6 | 12.24834 | SLC4A1AP | 14.30081 | SLC25A38 | 14.20695 |
| SLC37A3 | SLC12A6 | 12.19731 | SLC35B4 | 14.16154 | SLC25A17 | 13.24071 |
| SLC25A23 | ABCC4 | 11.77731 | SLC37A3 | 13.93202 | SLC7A6 | 13.04645 |
| SLC7A1 | SLC6A6 | 11.43204 | SLC39A14 | 13.38355 | SLC31A1 | 12.83048 |
| ABCB7 | SLC25A20 | 11.31557 | SLC19A2 | 13.18775 | CLDN12 | 12.82142 |
| SLC31A1 | SLC35A1 | 11.20306 | SLC41A3 | 12.72882 | SLC43A3 | 12.7829 |
| SLC35F6 | SLC41A3 | 10.98087 | SLC38A10 | 12.62832 | SLC35A1 | 12.16555 |
| SLC12A6 | ABCC1 | 10.95128 | SLC35C2 | 12.13298 | SLC35E2 | 12.16248 |
| ABCC4 | SLC40A1 | 10.8633 | SLC25A29 | 12.07869 | SLC37A4 | 12.08897 |
| SLC6A6 | SLC25A36 | 10.83388 | ABCA1 | 11.91767 | SLC41A3 | 12.01466 |
| SLC25A20 | SLC25A13 | 10.77849 | SLC10A7 | 11.5767 | SLC25A44 | 11.94043 |
| SLC35A1 | SLC25A37 | 10.65943 | SLC30A6 | 11.57144 | ABCF3 | 11.85583 |
| SLC41A3 | SLC17A5 | 10.53626 | ABCG2 | 11.55531 | SLC12A4 | 11.74317 |
| ABCC1 | SLC25A38 | 10.31958 | SLC35F5 | 11.48433 | ABCC5 | 11.71671 |
| SLC40A1 | SLC23A2 | 10.23087 | SLC18B1 | 11.47867 | SLC35E1 | 11.66272 |
| SLC25A36 | SLC9A3R2 | 9.998613 | SLC9A6 | 11.40468 | SLC12A2 | 11.3905 |
| SLC25A13 | SLC46A3 | 9.908212 | SLC7A6OS | 11.39558 | SLC35B4 | 11.3725 |
| SLC25A37 | SLC18B1 | 9.879486 | SLC38A9 | 11.21661 | SLC35A5 | 11.30591 |
| SLC17A5 | SLC25A11 | 9.742069 | SLC33A1 | 10.70683 | ABCA1 | 11.03958 |
| SLC25A38 | SLC38A6 | 9.526767 | ABCF3 | 10.66462 | SLC25A32 | 10.88902 |
| SLC23A2 | SLC25A43 | 9.417356 | SLC25A51 | 10.64999 | SLC9A6 | 10.85257 |
| SLC9A3R2 | SLC30A6 | 9.213449 | SLC35E2 | 10.26557 | SLC35F5 | 10.72137 |
| SLC46A3 | SLC26A2 | 9.058527 | SLC35E1 | 10.2129 | JAM3 | 10.65142 |
| SLC18B1 | SLC10A7 | 8.942612 | SLC12A4 | 9.863589 | SLC7A2 | 10.49417 |
| SLC25A11 | SLC7A6OS | 8.820074 | SLC31A1 | 9.823099 | SLC30A5 | 10.2489 |
| SLC38A6 | SLC35B3 | 8.76971 | SLC4A2 | 9.775447 | SLC19A2 | 10.22101 |
| SLC25A43 | SLC30A1 | 8.588276 | SLC25A40 | 9.707604 | ABCC1 | 10.11523 |
| SLC30A6 | ABCG2 | 8.238564 | SLC23A2 | 9.34232 | SLC39A14 | 10.04289 |
| SLC26A2 | SLC39A6 | 8.167096 | ABCC5 | 9.335807 | SLC25A51 | 9.995096 |
| SLC10A7 | SLC5A6 | 7.967356 | SLC25A44 | 9.335145 | SLC20A2 | 9.892753 |
| SLC7A6OS | SLC25A30 | 7.889163 | SLC20A2 | 9.178483 | ABCG2 | 9.820886 |
| SLC35B3 | SLC35E2 | 7.855851 | SLC16A9 | 9.121988 | SLC25A37 | 9.197012 |
| SLC30A1 | ABCB10 | 7.797414 | CAV1 | 8.869287 | SLC35F6 | 9.093918 |
| ABCG2 | SLC38A9 | 7.697407 | SLC43A3 | 8.600246 | SLC33A1 | 8.823266 |
| SLC39A6 | SLC25A40 | 7.663975 | SLC41A1 | 8.580978 | SLC30A7 | 8.81682 |
| SLC5A6 | ABCF3 | 7.630236 | SLC25A32 | 8.390015 | SLC25A40 | 8.7024 |
| SLC25A30 | SLC35E1 | 7.556514 | SLC25A37 | 8.388699 | CDH5 | 8.69502 |
| SLC35E2 | SLC25A1 | 7.525357 | JAM3 | 8.364314 | SLC4A2 | 8.643693 |
| ABCB10 | SLC25A16 | 7.489493 | SLC7A5P2 | 8.252218 | SLC7A1 | 8.608181 |
| SLC38A9 | SLC6A8 | 7.323966 | SLC36A4 | 8.231476 | SLC12A6 | 8.571138 |
| SLC25A40 | SLC9B2 | 7.128162 | ABCC1 | 8.111134 | SLC39A11 | 8.513285 |
| ABCF3 | SLC41A1 | 6.930944 | SLC30A5 | 8.007126 | SLC23A2 | 8.253028 |
| SLC35E1 | SLC37A4 | 6.858014 | SLC39A11 | 7.726905 | SLC35B3 | 8.055638 |
| SLC25A1 | SLC15A4 | 6.853793 | SLC25A14 | 7.713775 | SLC16A9 | 8.046499 |
| SLC25A16 | CLDN14 | 6.841163 | SLC18A2 | 7.713735 | ABCD4 | 7.969777 |
| SLC6A8 | SLC25A12 | 6.82804 | SLC12A2 | 7.700731 | SLC7A6OS | 7.959692 |
| SLC9B2 | SLC48A1 | 6.787476 | SLC7A6 | 7.455157 | SLC35C2 | 7.733024 |
| SLC41A1 | SLC25A28 | 6.720037 | ABCC4 | 7.441502 | SLC40A1 | 7.668746 |
| SLC37A4 | SLC25A52 | 6.667478 | SLC40A1 | 7.327833 | SLC36A4 | 7.60958 |
| SLC15A4 | SLC2A1 | 6.404123 | SLC52A2 | 7.315052 | SLC25A28 | 7.353667 |
| CLDN14 | SLC25A17 | 6.374539 | SLC48A1 | 7.237134 | SLC38A7 | 7.330979 |

TABLE 3-continued

Gene list

| #506 BBB gene list | 234 gene list | hBMECs | 234 gene list | DF-BMECs | 234 gene list | UM-BMECs |
|---|---|---|---|---|---|---|
| SLC25A12 | SLC45A3 | 6.179573 | SLC35B3 | 7.148587 | SLC41A1 | 7.329091 |
| SLC48A1 | SLC25A14 | 6.176458 | SLC35F6 | 7.063546 | SLC16A4 | 7.285852 |
| SLC25A28 | SLC7A7 | 6.056539 | SLC30A7 | 6.950792 | SLC25A15 | 7.018179 |
| SLC25A52 | ABCA3 | 6.041755 | SLC12A6 | 6.870094 | SLC37A1 | 6.981045 |
| SLC2A1 | SLC35A3 | 5.97345 | SLC2A12 | 6.822289 | SLC38A10 | 6.795447 |
| SLC25A17 | SLC35C2 | 5.886805 | SLC25A4 | 6.80334 | CAV2 | 6.763466 |
| SLC45A3 | SLC9A1 | 5.774904 | SLC16A2 | 6.771058 | SLC18B1 | 6.680213 |
| SLC25A14 | SLC35E2B | 5.77416 | SLC2A4RG | 6.751262 | SLC7A5P2 | 6.638324 |
| SLC7A7 | SLC35B4 | 5.684548 | SLC35A3 | 6.730863 | SLC16A2 | 6.366558 |
| ABCA3 | ABCD4 | 5.651213 | ABCB10 | 6.690164 | SLC18A2 | 6.316656 |
| SLC35A3 | SLC35G2 | 5.574308 | SLC25A28 | 6.663808 | SLC25A4 | 6.252142 |
| SLC35C2 | SLC38A7 | 5.42276 | SLC10A3 | 6.629065 | CLDN11 | 6.212397 |
| SLC9A1 | SLC5A3 | 5.388036 | SLC25A15 | 6.429072 | SLC24A1 | 6.16772 |
| SLC35E2B | SLC39A13 | 5.291944 | SLC37A1 | 6.369922 | SLC52A2 | 6.15893 |
| SLC35B4 | SLC41A2 | 5.17794 | ABCD4 | 6.305381 | SLC25A20 | 5.875959 |
| ABCD4 | ABCA6 | 5.101244 | SLC25A26 | 6.26727 | SLC25A33 | 5.870099 |
| SLC35G2 | SLC9A6 | 5.032552 | SLC7A1 | 6.19808 | SLC10A7 | 5.844128 |
| SLC38A7 | SLC20A2 | 4.791322 | SLC2A8 | 6.087815 | SLC30A1 | 5.82388 |
| SLC5A3 | SLC12A4 | 4.7702 | SLC16A4 | 5.860985 | SLC25A29 | 5.624951 |
| SLC39A13 | SLC25A4 | 4.728352 | SLC2A13 | 5.773666 | SLC35E3 | 5.548845 |
| SLC41A2 | SLC4A2 | 4.708312 | SLC24A1 | 5.706535 | SLC35A3 | 5.367006 |
| ABCA6 | CLDN7 | 4.651275 | SLC17A5 | 5.640505 | SLC10A3 | 5.354412 |
| SLC9A6 | SLC8B1 | 4.624652 | SLC39A3 | 5.478398 | SLC44A5 | 5.338708 |
| SLC20A2 | SLC9A3R1 | 4.624386 | SLC35E3 | 5.367367 | SLC7A7 | 5.146036 |
| SLC12A4 | SLC35E3 | 4.560941 | SLC38A7 | 5.275521 | ABCC4 | 5.110034 |
| SLC25A4 | SLC36A4 | 4.524488 | SLC30A4 | 5.206057 | SLC25A16 | 5.091252 |
| SLC4A2 | SLC4A8 | 4.492913 | SLC25A33 | 5.145579 | SLC16A3 | 5.054938 |
| CLDN7 | SLC18A2 | 4.410194 | SLC27A4 | 4.704437 | SLC6A15 | 4.943508 |
| SLC8B1 | SLC16A3 | 4.18688 | SLC25A19 | 4.699116 | SLC26A6 | 4.881237 |
| SLC9A3R1 | SLC7A11-AS1 | 4.169528 | SLC26A6 | 4.556017 | SLC17A5 | 4.600665 |
| SLC35E3 | SLC38A10 | 4.141603 | SLC30A1 | 4.530791 | SLC30A4 | 4.521532 |
| SLC36A4 | SLC39A8 | 4.105094 | MCAM | 4.207526 | SLC9A1 | 4.286968 |
| SLC4A8 | SLC24A1 | 4.090698 | SLC7A7 | 4.204975 | SLC22A23 | 4.188286 |
| SLC18A2 | SLC35A2 | 4.080426 | SLC1A1 | 4.184253 | SLC25A26 | 4.108745 |
| SLC16A3 | SLC9A7 | 3.991476 | SLC38A6 | 4.177333 | SLC25A12 | 4.009335 |
| SLC7A11-AS1 | SLC1A4 | 3.876767 | SLC27A3 | 4.125926 | SLC35D1 | 3.982762 |
| SLC38A10 | SLC25A15 | 3.823741 | SLC25A16 | 3.98039 | ABCC10 | 3.951296 |
| SLC39A8 | ABCC5 | 3.799949 | SLC25A20 | 3.973409 | SLC2A4RG | 3.685668 |
| SLC24A1 | SLC25A33 | 3.663425 | SLC44A5 | 3.923323 | SLC38A6 | 3.67615 |
| SLC35A2 | SLC25A19 | 3.649016 | SLC4A8 | 3.868711 | SLC2A8 | 3.626527 |
| SLC9A7 | SLC43A1 | 3.605161 | ABCC10 | 3.728089 | SLC6A8 | 3.567135 |
| SLC1A4 | SLC25A29 | 3.500198 | SLC39A13 | 3.712465 | ABCB10 | 3.541202 |
| SLC25A15 | SLC7A5 | 3.422199 | SLC12A9 | 3.497827 | SLC1A4 | 3.520103 |
| ABCC5 | ABCB6 | 3.293545 | SLC2A11 | 3.491258 | SLC39A3 | 3.469696 |
| SLC25A33 | ABCA5 | 3.242039 | SLC7A11 | 3.46873 | ABCA11P | 3.413526 |
| SLC25A19 | SLC6A15 | 3.200893 | SLC9A8 | 3.439343 | SLC26A2 | 3.382889 |
| SLC43A1 | SLC2A10 | 3.189633 | SLC26A2 | 3.346508 | SLC27A4 | 3.379123 |
| SLC25A29 | SLC10A3 | 3.187604 | SLC19A1 | 3.325034 | SLC4A8 | 3.300027 |
| SLC7A5 | CLDN12 | 3.170898 | SLC6A15 | 3.323116 | SLC2A13 | 3.26573 |
| ABCB6 | CLDN5 | 3.144691 | SLC22A23 | 3.075992 | SLC41A2 | 3.226567 |
| ABCA5 | SLC16A2 | 3.015845 | SLC16A5 | 3.073074 | SLC26A11 | 3.032897 |
| SLC6A15 | SLC26A6 | 2.928897 | SLC36A1 | 3.061966 | SLC25A30 | 3.023375 |
| SLC2A10 | ABCG1 | 2.899549 | SLC35G1 | 3.047712 | SLC2A10 | 3.000119 |
| SLC10A3 | SLC19A2 | 2.873943 | SLC25A25 | 3.024935 | SLC35G1 | 2.911678 |
| CLDN12 | SLC25A25 | 2.813299 | SLC25A27 | 2.911114 | SLC1A1 | 2.888386 |
| CLDN5 | SLC25A26 | 2.807377 | ABCB6 | 2.894889 | FLT1 | 2.871825 |
| SLC16A2 | SLC35E4 | 2.807377 | SLC9A1 | 2.870754 | SLC25A19 | 2.798569 |
| SLC26A6 | SLC47A1 | 2.798204 | SLC26A11 | 2.835428 | SLC35G2 | 2.701656 |
| ABCG1 | SLC36A1 | 2.78136 | SLC25A30 | 2.820294 | SLC25A43 | 2.497151 |
| SLC19A2 | ABCC5-AS1 | 2.717161 | SLC25A12 | 2.773978 | SLC9B2 | 2.457178 |
| SLC25A25 | SLC27A4 | 2.71138 | SLC12A7 | 2.681496 | SLC2A11 | 2.416716 |
| SLC25A26 | SLC35D1 | 2.643386 | SLC25A43 | 2.6356 | SLC16A5 | 2.402106 |
| SLC35E4 | SLC16A7 | 2.565574 | SLC25A21-AS1 | 2.63491 | SLC7A11 | 2.338561 |
| SLC47A1 | SLC2A14 | 2.492277 | SLC6A8 | 2.617316 | SLC25A27 | 2.333854 |
| SLC36A1 | SLC9A8 | 2.44206 | SLC9B2 | 2.599457 | SLC25A25 | 2.291076 |
| ABCC5-AS1 | SLC2A13 | 2.402028 | ABCA5 | 2.493851 | SLC9A8 | 2.282608 |
| SLC27A4 | SLC16A4 | 2.358955 | SLC16A1-AS1 | 2.477815 | SLC35C1 | 2.276645 |
| SLC35D1 | SLC39A4 | 2.353052 | SLC2A10 | 2.350852 | SLC36A1 | 2.25587 |
| SLC16A7 | SLC31A2 | 2.298712 | SLC27A1 | 2.291298 | SLC25A52 | 2.144389 |
| SLC2A14 | SLC7A2 | 2.197604 | SLC22A5 | 2.280795 | CLDN15 | 2.086779 |
| SLC9A8 | ABCA11P | 2.162356 | ABCA11P | 2.183504 | SLC12A7 | 2.036138 |
| SLC2A13 | SLC4A11 | 2.067843 | CAV2 | 2.170436 | SLC22A5 | 1.881857 |
| SLC16A4 | ABCA9 | 2.062904 | ABCA3 | 1.994074 | CLDN20 | 1.839093 |
| SLC39A4 | SLC16A13 | 2.041291 | SLC35D1 | 1.887128 | SLC16A13 | 1.817148 |

TABLE 3-continued

Gene list

| #506 BBB gene list | 234 gene list | hBMECs | 234 gene list | DF-BMECs | 234 gene list | UM-BMECs |
|---|---|---|---|---|---|---|
| SLC31A2 | SLC9A9 | 2.037834 | SLC16A13 | 1.859779 | ABCG1 | 1.806817 |
| SLC7A2 | SLC39A3 | 2.026507 | SLC47A1 | 1.858928 | SLC45A3 | 1.784481 |
| ABCA11P | SLC35C1 | 1.972902 | CLDN15 | 1.716215 | ABCB6 | 1.683963 |
| SLC4A11 | SLC22A4 | 1.953524 | SLC45A3 | 1.682159 | SLC12A9 | 1.630878 |
| ABCA9 | SLC37A1 | 1.81226 | CLDN20 | 1.680569 | SLC31A2 | 1.611464 |
| SLC16A13 | SLC17A9 | 1.769929 | SLC8B1 | 1.570282 | SLC25A21-AS1 | 1.601919 |
| SLC9A9 | SLC22A23 | 1.764406 | SLC16A7 | 1.551389 | SLC27A1 | 1.522368 |
| SLC39A3 | SLC16A1-AS1 | 1.72676 | FLT1 | 1.482148 | SLC8B1 | 1.494263 |
| SLC35C1 | SLC44A5 | 1.701749 | ABCB9 | 1.398731 | SLC39A13 | 1.450947 |
| SLC22A4 | ABCA8 | 1.652087 | SLC35C1 | 1.398033 | SLC43A2 | 1.332146 |
| SLC37A1 | SLC12A9 | 1.61651 | SLC31A2 | 1.374391 | ABCA5 | 1.31138 |
| SLC17A9 | SLC2A4RG | 1.6131 | SLC1A4 | 1.324516 | SLC4A11 | 1.28855 |
| SLC22A23 | SLC7A5P2 | 1.608011 | SLC43A2 | 1.288621 | SLC19A1 | 1.25397 |
| SLC16A1-AS1 | OCLN | 1.607414 | SLC41A2 | 1.20395 | ABCA3 | 1.246954 |
| SLC44A5 | SLC26A11 | 1.591181 | SLC25A52 | 1.028764 | JAM2 | 1.205741 |
| ABCA8 | CLDN15 | 1.554813 | SLC4A11 | 0.96161 | SLC46A3 | 1.139848 |
| SLC12A9 | SLC52A2 | 1.544335 | ABCC5-AS1 | 0.866443 | SLC27A3 | 1.053088 |
| SLC2A4RG | SLC2A11 | 1.532439 | SLC39A4 | 0.851669 | ABCB9 | 0.950726 |
| SLC7A5P2 | SLC30A4 | 1.511683 | SLC35G2 | 0.792349 | SLC2A6 | 0.942145 |
| OCLN | SLC12A7 | 1.489623 | SLC9A3R2 | 0.752173 | SLC9A3R2 | 0.876967 |
| SLC26A11 | SLC27A3 | 1.47873 | SLC43A1 | 0.628691 | ABCC5-AS1 | 0.677266 |
| CLDN15 | ABCC10 | 1.474117 | SLC17A9 | 0.548714 | SLCO4A1 | 0.653575 |
| SLC52A2 | SLC16A9 | 1.470279 | SLCO4A1 | 0.501681 | SLC16A1-AS1 | 0.633586 |
| SLC2A11 | SLC2A8 | 1.431852 | CLDN14 | 0.495563 | SLC16A7 | 0.62852 |
| SLC30A4 | ICAM1 | 1.413326 | SLC35E4 | 0.479577 | SLC35E4 | 0.624779 |
| SLC12A7 | SLC19A1 | 1.408644 | SLC46A3 | 0.435388 | SLC47A1 | 0.581222 |
| SLC27A3 | SLC25A34 | 1.328311 | CLDN11 | 0.434721 | CLDN14 | 0.548041 |
| ABCC10 | SLC2A12 | 1.320097 | SLC2A6 | 0.430468 | SLC39A4 | 0.499288 |
| SLC16A9 | SLC2A6 | 1.295948 | JAM2 | 0.423 | ICAM1 | 0.489275 |
| SLC2A8 | SLC39A11 | 1.292349 | SLC25A34 | 0.397096 | SLC22A4 | 0.486925 |
| ICAM1 | SLC35G1 | 1.274349 | ABCG1 | 0.361173 | SLC25A34 | 0.310395 |
| SLC19A1 | ABCA1 | 1.261972 | SLC7A11-AS1 | 0.327711 | SLC7A11-AS1 | 0.292754 |
| SLC25A34 | SLC16A5 | 1.239062 | ICAM1 | 0.312971 | VWF | 0.215762 |
| SLC2A12 | SLC25A27 | 1.123599 | SLC22A4 | 0.311468 | SLC9A9 | 0.175152 |
| SLC2A6 | SLC25A21-AS1 | 1.101742 | SLC9A9 | 0.280095 | PECAM1 | 0.142662 |
| SLC39A11 | SLC27A1 | 1.077825 | VWF | 0.207022 | SLC43A1 | 0.140407 |
| SLC35G1 | SLC43A2 | 1.056906 | PECAM1 | 0.091256 | ABCA6 | 0.059977 |
| ABCA1 | CLDN20 | 1.054052 | ABCA8 | 0.071191 | ABCA9 | 0.050411 |
| SLC16A5 | SLCO4A1 | 1.048847 | ABCA6 | 0.038365 | SLC17A9 | 0 |
| SLC25A27 | CLDN10 | 1.042052 | ABCA9 | 0 | ABCA8 | 0 |
| SLC25A21-AS1 | SLC22A5 | 1.033148 | ICAM2 | 0 | ICAM2 | 0 |
| SLC27A1 | JAM2 | 1.027943 | SLC15A4 | 0 | SLC15A4 | 0 |
| SLC43A2 | ABCB9 | 1.010985 | CLDN5 | 0 | CLDN5 | 0 |
| CLDN20 | | | | | | |
| SLCO4A1 | | | | | | |
| CLDN10 | | | | | | |
| SLC22A5 | | | | | | |
| JAM2 | | | | | | |
| ABCB9 | | | | | | |
| SLCO3A1 | | | | | | |
| ABCB8 | | | | | | |
| SLC15A3 | | | | | | |
| SLC25A21 | | | | | | |
| SLC39A2 | | | | | | |
| SLC24A5 | | | | | | |
| SLC4A5 | | | | | | |
| SLC8A1 | | | | | | |
| ICAM3 | | | | | | |
| CLDN10-AS1 | | | | | | |
| SLC35G6 | | | | | | |
| SLC5A4 | | | | | | |
| ABCC6P2 | | | | | | |
| ABCA2 | | | | | | |
| SLC25A22 | | | | | | |
| SLC7A8 | | | | | | |
| SLC25A35 | | | | | | |
| SLC25A53 | | | | | | |
| SLC29A3 | | | | | | |
| SLC25A10 | | | | | | |
| SLC35G5 | | | | | | |
| SLC25A51P1 | | | | | | |
| SLC9B1 | | | | | | |

TABLE 3-continued

| #506 BBB gene list | 234 gene list | hBMECs | 234 gene list | DF-BMECs | 234 gene list | UM-BMECs |
|---|---|---|---|---|---|---|
| SLC23A3 | | | | | | |
| ABCC6 | | | | | | |
| SLC5A10 | | | | | | |
| SLC37A2 | | | | | | |
| SLC35G3 | | | | | | |
| SLC25A18 | | | | | | |
| SLC45A2 | | | | | | |
| SLC26A5 | | | | | | |
| SLC51A | | | | | | |
| ABCC2 | | | | | | |
| ABCG4 | | | | | | |
| SLC46A1 | | | | | | |
| SLC9A9-AS1 | | | | | | |
| ABCA4 | | | | | | |
| SLC34A1 | | | | | | |
| SLC9A5 | | | | | | |
| SLC25A30-AS1 | | | | | | |
| SLC25A45 | | | | | | |
| SLC7A3 | | | | | | |
| SLC23A1 | | | | | | |
| SLC45A4 | | | | | | |
| ABCD1 | | | | | | |
| SLC7A5P1 | | | | | | |
| SLC2A4 | | | | | | |
| SLC25A42 | | | | | | |
| ABCA10 | | | | | | |
| CLDN1 | | | | | | |
| SLC25A5-AS1 | | | | | | |
| SLC22A17 | | | | | | |
| CLDN2 | | | | | | |
| SLC38A4 | | | | | | |
| SLC6A1OP | | | | | | |
| SLC44A3 | | | | | | |
| SLC26A4 | | | | | | |
| SLC6A9 | | | | | | |
| SLC9A7P1 | | | | | | |
| SLC36A2 | | | | | | |
| SLC27A6 | | | | | | |
| SLCO1A2 | | | | | | |
| SLC6A4 | | | | | | |
| SLC29A4 | | | | | | |
| SLC26A3 | | | | | | |
| SLC6A2 | | | | | | |
| SLC17A7 | | | | | | |
| SLC38A5 | | | | | | |
| SLC8A1-AS1 | | | | | | |
| SLC15A1 | | | | | | |
| ABCA17P | | | | | | |
| SLC35G4P | | | | | | |
| SLCO4A1-AS1 | | | | | | |
| SLC22A6 | | | | | | |
| SLC47A2 | | | | | | |
| SLC1A6 | | | | | | |
| SLC26A9 | | | | | | |
| SLC13A3 | | | | | | |
| SLC35D3 | | | | | | |
| SLC27A5 | | | | | | |
| SLC22A20 | | | | | | |
| SLC4A4 | | | | | | |
| SLC35F1 | | | | | | |
| SLC2A5 | | | | | | |
| SLC28A2 | | | | | | |
| SLC38A3 | | | | | | |
| SLC26A4-AS1 | | | | | | |
| SLC14A1 | | | | | | |
| SLC16A6 | | | | | | |
| SLC17A8 | | | | | | |
| SLC22A13 | | | | | | |
| SLC24A3 | | | | | | |
| SLC10A5 | | | | | | |
| SLC15A2 | | | | | | |
| SLC4A10 | | | | | | |
| SLC38A8 | | | | | | |
| SLC22A18 | | | | | | |

TABLE 3-continued

Gene list

| #506 BBB gene list | 234 gene list hBMECs | 234 gene list DF-BMECs | 234 gene list UM-BMECs |
|---|---|---|---|
| SLC22A18AS | | | |
| SLC13A4 | | | |
| ABCC11 | | | |
| SLC28A3 | | | |
| SLC4A9 | | | |
| SLC5A12 | | | |
| ABCB1 | | | |
| SLC5A1 | | | |
| SLC13A5 | | | |
| SLC10A1 | | | |
| CLDN16 | | | |
| SLC5A8 | | | |
| SLC22A25 | | | |
| SLC26A1 | | | |
| ABCC9 | | | |
| ABCF1 | | | |
| ABCA7 | | | |
| SLC35F4 | | | |
| SLC12A8 | | | |
| SLC8A3 | | | |
| SLC6A20 | | | |
| SLC17A4 | | | |
| SLC25A31 | | | |
| CLDN4 | | | |
| SLC6A7 | | | |
| SLC10A2 | | | |
| SLC1A2 | | | |
| SLC24A4 | | | |
| SLC11A1 | | | |
| SLC12A5 | | | |
| CLDN23 | | | |
| SLC6A11 | | | |
| CLDN9 | | | |
| SLC30A3 | | | |
| SLCO2A1 | | | |
| SLC10A4 | | | |
| SLC24A2 | | | |
| SLC39A12 | | | |
| SLC26A7 | | | |
| SLC16A14 | | | |
| SLC9C2 | | | |
| SLC27A2 | | | |
| SLC6A1 | | | |
| ABCA12 | | | |
| SLC12A1 | | | |
| SLC22A9 | | | |
| SLC22A15 | | | |
| SLC52A1 | | | |
| ABCB11 | | | |
| SLC1A7 | | | |
| SLC46A2 | | | |
| SLCO6A1 | | | |
| SLC22A11 | | | |
| SLC22A10 | | | |
| SLC32A1 | | | |
| ABCC3 | | | |
| ABCC12 | | | |
| SLCO4C1 | | | |
| ABCB5 | | | |
| SLC9A2 | | | |
| ABCC6P1 | | | |
| ABCG5 | | | |
| SLC9A3 | | | |
| SLCO1B1 | | | |
| ABCC13 | | | |
| SLC6A12 | | | |
| SLC16A10 | | | |
| SLC15A5 | | | |
| SLCO1B3 | | | |
| SLCO1C1 | | | |
| CLDN18 | | | |
| SLC5A9 | | | |
| SLC2A2 | | | |
| SLCO5A1 | | | |
| SLC7A14 | | | |

TABLE 3-continued

| #506 BBB gene list | 234 gene list hBMECs | 234 gene list DF-BMECs | 234 gene list UM-BMECs |
|---|---|---|---|
| ABCA13 | | | |
| SLC19A3 | | | |
| ABCB4 | | | |
| SLCO2B1 | | | |
| SLC34A2 | | | |
| SLC9A4 | | | |
| SLC16A12 | | | |
| ABCC8 | | | |
| SLC4A1 | | | |
| SLC8A2 | | | |
| SLC5A7 | | | |
| SLC6A19 | | | |
| ABCD2 | | | |
| SLC6A17 | | | |
| SLC25A3P1 | | | |
| SLC2A1-AS1 | | | |
| SLC51B | | | |
| SLC52A3 | | | |
| SLC6A1-AS1 | | | |
| SLC9C1 | | | |
| CLDN6 | | | |
| SLC39A7 | | | |
| SLC1A3 | | | |
| SLC29A2 | | | |
| TJP3 | | | |
| CLDN3 | | | |
| SLC7A4 | | | |
| SLC25A41 | | | |
| CLDN19 | | | |
| SLC4A3 | | | |
| CLDND2 | | | |
| CLDN8 | | | |
| SLC30A2 | | | |
| SLC44A4 | | | |
| SLC16A11 | | | |
| CLDN24 | | | |
| SLC13A2 | | | |
| SLC18A3 | | | |
| SLC22A24 | | | |
| SLC35F3 | | | |
| SLC6A16 | | | |
| SLC16A8 | | | |
| SLC25A48 | | | |
| SLC12A3 | | | |
| SLC22A3 | | | |
| SLC25A2 | | | |
| SLC6A13 | | | |
| SLC45A1 | | | |
| SLC6A3 | | | |
| SLC5A5 | | | |
| ABCG8 | | | |
| SLC34A3 | | | |
| SLC22A12 | | | |
| SLC2A9 | | | |
| SLC22A31 | | | |
| SLC14A2 | | | |
| SLC26A10 | | | |
| ICAM4 | | | |
| CLDN17 | | | |
| SLC22A7 | | | |
| SLC6A18 | | | |
| SLC36A3 | | | |
| SLC22A2 | | | |
| SLC25A47 | | | |
| SLC22A14 | | | |
| SLC22A16 | | | |
| SLC17A2 | | | |
| SLC13A1 | | | |
| SLC30A8 | | | |
| SLC30A10 | | | |
| SLC2A7 | | | |
| SLC6A5 | | | |
| SLC7A9 | | | |
| SLC26A8 | | | |
| SLC38A11 | | | |

TABLE 3-continued

| #506 BBB gene list | 234 gene list hBMECs | 234 gene list DF-BMECs | 234 gene list UM-BMECs |
|---|---|---|---|
| SLC17A1 | | | |
| SLC22A1 | | | |
| SLC22A8 | | | |
| SLC17A6 | | | |
| SLC3A1 | | | |
| SLC7A13 | | | |
| SLC5A2 | | | |
| VCAM1 | | | |
| SLC18A1 | | | |
| SLC28A1 | | | |
| SLC7A10 | | | |
| CLDN22 | | | |
| CLDN25 | | | |
| SLC10A6 | | | |
| SLC17A3 | | | |
| SLC39A5 | | | |
| SLC5A11 | | | |
| SLC6A14 | | | |
| SLCO1B7 | | | |

We claim:

1. A method for generating a population of human brain microvascular endothelial cells (BMECs) from human pluripotent stem cells, wherein the method comprises, in order,
   (a) culturing human pluripotent stem cells for about 24 hours in a chemically defined, serum-free culture medium that comprises an activator of Wnt/β-catenin signaling, whereby cells that express mesodermal markers are obtained;
   (b) culturing the cells expressing mesodermal markers for about 5 days in the presence of a chemically defined, serum-free culture medium comprising a neuronal cell culture supplement, whereby cells that express endothelial progenitor marker Flk-1 are obtained; and
   (c) culturing the Flk-1+ cells of (b) for about two days in the presence of a chemically defined, serum-free endothelial medium comprising a neuronal cell culture supplement, bFGF/FGF2, and retinoic acid (RA), whereby a cell population comprising human BMECs is obtained.

2. The method of claim 1, wherein the human pluripotent stem cells of (a) are cultured in a chemically defined, serum-free culture medium at a cell density of about $35 \times 10^3$ cells/cm' for about 3 days prior to exposure to the chemically defined, serum-free culture medium comprising an activator of Wnt/β-catenin signaling.

3. The method of claim 1, wherein at least 95% of cells of the cell population comprising human BMECs are BMECs positive for expression of one or more of CD31, p-glycoprotein (Pgp), occludin, and claudin-5.

4. The method of claim 1, further comprising growing the human BMECs of step (c) as a monolayer to confluence.

5. The method of claim 4, comprising the step of taking an initial transendothelial electrical resistance (TEER) measurement of the confluent monolayer, wherein the TEER measurement is greater than 2000 Ohm $(\Omega) \times cm^2$.

6. The method of claim 1, wherein the activator of Wnt/β-catenin signaling is a Gsk3 inhibitor.

7. The method of claim 6, wherein the Gsk3 inhibitor is a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide.

8. The method of claim 6, wherein the Gsk3 inhibitor is CHIR99021 and is present in a concentration of about 3 μM to about 12 μM.

9. The method of claim 1, wherein no selecting, separating, or enriching steps are applied to the cells of step (a), (b), and (c) to generate the cell population of human BMECs.

* * * * *

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: For GAPDH

<400> SEQUENCE: 1
ctgatttggt cgtattgggc                                           20

<210> SEQ ID NO 2
<211> LENGTH: 20
<212> TYPE: DNA
<213> ORGANISM: Artificial Sequence
<220> FEATURE:
<223> OTHER INFORMATION: Rev GAPDH

<400> SEQUENCE: 2
tggaagatgg tgatgggatt                                           20

<210> SEQ ID NO 3
<211> LENGTH: 21
<212> TYPE: DNA
<213> ORGANISM: Artificial Sequence
<220> FEATURE:
<223> OTHER INFORMATION: For SLC2A1

<400> SEQUENCE: 3
aactcttcag ccagggtcca c                                         21

<210> SEQ ID NO 4
<211> LENGTH: 21
<212> TYPE: DNA
<213> ORGANISM: Artificial Sequence
<220> FEATURE:
<223> OTHER INFORMATION: Rev SLC2A1

<400> SEQUENCE: 4
cacagtgaag atgatgaaga c                                         21

<210> SEQ ID NO 5
<211> LENGTH: 22
<212> TYPE: DNA
<213> ORGANISM: Artificial Sequence
<220> FEATURE:
<223> OTHER INFORMATION: For ABCB1

<400> SEQUENCE: 5
ctcatcgttt gtctacagtt cg                                          22

<210> SEQ ID NO 6
<211> LENGTH: 20
<212> TYPE: DNA
<213> ORGANISM: Artificial Sequence
<220> FEATURE:
<223> OTHER INFORMATION: Rev ABCB1

<400> SEQUENCE: 6
aagacatttc caaggcatca                                             20

<210> SEQ ID NO 7
<211> LENGTH: 22
<212> TYPE: DNA
<213> ORGANISM: Artificial Sequence
<220> FEATURE:
<223> OTHER INFORMATION: For PECAM1

<400> SEQUENCE: 7
gagtattact gcacagcctt ca                                          22

<210> SEQ ID NO 8
<211> LENGTH: 22
<212> TYPE: DNA
<213> ORGANISM: Artificial Sequence
<220> FEATURE:
<223> OTHER INFORMATION: Rev PECAM1

<400> SEQUENCE: 8
aaccactgca ataagtcctt tc                                          22

<210> SEQ ID NO 9
<211> LENGTH: 21
<212> TYPE: DNA
<213> ORGANISM: Artificial Sequence
<220> FEATURE:
<223> OTHER INFORMATION: For OCLN

<400> SEQUENCE: 9
gacttcaggc agcctcgtta c                                           21

<210> SEQ ID NO 10
<211> LENGTH: 22
<212> TYPE: DNA
<213> ORGANISM: Artificial Sequence
<220> FEATURE:
<223> OTHER INFORMATION: Rev OCLN

<400> SEQUENCE: 10
gccagttgtg tagtctgtct ca                                          22

<210> SEQ ID NO 11
<211> LENGTH: 20
<212> TYPE: DNA
<213> ORGANISM: Artificial Sequence
<220> FEATURE:

<223> OTHER INFORMATION: For CLDN5

<400> SEQUENCE: 11
gttcgccaac attgtcgtcc                                               20

<210> SEQ ID NO 12
<211> LENGTH: 23
<212> TYPE: DNA
<213> ORGANISM: Artificial Sequence
<220> FEATURE:
<223> OTHER INFORMATION: Rev CLDN5

<400> SEQUENCE: 12
gtagttcttc ttgtcgtagt cgc                                           23

<210> SEQ ID NO 13
<211> LENGTH: 21
<212> TYPE: DNA
<213> ORGANISM: Artificial Sequence
<220> FEATURE:
<223> OTHER INFORMATION: For TJP1

<400> SEQUENCE: 13
accagtaagt cgtcctgatc c                                             21

<210> SEQ ID NO 14
<211> LENGTH: 21
<212> TYPE: DNA
<213> ORGANISM: Artificial Sequence
<220> FEATURE:
<223> OTHER INFORMATION: Rev TJP1

<400> SEQUENCE: 14
tcggccaaat cttctcactc c                                             21

<210> SEQ ID NO 15
<211> LENGTH: 20
<212> TYPE: DNA
<213> ORGANISM: Artificial Sequence
<220> FEATURE:
<223> OTHER INFORMATION: For CDH5

<400> SEQUENCE: 15
aagcgtgagt cgcaagaatg                                               20

<210> SEQ ID NO 16
<211> LENGTH: 20
<212> TYPE: DNA
<213> ORGANISM: Artificial Sequence
<220> FEATURE:
<223> OTHER INFORMATION: Rev CDH5

<400> SEQUENCE: 16
tctccaggtt ttcgccagtg                                               20

<210> SEQ ID NO 17
<211> LENGTH: 22
<212> TYPE: DNA
<213> ORGANISM: Artificial Sequence
<220> FEATURE:
<223> OTHER INFORMATION: For KDR

<400> SEQUENCE: 17
gtgatcggaa atgacactgg ag                                            22

```
<210> SEQ ID NO 18
<211> LENGTH: 23
<212> TYPE: DNA
<213> ORGANISM: Artificial Sequence
<220> FEATURE:
<223> OTHER INFORMATION: Rev KDR

<400> SEQUENCE: 18
catgttggtc actaacagaa gca                                              23

<210> SEQ ID NO 19
<211> LENGTH: 23
<212> TYPE: DNA
<213> ORGANISM: Artificial Sequence
<220> FEATURE:
<223> OTHER INFORMATION: For CD34

<400> SEQUENCE: 19
ctacaacacc tagtaccctt gga                                              23

<210> SEQ ID NO 20
<211> LENGTH: 22
<212> TYPE: DNA
<213> ORGANISM: Artificial Sequence
<220> FEATURE:
<223> OTHER INFORMATION: Rev CD34

<400> SEQUENCE: 20
ggtgaacact gtgctgatta ca                                               22

<210> SEQ ID NO 21
<211> LENGTH: 20
<212> TYPE: DNA
<213> ORGANISM: Artificial Sequence
<220> FEATURE:
<223> OTHER INFORMATION: For OCT4

<400> SEQUENCE: 21
gtggaggaag ctgacaacaa                                                  20

<210> SEQ ID NO 22
<211> LENGTH: 20
<212> TYPE: DNA
<213> ORGANISM: Artificial Sequence
<220> FEATURE:
<223> OTHER INFORMATION: Rev OCT4

<400> SEQUENCE: 22
attctccagg ttgcctctca                                                  20

<210> SEQ ID NO 23
<211> LENGTH: 21
<212> TYPE: DNA
<213> ORGANISM: Artificial Sequence
<220> FEATURE:
<223> OTHER INFORMATION: For NANOG

<400> SEQUENCE: 23
tttgtgggcc tgaagaaaac t                                                21

<210> SEQ ID NO 24
<211> LENGTH: 21
<212> TYPE: DNA
<213> ORGANISM: Artificial Sequence
<220> FEATURE:
<223> OTHER INFORMATION: Rev NANOG
```

```
<400> SEQUENCE: 24
agggctgtcc tgaataagca g                                              21

<210> SEQ ID NO 25
<211> LENGTH: 20
<212> TYPE: DNA
<213> ORGANISM: Artificial Sequence
<220> FEATURE:
<223> OTHER INFORMATION: For Brachyury

<400> SEQUENCE: 25
gggagcgagg aggaagggaa                                                20

<210> SEQ ID NO 26
<211> LENGTH: 20
<212> TYPE: DNA
<213> ORGANISM: Artificial Sequence
<220> FEATURE:
<223> OTHER INFORMATION: Rev Brachyury

<400> SEQUENCE: 26
tggtgacggt gctgaagtgc                                                20

<210> SEQ ID NO 27
<211> LENGTH: 20
<212> TYPE: DNA
<213> ORGANISM: Artificial Sequence
<220> FEATURE:
<223> OTHER INFORMATION: For MIXL1

<400> SEQUENCE: 27
ggcgtcagag tgggaaatcc                                                20

<210> SEQ ID NO 28
<211> LENGTH: 21
<212> TYPE: DNA
<213> ORGANISM: Artificial Sequence
<220> FEATURE:
<223> OTHER INFORMATION: Rev MIXL1

<400> SEQUENCE: 28
ggcaggcagt tcacatctac c                                              21

<210> SEQ ID NO 29
<211> LENGTH: 23
<212> TYPE: DNA
<213> ORGANISM: Artificial Sequence
<220> FEATURE:
<223> OTHER INFORMATION: For PAX2

<400> SEQUENCE: 29
tcaagtcgag tctatctgca tcc                                            23

<210> SEQ ID NO 30
<211> LENGTH: 21
<212> TYPE: DNA
<213> ORGANISM: Artificial Sequence
<220> FEATURE:
<223> OTHER INFORMATION: Rev PAX2

<400> SEQUENCE: 30
catgtcacga ccagtcacaa c                                              21
```